US 7,696,308 B2

(12) United States Patent
Longacre-Andre et al.

(10) Patent No.: US 7,696,308 B2
(45) Date of Patent: *Apr. 13, 2010

(54) **RECOMBINANT PROTEIN CONTAINING A C-TERMINAL FRAGMENT OF *PLASMODIUM* MSP-1**

(75) Inventors: Shirley Longacre-Andre, Paris (FR); Charles Roth, Rueil-Malmaison (FR); Faridabano Nato, Antony (FR); John W. Barnwell, Stone Mountain, GA (US); Kamini Mendis, Columbo 8 (LK)

(73) Assignees: Institut Pasteur, Paris (FR); New York University, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/144,833

(22) Filed: Jun. 6, 2005

(65) Prior Publication Data

US 2006/0018932 A1    Jan. 26, 2006

Related U.S. Application Data

(63) Continuation of application No. 09/125,031, filed as application No. PCT/FR97/00290 on Feb. 14, 1997, now Pat. No. 6,958,235.

(30) Foreign Application Priority Data

Feb. 14, 1996    (FR) .................................. 96 01822

(51) Int. Cl.
*A61K 38/00*    (2006.01)
*A01N 63/00*    (2006.01)
*C07H 21/00*    (2006.01)

(52) U.S. Cl. ...................... 530/300; 424/93.2; 536/23.4
(58) Field of Classification Search ................. 530/300; 424/93.2; 536/23.4
See application file for complete search history.

(56) References Cited

U.S. PATENT DOCUMENTS 6,096,304 A     8/2000  McCutchen
6,958,235 B1 * 10/2005 Longacre-Andre et al. ....... 435/320.1
2002/0076403 A1  6/2002  Longacre-Andre et al.

FOREIGN PATENT DOCUMENTS

EP    0 154 454    9/1985
EP     0621337    10/1994
WO    93/17107    9/1993

OTHER PUBLICATIONS

Hui et al., Immunogenicity of C-terminal 19-kDA Fragment of *Plasmodium falciparum*. The Journal of Immunology, vol. 153, pp. 2544-2553, 1994.*

Hui et al., Induction of Antibodies to the *Plasmodium falciparum* Merozoite Surface Protein-1 (MSP1) . The Journal of Immunology, vol. 153, pp. 1195-1201, 1994.*

Longacre, et al., 1994, *Plasmodium vivax* merozoite surface protein 1 C-terminal recombinant proteins in baculovirus Molecular and Biochemical Parasitology 64: 191-205.

Chappel, et al., 1993, Monoclonal antibodies that inhibit *Plasmodium falciparum* invasion in vitro recognise the first growth factor-like domain of merozoite surface protein-1. Molecular and Biochemical Parasitology 60: 303-311.

Chang, et al., 1992, A carboxyl-terminal fragment of *Plasmodium falciparum* gp195 expressed by a recombinant baculovirus Induces antibodies that completely inhibit parasite growth. Journal of Imunology 149: 548-555.

Miller, et al., 1993, Analysis of sequence diversity in the *Plasmodium falciparum* merozoite surface proteln-1 (MSP-1). Molecular and Biochemical Parasitology 59: 1-14.

Molecular and Biochemical Parasitology, vol. 74, No. 1, Dec. 20, 1995, pp. 105-111, XP000603955, Longacre, S.: "The Plasmodium cynomolgimerozoite surface protein 1 C-terminal sequence and its homologies with other *Plasmodium* species" cite dans la demande volt p. 107, colonne 1, ligne 4-ligne 9.

Molecular and Biochemical Parasitology, vol. 64, No. 2, Jan. 1, 1994, pp. 191-205, XP000603954, Longacre, S. et al.: "*Plasmodium vivax* merozoite surface protein 1 C-terminal recombinant proteins in baculovirus" cite dans la demande voir let document en entier.

Molecular and Biochemical Parasitlogy, vol. 60, No. 2, Jan. 1, 1993, pp. 303-310, XP000603763, Chappel. J.A. & Holder, A.A.: "Monoclonal antibodies that inhibit *Plasmodium falciparum* invasion in vitro recognise the first growth factor-like domain of merozoite surface protein-1" voir le document en entler.

Journal of Immunology, vol. 149, No. 2, Jul. 15, 1992, pp. 548-555, XP000605417, Chang, S.P. et al.: A carboxy-terminal fragment of *Plasmodium falciparum* gp195 expressed by a recombinant baculovirus Induces antibodies that completely inhibit parasie growth voir le document en entler.

FASEB Journal, vol. 10, No. 6, Jun. 2, 1996, p. A1117 XP000604872, Angov E. et al.. "Characterization of a Recombinant *Plasmodium falciparium* MSP 1 C-Terminal Fragment Using Conformation-Specific Monoclonal Antibodies", volr abrege.

* cited by examiner

*Primary Examiner*—Robert Mondesi
*Assistant Examiner*—Khatol Shahnan-Shah
(74) *Attorney, Agent, or Firm*—Oblon, Spivak, McClelland, Maier & Neustadt, L.L.P.

(57) ABSTRACT

The invention relates to a recombinant protein fabricated in a baculovirus system, of which the essential constitutive polypeptide sequence is that of a C-terminal fragment of 19 kilodalton (p19) of the surface protein 1 (protein MSP-1) of the merozoite parasite of the *Plasmodium* type, particularly *Plasmodium falciparum*, which is infectious for humans, said C-terminal fragment remaining normally anchored at the surface of the parasite at the end of its penetration phase into human erythrocytes, in the occurrence of an infectious cycle. Said recombinant protein is applicable to the production of vaccines against malaria.

8 Claims, 35 Drawing Sheets

```
        E   F   N   I   S   Q   H   Q   C   V   K   K   Q   C   P   E   N
Bac 19  GAA TTC AAC ATC TCG CAG CAC CAA TGC GTG AAA AAA CAA TGT CCC GAG AAC
            ||| ||  ||  ||  ||| ||| ||| ||  ||| ||| ||| ||| ||  ||  ||
PF  19      AAC ATT TCA CAA CAC CAA TGC GTA AAA AAA CAA TGT CCA GAA AAT

S   G   C   F   R   H   L   D   E   R   E   E   C   K   C   L   L
Bac 19  TCT GGC TGT TTC AGA CAC TTG GAC GAG AGA GAG GAG TGT AAA TGT CTG CTG
        ||| ||  ||| ||| ||| ||  ||  ||  ||  ||| ||  ||  ||| ||| |||  |   |
PF  19  TCT GGA TGT TTC AGA CAT TTA GAT GAA AGA GAA GAA TGT AAA TGT TTA TTA

N   Y   K   Q   E   G   D   K   C   V   E   N   P   N   P   T   C
Bac 19  AAC TAC AAA CAG GAG GGC GAC AAG TGC GTG GAG AAC CCC AAC CCG ACC TGT
        ||  ||| ||| ||  ||  ||  ||  ||  ||  ||  ||  ||  ||  ||  ||  ||  |||
PF  19  AAT TAC AAA CAA GAA GGT GAT AAA TGT GTT GAA AAT CCA AAT CCT ACT TGT

N   E   N   N   G   G   C   D   A   D   A   K   C   T   E   E   D
Bac 19  AAC GAG AAC AAC GGC GGC TGT GAC GCA GAC GCC AAA TGC ACC GAG GAG GAC
        ||| ||  ||  ||  ||  ||  ||| ||  ||| ||  ||| ||| ||  ||| ||  ||  ||
PF  19  AAC GAA AAT AAT GGT GGA TGT GAT GCA GAT GCC AAA TGT ACC GAA GAA GAT

S   G   S   N   G   K   K   I   T   C   E   C   T   K   P   D   S
Bac 19  TCG GGC AGC AAC GGC AAG AAA ATC ACG TGT GAG TGT ACC AAA CCC GAC TCG
        ||  ||  ||| ||| ||  ||| ||| ||| ||  ||| ||  ||| ||  ||| ||  ||  ||
PF  19  TCA GGT AGC AAC GGA AAG AAA ATC ACA TGT GAA TGT ACT AAA CCT GAT TCT

Y   P   L   F   D   G   I   F   C   S   *   *
Bac 19  TAC CCG CTG TTC GAC GGC ATC TTC TGC AGC TAA TAA
        ||  ||  ||  ||| ||  ||  ||  ||| ||| ||
PF  19  TAT CCA CTT TTC GAT GGT ATT TTC TGC AGT
```

```
            Site Eco RI
             E   F   N   I   S   Q   H   Q   C   V   K   K   Q   C   P   E   N
Bac 19      GAA TTC AAC ATC TCG CAG CAC CAA TGC GTG AAA AAA CAA TGT CCC GAG AAC
                ||| || || || ||| ||| ||| || ||| ||| ||| ||| || || ||
PF 19           AAC ATT TCA CAA CAC CAA TGC GTA AAA AAA CAA TGT CCA GAA AAT S   G   C   F   R   H   L   D   E   R   E   E   C   K   C   L   L
Bac 19      TCT GGC TGT TTC AGA CAC TTG GAC GAG AGA GAG GAG TGT AAA TGT CTC CTC
            ||| ||  ||| ||| ||| || || || || ||| || || ||| ||| ||| |   |
PF 19       TCT GGA TGT TTC AGA CAT TTA GAT GAA AGA GAA GAA TGT AAA TGT TTA TTA N   Y   K   Q   E   G   D   K   C   V   E   N   P   N   P   T   C
Bac 19      AAC TAC AAA CAG GAG GGC GAC AAG TGC GTG GAG AAC CCC AAC CCG ACC TGT
            ||  ||| ||| || || || || || || || || || || || || || |||
PF 19       AAT TAC AAA CAA GAA GGT GAT AAA TGT GTT GAA AAT CCA AAT CCT ACT TGT N   E   N   N   G   G   C   D   A   D   A   K   C   T   E   E   D
Bac 19      AAC GAG AAC AAC GGC GGC TGT GAC GCA GAC GCC AAA TGC ACC GAG GAG GAC
            ||| || || || || || ||| || ||| ||| ||| ||| || ||| || || ||
PF 19       AAC GAA AAT AAT GGT GGA TGT GAT CCA GAT GCC AAA TGT ACC GAA GAA GAT S   G   S   N   G   K   K   I   T   C   E   C   T   K   P   D   S
Bac 19      TCC GGC AGC AAC GGC AAG AAA ATC ACG TGT GAG TGT ACC AAA CCC GAC TCC
            || || ||| ||| || ||| ||| ||| || ||| || ||| || ||| || || ||
PF 19       TCA GGT AGC AAC GGA AAG AAA ATC ACA TGT GAA TGT ACT AAA CCT GAT TCT Y   P   L   F   D   G   I   F   C   S   S   S   N   F   L   G   I
Bac 19      TAC CCG CTG TTC GAC GGC ATC TTC TGC AGC TCC TCT AAC TTC TTG GGC ATC
            || || || ||| || || || ||| ||| || ||| ||| ||| ||| || || ||
PF 19       TAT CCA CTT TTC GAT GGT ATT TTC TGC AGT TCC TCT AAC TTC TTA GGA ATA S   F   L   L   I   L   M   L   I   L   Y   S   F   I   *   *
Bac 19      TCG TTC TTG TTG ATC CTC ATG TTG ATC TTG TAC AGC TTC ATT TAA TAA
            || ||| || || || ||| ||| || || ||| || ||| || ||| |||
PF 19       TCA TTC TTA TTA ATA CTC ATG TTA ATA TTA TAC AGT TTC ATT
```

```
ATG AAG GCG CTA CTC TTT TTG TTC TCT TTC ATT TTT TTC GTT ACC AAA TGT
 M   K   A   L   L   F   L   F   S   F   I   F   F   V   T   K   C

CAA TGT GAA ACA GAA AGT TAT AAG CAG CTT GTA GCC AAC GTG GAC GAA TTC
 Q   C   E   T   E   S   Y   K   Q   L   V   A   N   V   D   E   F

AAC ATC TCG CAG CAC CAA TGC GTG AAA AAA CAA TGT CCC GAG AAC TCT GGC
 N   I   S   Q   H   Q   C   V   K   K   Q   C   P   E   N   S   G

TGT TTC AGA CAC TTG GAC GAG AGA GAG GAG TGT AAA TGT CTG CTG AAC TAC
 C   F   R   H   L   D   E   R   E   E   C   K   C   L   L   N   Y

AAA CAG GAG GGC GAC AAG TGC GTG GAG AAC CCC AAC CCG ACC TGT AAC GAG
 K   Q   E   G   D   K   C   V   E   N   P   N   P   T   C   N   E

AAC AAC GGC GGC TGT GAC GCA GAC GCC AAA TGC ACC GAG GAG GAC TCG GGC
 N   N   G   G   C   D   A   D   A   K   C   T   E   E   D   S   G

AGC AAC GGC AAG AAA ATC ACG TGT GAG TGT ACC AAA CCC GAC TCG TAC CCG
 S   N   G   K   K   I   T   C   E   C   T   K   P   D   S   Y   P

CTG TTC GAC GGC ATC TTC TGC AGC TAA TAA
 L   F   D   G   I   F   C   S   *   *
```

*FIG. 1C*

```
GAA ACA GAA AGT TAT AAG CAG CTT GTA GCC AAC GTG GAC GAA TTC
 E   T   E   S   Y   K   Q   L   V   A   N   V   D   E   F

AAC ATC TCG CAG CAC CAA TGC GTG AAA AAA CAA TGT CCC GAG AAC TCT GGC
 N   I   S   Q   H   Q   C   V   K   K   Q   C   P   E   N   S   G

TGT TTC AGA CAC TTG GAC GAG AGA GAG GAG TGT AAA TGT CTG CTG AAC TAC
 C   F   R   H   L   D   E   R   E   E   C   K   C   L   L   N   Y

AAA CAG GAG GGC GAC AAG TGC GTG GAG AAC CCC AAC CCG ACC TGT AAC GAG
 K   Q   E   G   D   K   C   V   E   N   P   N   P   T   C   N   E

AAC AAC GGC GGC TGT GAC GCA GAC GCC AAA TGC ACC GAG GAG GAC TCG GGC
 N   N   G   G   C   D   A   D   A   K   C   T   E   E   D   S   G

AGC AAC GGC AAG AAA ATC ACG TGT GAG TGT ACC AAA CCC GAC TCG TAC CCG
 S   N   G   K   K   I   T   C   E   C   T   K   P   D   S   Y   P

CTG TTC GAC GGC ATC TTC TGC AGC TAA TAA
 L   F   D   G   I   F   C   S   *   *
```

```
         361
CYNOMOLGI      IVCKCTKEGS EPLFEGVFCS
VIVAX(BELEM)   IVCKCTKEGS EPLFEGVFCS
VIVAX(SAl-1)   IVCKCTKEGS EPLFEGVFCS
CONSENSUS      IVCKCTKEGS EPLFEGVFCS
```

VACCINATION TEST: RECOMBINANT MSP-1 (P42 AND P19) FROM PLASMODIUM CYNOMOLGI IN THE MACACA SINICA TOQUE MACAQUE

| | | YEAR | 95 | 95 | 95 | 95 | 95 | 95 | 95 | 95 | 95 | 95 | 95 | 95 | 95 |
|---|---|---|---|---|---|---|---|---|---|---|---|---|---|---|---|
| | | MONTH | 7 | 7 | 7 | 7 | 7 | 7 | 7 | 7 | 7 | 7 | 7 | 7 | 7 |
| | | DAY | 19 | 20 | 21 | 22 | 23 | 24 | 25 | 26 | 27 | 28 | 29 | 30 | 31 |
| | | DAYS POST-INFECTION | 5 | 6 | 7 | 8 | 9 | 10 | 11 | 12 | 13 | 14 | 15 | 16 | 17 |
| VACCINATION p42 | T434 | | .004 | – | – | – | – | – | – | – | – | – | – | – | – |
| | T435 | | – | .002 | .008 | .02 | .006 | .01 | .008 | .008 | .06 | .006 | .02 | .03 | .002 |
| | T428 | | – | – | – | – | – | – | – | – | – | – | – | – | – |
| VACCINATION p19 | T429 | | – | – | – | – | – | – | – | – | – | – | – | – | – |
| | T426 | | – | .002 | – | – | – | – | – | – | – | – | – | – | – |
| | T455 | | – | – | – | .002 | – | – | – | – | .002 | – | – | – | – |
| VACCINATION p42+p19 | T430 | | .02 | – | – | – | – | – | – | – | .002 | – | – | – | – |
| | T431 | | – | – | – | – | – | – | – | – | – | – | – | – | .002 |
| | T433 | | .002 | – | .004 | – | – | – | – | – | – | – | – | – | – |
| CONTROLS PHYSIOLOGICAL WATER FCA/FIAT | T425 | | .006 | .05 | 0.1 | .006 | .002 | .002 | .006 | .004 | .03 | .04 | .03 | .02 | .03 |
| | T436 | | – | .004 | .008 | 0.05 | 0.1 | 0.09 | 0.39 | 0.4 | 0.3 | 0.1 | 0.09 | 0.1 | .3 |
| | T438 | | 0.008 | 0.01 | 0.1 | 0.6 | 0.5 | 0.6 | 0.05 | 0.1 | 0.07 | 0.03 | 0.1 | 0.1 | .32 |
| CONTROLS NON VACCINATED | T437 | | .004 | .008 | 0.1 | 0.4 | 0.1 | 0.06 | 0.2 | 1.0 | 0.03 | 0.1 | 0.05 | 0.08 | .17 |
| | T440 | | .006 | .01 | 1.04 | 1.5 | 1.8 | 1.6 | 1.5 | 0.3 | 0.12 | 0.28 | 0.4 | 0.12 | .12 |
| | T441 | | .004 | .008 | 0.8 | 2.1 | 1.7 | 3.8 | 1.04 | 0.27 | 0.1 | 1.5 | 0.9 | 0.9 | .16 |

– = ABSENCE OF PARASITES IN 400 MICROSCOPIC FIELDS

| | | | | | | | | | | | | | | |
|---|---|---|---|---|---|---|---|---|---|---|---|---|---|---|
| 95 | 95 | 95 | 95 | 95 | 95 | 95 | 95 | 95 | 95 | 95 | 95 | 95 | 95 | 95 |
| 8 | 8 | 8 | 8 | 8 | 8 | 8 | 8 | 8 | 8 | 8 | 8 | 8 | 8 | 8 |
| 1 | 2 | 3 | 4 | 5 | 6 | 7 | 8 | 9 | 10 | 11 | 12 | 13 | 14 | 15 |
| 18 | 19 | 20 | 21 | 22 | 23 | 24 | 25 | 26 | 27 | 28 | 29 | 30 | 31 | 32 |
| – | – | – | – | – | – | – | – | – | – | – | – | – | – | – |
| | .002 | .008 | .008 | .004 | .004 | – | – | – | – | – | – | – | – | – |
| | – | – | – | – | – | – | – | – | – | – | – | – | – | – |
| | – | – | – | – | – | – | – | – | – | – | – | – | – | – |
| | – | – | – | – | – | – | – | – | – | – | – | – | – | – |
| | – | – | – | – | – | – | – | – | – | – | – | – | – | – |
| | – | – | – | – | – | – | – | – | – | – | – | – | – | – |
| | – | – | – | – | – | – | – | – | – | – | – | – | – | – |
| | .02 | .01 | .05 | ND | .02 | – | – | – | .004 | .01 | .06 | .04 | .03 | .008 |
| | .08 | .02 | .01 | .01 | .01 | .02 | .01 | .004 | .004 | .02 | .004 | .008 | .004 | .004 |
| | .03 | – | – | – | .01 | .03 | .02 | .01 | .008 | .05 | .004 | .008 | – | – |
| | .1 | .006 | .03 | .01 | .008 | .02 | .01 | .008 | .01 | .01 | .008 | .01 | – | – |
| | .02 | .004 | .08 | .04 | .04 | .03 | .01 | .01 | .04 | 0.2 | .005 | .03 | .004 | .004 |
| | .02 | .02 | .02 | .06 | .004 | .02 | .008 | .01 | .008 | .004 | .004 | .008 | .008 | .004 |

CONTINUED TO FIG. 6G.2

VACCINATION TEST: RECOMBINANT MSP-1 (p19) OF PLASMODIUM
CYNOMOLGI IN THE MACACA SINICA TOQUE MACAQUE; SECOND CHALLENGE INFECTION

| YEAR | 96 | 96 | 96 | 96 | 96 | 96 | 96 | 96 | 96 | 96 | 96 | 96 | 96 | 96 | 96 | 96 | 96 | 96 |
|---|---|---|---|---|---|---|---|---|---|---|---|---|---|---|---|---|---|---|
| MONTH | 2 | 2 | 2 | 2 | 2 | 2 | 2 | 2 | 2 | 2 | 2 | 2 | 2 | 2 | 2 | 2 | 2 | 2 |
| DAYS POST-INFECTION | 3 | 4 | 5 | 6 | 7 | 8 | 9 | 10 | 11 | 12 | 13 | 14 | 15 | 16 | 17 | 18 | 19 | 20 |
| DAYS AFTER CHALLENGE | 4 | 5 | 6 | 7 | 8 | 9 | 10 | 11 | 12 | 13 | 14 | 15 | 16 | 17 | 18 | 19 | 20 | 21 |
| VACCINATION p19 | | | | | | | | | | | | | | | | | | |
| T426 | – | – | – | – | – | .008 | – | – | – | – | – | – | – | – | – | – | – | – |
| T427 | – | – | – | – | – | – | – | – | – | – | – | – | – | – | – | – | – | – |
| T429 | – | – | – | – | – | – | – | – | – | – | – | – | – | – | – | – | – | – |
| CONTROLS PHYSIOLOGICAL WATER FCA/FLA | | | | | | | | | | | | | | | | | | |
| T436 | – | – | – | – | – | – | – | – | – | – | – | – | – | – | – | – | – | – |
| T425 | – | – | – | – | – | – | – | – | – | .008 | – | – | – | – | – | – | – | – |
| T438 | – | – | – | – | – | – | – | – | – | – | – | – | – | – | – | – | – | – |
| CONTROLS NON VACCINATED | | | | | | | | | | | | | | | | | | |
| T448 | .008 | .03 | .05 | .1 | .3 | .7 | .8 | .16 | .14 | .09 | .008 | .004 | .004 | .008 | .008 | .008 | .008 | .008 |
| T449 | .004 | .01 | .02 | .02 | .3 | .07 | .5 | .8 | .2 | .07 | .07 | .04 | .06 | .06 | .05 | .03 | .03 | .02 |

– = ABSENCE OF PARASITES IN 400 MICROSCOPIC FIELDS

*FIG. 8D*

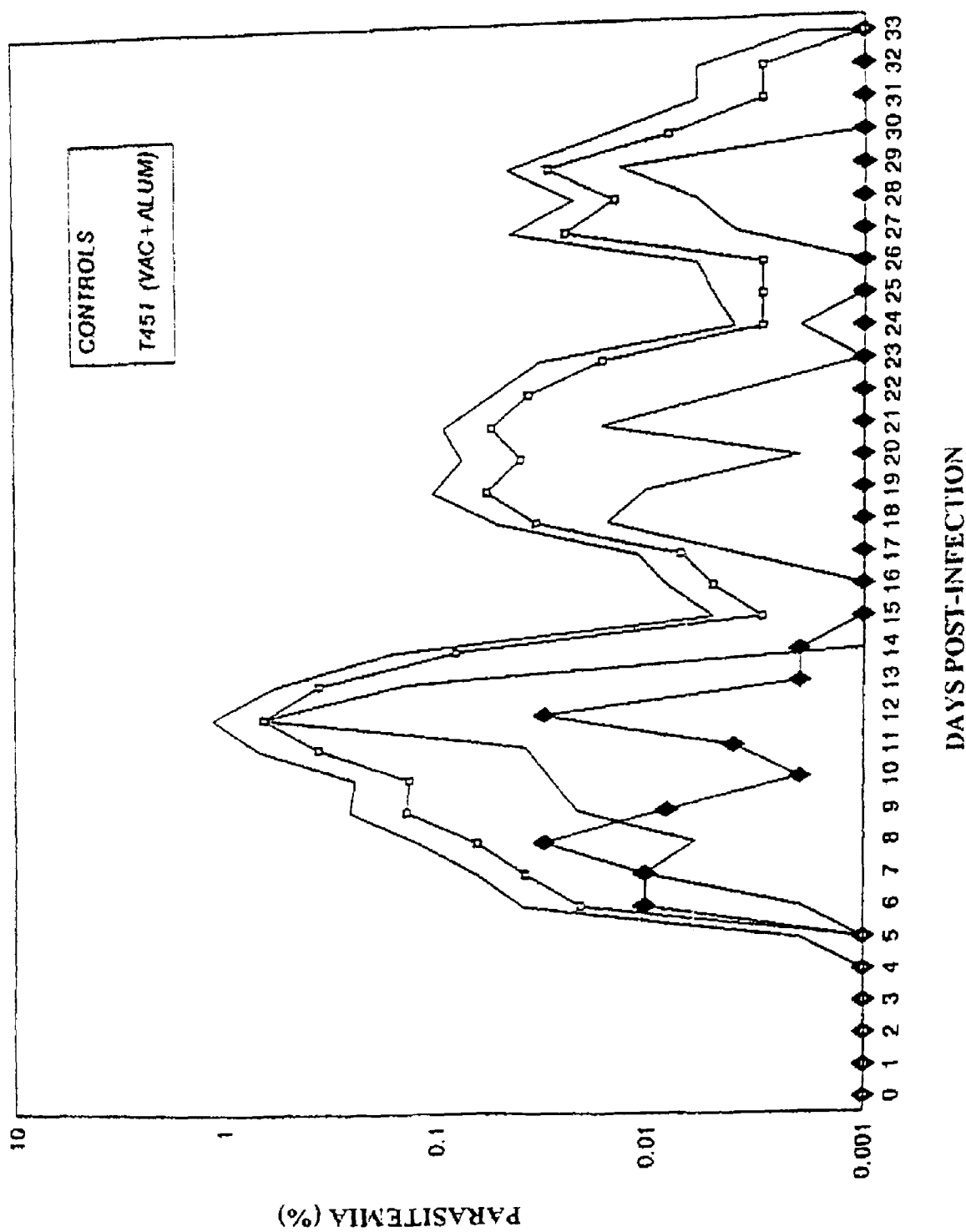

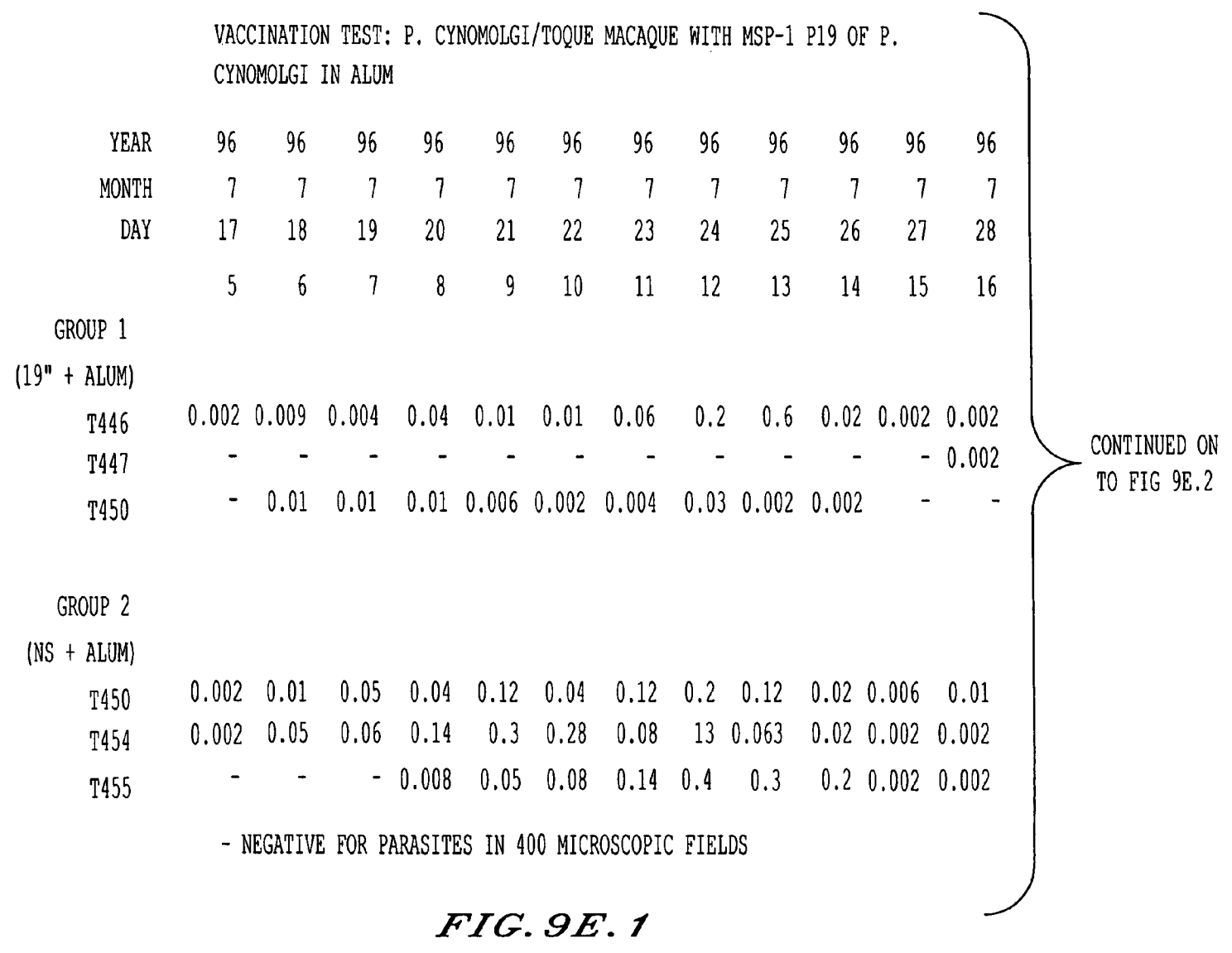

VACCINATION TEST: P. CYNOMOLGI/TOQ

| 96 | 96 | 96 | 96 | 96 | 96 | 96 | 96 | 96 | 96 | 96 | 96 | 96 | 96 |
|---|---|---|---|---|---|---|---|---|---|---|---|---|---|
| 7 | 7 | 7 | 8 | 8 | 8 | 8 | 8 | 8 | 8 | 8 | 8 | 8 | 8 |
| 29 | 30 | 31 | 1 | 2 | 3 | 4 | 5 | 6 | 7 | 8 | 9 | 10 | 11 |
| 17 | 18 | 19 | 20 | 21 | 22 | 23 | 24 | 25 | 26 | 27 | 28 | 29 | 30 |
| 0.01 | 0.06 | 0.005 | 0.06 | 0.02 | 0.004 | 0.002 | 0.002 | 0.002 | 0.002 | 0.006 | 0.006 | 0.006 | 0.004 |
| - | 0.002 | - | - | 0.01 | 0.006 | 0.004 | 0.009 | 0.006 | 0.01 | 0.04 | 0.002 | 0.02 | 0.004 |
| - | - | - | - | - | - | - | - | - | - | - | - | - | - |
| 0.01 | 0.05 | 0.04 | 0.006 | 0.001 | 0.001 | 0.001 | 0.004 | 0.006 | 0.006 | 0.05 | 0.02 | 0.04 | 0.002 |
| 0.01 | 0.04 | 0.12 | 0.09 | 0.09 | 0.008 | 0.008 | 0.002 | 0.002 | 0.004 | 0.02 | 0.02 | 0.04 | 0.02 |
| 0.002 | 0.006 | 0.01 | 0.02 | 0.07 | 0.1 | 0.04 | 0.002 | - | - | 0.002 | 0.002 | 0.006 | 0.002 |

CONTINUED FROM FIG. 9E.1

*FIG. 9E.2*

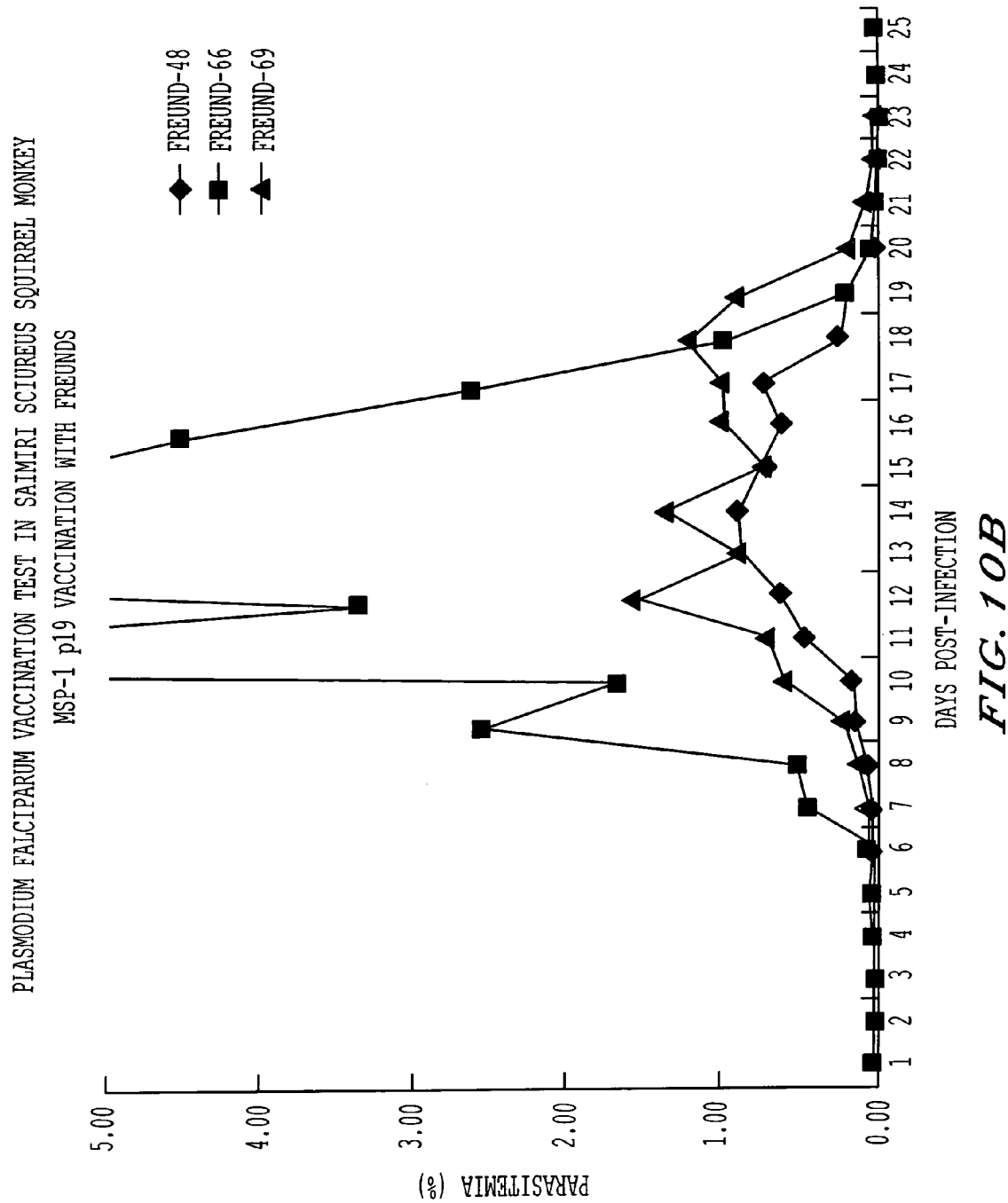

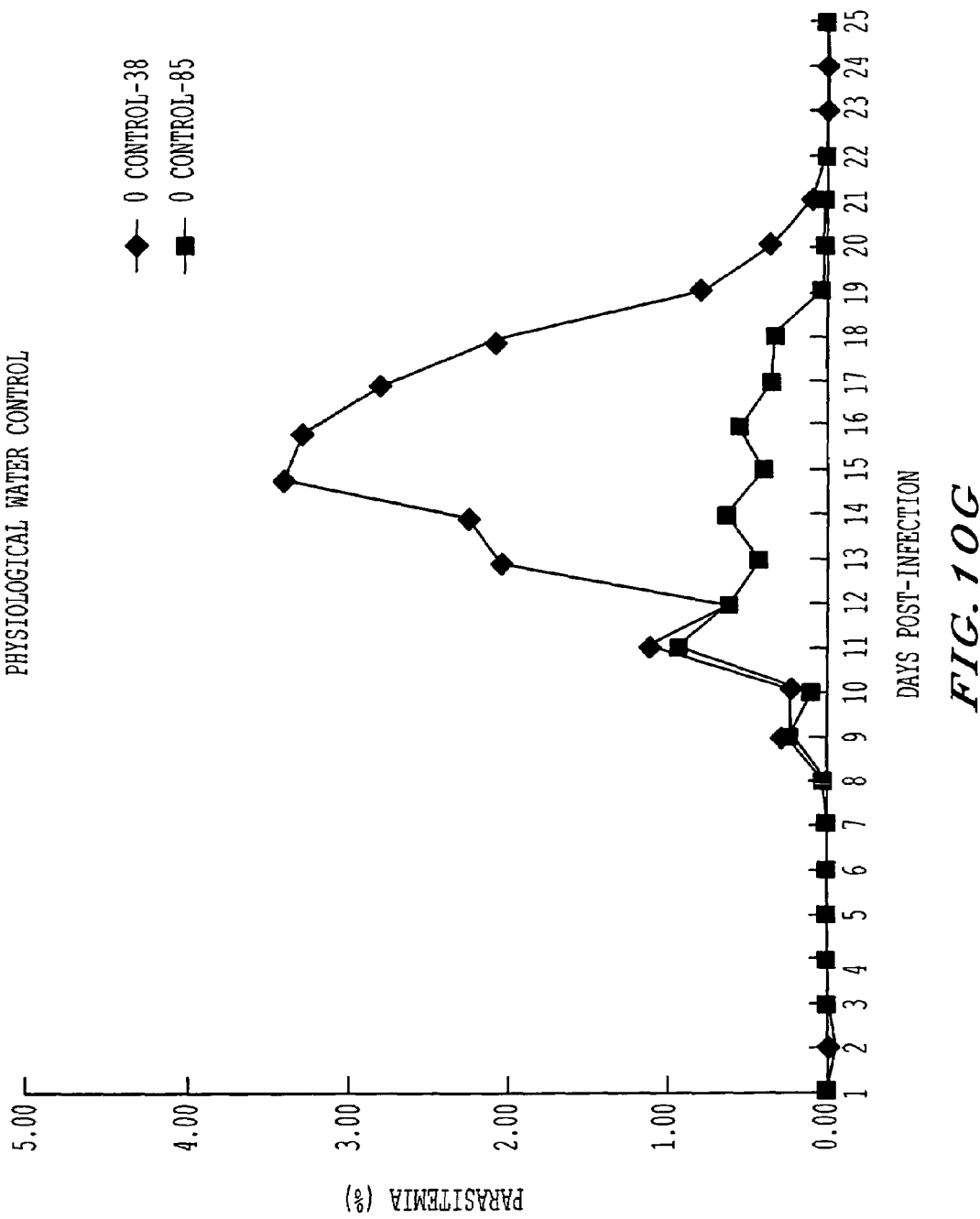

RECOMBINANT PROTEIN CONTAINING A C-TERMINAL FRAGMENT OF *PLASMODIUM* MSP-1

CROSS-REFERENCE TO RELATED APPLICATIONS

This application is a continuation of U.S. application Ser. No. 09/125,031, filed Mar. 10, 1999, which is now U.S. Pat. No. 6,958,235, and which is a 371 application of PCT/FR97/00290 filed Feb. 14, 1997, which claims priority to French patent application 96/01822 filed Feb. 14, 1996.

BACKGROUND OF THE INVENTION

1. Field of the Invention

The invention relates to novel active principles for vaccines derived from the major surface protein in merozoite forms of a *Plasmodium* which is infectious for mammals, especially humans, more generally termed MSP-1.

2. Discussion of the Background

MSP-1 has already been the subject of a number of studies. It is synthesised in the schizont stage of *Plasmodium* type parasites, in particular *Plasmodium falciparum*, and is expressed in the form of one of the major surface constituents of merozoites both in the hepatic stage and in the erythrocytic stage of malaria (1, 2, 3, 4). Because of the protein's predominant character and conservation in all known *Plasmodium* species, it has been suggested that it could be a candidate for constituting anti-malarial vaccines (5, 6).

The same is true for fragments of that protein, particularly the natural cleavage products which are observed to form, for example during invasion by the parasite into erythrocytes of the infected host. Among such cleavage products are the C-terminal fragment with a molecular weight of 42 kDa (7, 8) which is itself cleaved once more into an N-terminal fragment with a conventional apparent molecular weight of 33 kDa and into a C-terminal fragment with a conventional apparent molecular weight of 19 kDa (9) which remains normally fixed to the parasite membrane after the modifications carried out on it, via glycosylphosphatidylinositol (GPI) groups (10, 11).

It is also found at the early ring stage of the intraerythrocytic development cycle (15, 16), whereby the observation was made that the 19 kDa fragment could play a role which is not yet known, but which is doubtless essential in re-invasive processes. This formed the basis for hypotheses formed in the past that that protein could constitute a particularly effective target for possible vaccines.

It should be understood that the references frequently made below to the p42 and p19 proteins from a certain type of *Plasmodium* are understood to refer to the corresponding C-terminal cleavage products of the MSP-1 protein of that *Plasmodium* or, by extension, to products containing substantially the same amino acid sequences, obtained by genetic recombination or by chemical synthesis using conventional techniques, for example using the "Applied System" synthesiser, or by "Merrifield" type solid phase synthesis. For convenience, references to "recombinant p42" and "recombinant p19" refer to "p42" and "p19" obtained by techniques comprising at least one genetic engineering step.

Faced with the difficulty of obtaining large quantities of parasites for *P. falciparum* and the impossibility of cultivating *P. vivax* in vitro, it has become clear that the only means of producing an anti-malaria vaccine is to resort to techniques which use recombinant proteins or peptides. However, MSP-1 is very difficult to produce whole because of it large size of about 200 kDa, a fact which has led researchers to study the C-terminal portion, the (still unknown) function of which is probably the more important.

Recombinant proteins concerning the C-terminal portion of the *P. falciparum* MSP-1 which have been produced and tested in the monkey (12, 40, 41) are:

- a p19 fused with a glutathione-S-transferase produced in *E. coli* (40);
- a p42 fused with a glutathione-S-transferase produced in *E. coli* (12);
- a p19 fused with a polypeptide from a tetanic anatoxin carrying auxiliary T cell epitopes produced in *S. cerevisiae* (12);
- a p42 product in a baculovirus system (41).

A composition containing a p19 protein fused with a glutathione-S-transferase produced in *E. coli* combined with alum or liposomes did not exhibit a protective effect in any of six vaccinated *Aotus nancymai* monkeys (40).

A composition containing a p42 protein fused with a glutathione-S-transferase produced in *E. coli* combined with a Freund complete adjuvant did not exhibit a protective effect in two types of *Aotus* monkeys (*A. nancymai* and *A. vociferans*) when administered to them. The p19 protein produced in *S. cerevisiae* exhibited a protective effect in two *A. nancymai* type *Aotus* monkeys (12). In contrast, there was no protective effect in two *A. vociferans* type *Aotus* monkeys.

Some researchers (Chang et al.) have also reported immunisation tests carried out in the rabbit using a recombinant p42 protein produced in a baculovirus system and containing one amino acid sequence in common with *P. falciparum* (18). Thus these latter authors indicate that in the rabbit that recombinant p42 behaves substantially in the same way as the entire recombinant MSP-1 protein (gp195). This p42 protein in combination with a Freund complete adjuvant has been the subject matter of a vaccination test in a non-human primate susceptible to infection by *P. falciparum, Aotus, lemurinus grisemembra* (40). The results showed that 2 of 3 animals were completely protected and the third, while exhibiting a parasitemia which resembled that of the controls, had a longer latent period. It is nevertheless risky to conclude to a protective nature in man of the antibodies thus induced against the parasites themselves. It should be remembered that there are currently no very satisfactory experimental models in the primate for *P. vivax* and *P. falciparum*. The *Saimiri* model, developed for *P. falciparum* and *P. vivax*, and the *Aotus* model for *P. falciparum*, are artificial systems requiring the parasite strains to be adapted and often requiring splenectomy of the animals to obtain significant parasitemia. As a result, the vaccination results from such models can only have a limited predictive value for man.

In any event, what the real vaccination rate would be which could possibly be obtained with such recombinant proteins is also questionable, bearing in mind the discovery—reported below—of the presence in p42s from *Plasmodiums* of the same species, and more particularly in the corresponding p33s, of hypervariable regions which would in many cases render uncertain the immunoprotective efficacy of antibodies induced in individuals vaccinated with a p42 from a *Plasmodium* strain against an infection by other strains of the same species (13).

It can even be assumed that the high polymorphism of the N-terminal portion of p42 plays a significant role in immune escape, often observed for that type of parasite.

The aim of the present invention is to produce vaccinating recombinant proteins which can escape these difficulties, the protective effect of which is verifiable in genuinely significant experimental models or even directly in man.

More particularly, the invention provides vaccinating compositions against a *Plasmodium* type parasite which is infectious for man, containing as an active principle a recombinant protein which may or may not be glycosylated, whose essential constituent polypeptide sequence is:

either that of a 19 kilodalton (p19) C-terminal fragment of the surface protein 1 of the merozoite form (MSP-1 protein) of a *Plasmodium* type parasite which is infectious for man, said C-terminal fragment remaining normally anchored to the parasite surface at the end of its penetration phase into human erythrocytes in the event of an infectious cycle;

or that of a portion of that fragment which is also capable of inducing an immune response which can inhibit in vivo parasitemia due to the corresponding parasite;

or that of an immunologically equivalent peptide of said p19 fragment or said portion of that fragment; and said recombinant protein further comprises conformational epitopes which are unstable in a reducing medium and which preferably constitute the majority of the epitopes recognised by human antiserums formed against the corresponding *Plasmodium*.

BRIEF DESCRIPTION OF THE DRAWINGS

FIG. 1A illustrates the nucleotide and amino acid sequences of the synthetic gene (Bac 19) and the "native gene" (PF19) of *P. falciparum* described by Chang et al;

FIG. 1B illustrates the nucleotide and amino acid sequences of the synthetic gene (Bac 19) and the "native gene" (PF19) of the Uganda Palo Alto isolate of *P. falciparum*;

FIG. 1C illustrates the PfMSP1$_{P19}$A recombinant protein sequence before cutting out the signal;

FIG. 1D illustrates the PfMSP1$_{P19}$A recombinant protein after cutting out the signal sequence;

FIG. 6G is the data obtained to produce the graphs in FIGS. 6A to 6F;

FIG. 8D is the data obtained to produce the graphs of FIGS. 8A to 8C;

FIG. 9B is a graph illustrating the percent parasitemia versus days post infection of 2 macaques immunized with recombinant p19 and alum;

FIG. 9E is the data obtained to generate the graphs in FIGS. 9A to 9D;

FIG. 10B is a graph illustrating the percent parasitemia versus days post infection in a squirrel monkey immunized with MSP-1 p19 and Freunds;

FIG. 10G is a graph illustrating the percent parasitemia versus days post infection in a squirrel monkey immunized with physiological water as the control.

DETAILED DESCRIPTION OF THE PREFERRED EMBODIMENTS

Figure 2A:
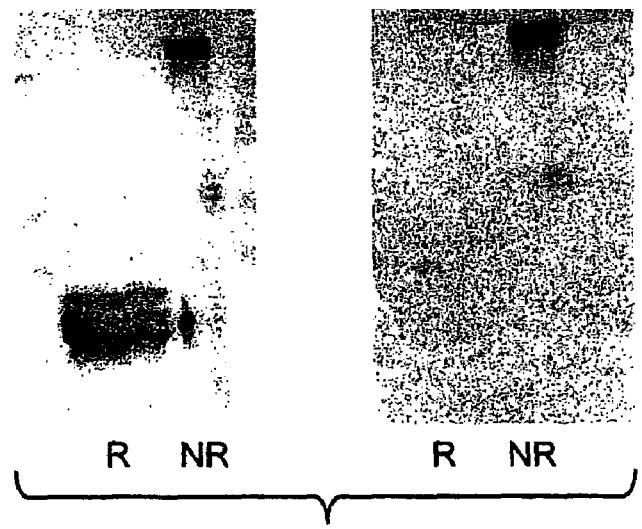
FIG. 2A is an immunoblot using SDS-PAGE of the soluble recombinant PfMSP1$_{P19}$ antigen purified by immunoaffinity of the presence (reduced) or absence (non-reduced) of -mercaptoethanol.

The presence of such conformational epitopes could play an important role in the protective efficacy of the active principle of the vaccines. They are particularly found in the active principles which exhibit the other characteristics defined above, when they are produced in a baculovirus system. If needs be, it is mentioned below that the expression "baculovirus vector system" means the ensemble constituted by the baculovirus type vector itself and the cell lines, in particular cells of insects transfectable by a baculovirus modified by a sequence to be transferred to these cell lines resulting in expression of that transferred sequence. Preferred examples of these two partners in the baculovirus system have been described in the article by Longacre et al. (19). The same system was used in the examples below. It goes without saying, of course, that variations in the baculovirus and in the cells which can be infected by the baculovirus can be used in place of those selected.

In particular, the recombinant protein is recognised by human antiserums formed against the corresponding *Plasmodium* or against a homologous *Plasmodium* when it is in its non reduced state or in a reduced non irreversible state, but is not recognised or is only recognised to a slight extent by these same antiserums when it is irreversibly reduced.

The unstable character of these conformational epitopes in a reducing medium can be demonstrated by the test described below in the examples, in particular in the presence of β-mercaptoethanol. Similarly, the examples below describe the experimental conditions applicable to obtain irreversible reduction of the proteins of the invention.

From this viewpoint, the recombinant protein produced by Longacre et al. (14) can be used in such compositions. It should be remembered that S. Longacre et al. succeeded in producing a recombinant p19 from the MSP-1 of *P. vivax* in a baculovirus vector system containing a nucleotide sequence coding for the p19 of *Plasmodium vivax*, in particular by transfecting cultures of insect cells [*Spodoptera frugiperda* (Sf9) line] with baculovirus vectors containing, under the control of the polyhedrin promoter, a sequence coding for the peptide sequences defined below, with the sequences being placed in the following order in the baculovirus vector used:
- a 35 base pair 5' terminal fragment of the polyhedrin signal sequence, in which the methionine codon for initiating expression of this protein had been mutated (to ATT);
- a 5'-terminal nucleotide fragment coding for a 32 amino acid peptide corresponding to the N-terminal portion of MSP-1, including the MSP-1 signal peptide;
- either a nucleotide sequence coding for p19, or a sequence coding for the p42 of the MSP-1 protein of *Plasmodium vivax*, depending on the case, these sequences also being provided with ("anchored" forms) or deprived of (soluble forms) 3' end regions of these nucleotide sequences, whose end C-terminal expression products are reputed to play an essential role in anchoring the final p19 protein to the parasite membrane;
- 2 TAA stop codons.

For p42, the sequences derived from the C-terminal region of MSP-1 extend consequently from amino acid Asp 1325 to amino acid Leu 1726 (anchored form) or to amino acid Ser 1705 (soluble form) and for p19, the sequences extend from amino acid Ile 1602 to amino acid Leu 1726 (anchored form) or to amino acid Ser 1705 (soluble form) it being understood that the complete amino acid sequences of p42 and p19, whose initial and terminal amino acids have been indicated above follow from the gene of the Belem isolate of *P. vivax* which has been sequenced (20).

Similar results were obtained using, in the same vector systems, nucleotide sequences coding for the p42 and p19 of *Plasmodium cynomolgi*. The interest in *P. cynomolgi* is twofold: it is a parasitic species very close to *P. vivax* which is infectious for the macaque. It can also infect man. Further, access to the natural hosts of *P. cynomolgi*, rhesus monkeys and toque macaques, is also possible, to test the efficacy of the protection of MSP-1 from *P. cynomolgi* in natural systems. The rhesus monkey is considered to be one of the most representative species for immune reactions in man.

In particular, excellent results have been obtained in vaccination tests carried out using the toque macaque with two recombinant polypeptides: soluble p42 and, in particular, soluble p19 derived from *P. cynomolgi*, respectively produced in a baculovirus system and purified on an affinity column with monoclonal antibodies recognising the corresponding regions of the native MSP-1 protein. The following observations were made: six monkeys immunised with only p19 (three monkeys) and the p19 and p42 together (three monkeys) all exhibited practically sterile immunity after challenge infection. The results obtained in the three monkeys immunised with p42 were less significant. Two of them were as above, but since the third exhibited a lower parasitemia than the controls immunised with a PBS buffer in the presence of Freund adjuvant (3 monkeys) or not immunised (3 monkeys), it was less clear.

A second challenge infection showed that the monkeys which had received p19 alone were protected for at least six months. A second vaccination test with p19 in combination with alum in this system (toque macaque *P. cynomolgi*) exhibited significant protection for 2 of the 3 monkeys. This is the first time that MSP-1 or another recombinant antigen has demonstrated a protective effect in the presence of alum (42).

The particularly effective test results carried out with the macaque with recombinant polypeptides produced in a baculovirus system using a recombinant p19 from *P. cynomolgi* showed that recombinant polypeptides respectively containing recombinant p19s from other *Plasmodiums* must behave in the same manner. They are more meaningful for malaria in man than the results from tests carried out with *P. vivax* or *P. falciparum* in their "artificial hosts".

Baculovirus recombinant proteins derived from a C-terminal MSP-1 portion (p19) have a very significant antimalarial protective effect in a natural system, which constitutes the most representative model for evaluating the protective effect of MSP-1 for man.

The protective effect obtained can be further improved if the p19 form is deprived of the hypervariable region of the N-terminal portion of p42, the effect of which can be deleterious in natural situations in which the vaccinated subject is confronted by a great deal of polymorphism. Further, p19 appears to possess specific epitopes which are not present in p42.

The 19 kDa C-terminal fragment, the sequence of which is present in the active principle of the vaccine, can be limited to the sequence for the p19 itself, in the absence of any polypeptide sequence normally upstream of the p19 sequence in the corresponding MSP-1 protein. Clearly, though, the essential constituent polypeptide sequence of the active principle can also comprise a polypeptide sequence for the C-terminal side belonging to the 33 kDa (p33) N-terminal fragment still associated with the p19 in the corresponding p42, before natural cleavage of the latter, if the presence of this fragment does not modify the immunological properties of the active principle of the vaccine. As will be seen below, in particular in the description of the examples, the C-terminal sequences of the p33 in various strains of the same species of *Plasmodium* (see the C-terminal portion of the peptide sequences of "region III" in FIG. 4 (SEQ ID NOS:11-14)) also have a degree of homology or substantial conservation of the sequence, for example on the order of at least 80%, in different varieties of *Plasmodiums* which are infectious for man, such that they do not fundamentally modify the vaccinating properties of the active principle (the sequence of which corresponds to region IV in FIG. 4), in particular using the hypothesis which follows from this figure; that the presumed cleavage site, between the p19 and region III of the p33 is located between the leucine and asparagine residues in a particularly well conserved region (LNVQTO) (SEQ ID NO:15).

Normally the C-terminal polypeptide sequence of the p33, when it is present, comprises less than 50 amino acid residues, or even less than 35, preferably less than 10 amino acid residues.

In contrast, the essential constituent polypeptide sequence of the active principle of the vaccine need not comprise all of the sequence coding for p19, naturally providing that the latter retains the ability to induce antibodies which protect against the parasite. In particular, the molecular weight of the "fragment portion" is 10 to 25 kDa, in particular 10 to 15 kDa. Preferably, this polypeptide fragment portion contains at least one of the two EGF (Epidermal Growth Factor) regions.

Clearly, the skilled person could distinguish between active fragments and those which would no longer be so, in particular experimentally by producing modified vectors containing inserts with different lengths originating from the p19, respectively isolated from the fragments obtained from the sequence coding for p19, by reaction with appropriate restriction enzymes, or by exonucleolytic enzymes which would be kept in contact with the fragment coding for p19 for differing periods; the capacity of the expression products from these inserts in the corresponding eukaryotic cells, in particular in insect cells, transformed by the corresponding modified vectors, to exert a protective effect can then be tested, in particular under the experimental conditions which are described below in the examples. In particular, the expression products of these inserts must be able to inhibit a parasitemia induced in vivo by the corresponding whole parasite.

Thus, the invention includes all vaccinating compositions in which the essential constituent polypeptide sequence of the active principle is constituted by a peptide which can induce a cellular and/or humoral type immunological response equivalent to that produced by p19 or a fragment as defined above, provided that the addition, deletion or substitution in the sequence of certain amino acids by others would not cause a large modification of the capacity of the modified peptide— hereinafter termed the "immunologically equivalent peptide"—to inhibit said parasitemia.

The p19 fragment can naturally also be associated at the N-terminal side or the C-terminal side or via a peptide bond to a further plasmoidal protein fragment having a vaccinating potential (such as Duffy binding protein from *P. vivax* (29) or EBA-175 from *P. falciparum* (30) and (31), one region of which is specifically rich in cysteine), provided that its capacity to inhibit parasitemia normally introduced in vivo by the corresponding parasite is not altered but is amplified.

Upstream of the N-terminal end of p19, the fragment coding for p19 or a portion thereof can also contain a peptide sequence which is different again, for example a C-terminal fragment of the signal peptide used, such as that for the MSP-1 protein. This sequence preferably comprises less than 50 amino acids, for example 10 to 40 amino acids.

These observations pertain in similar fashion to the p19s from other *Plasmodium*, in particular *P. falciparum*, the dominant species of the parasites, responsible for one of the most serious forms of malaria.

However, the techniques summarised above for producing a recombinant p19 from *P. vivax* or *P. cynomolgi* in a baculovirus system are difficult to transpose unchanged to producing a recombinant p19 of *P. falciparum* in a satisfactory yield, if only to obtain appreciable quantities which will allow immunoprotective tests to be carried out.

The invention also provides a process which overcomes this problem to a large extent. It also becomes possible to obtain much higher yields of *P. falciparum* p19—and other *Plasmodiums* where similar difficulties are encountered— using a synthetic nucleotide sequence substituting the natural nucleotide sequence coding for the p19 of *Plasmodium falciparum* in an expression vector of a baculovirus system, this synthetic nucleotide sequence coding for the same p19, but being characterized by a higher proportion of G and C nucleotides than in the natural nucleotide sequence.

In other words, the invention follows from the discovery that expression of a nucleotide sequence coding for a p19 in a baculovirus system is apparently linked to an improved compatibility of successive codons in the nucleotide sequence to express with the "cellular machinery" of the host cells transformable by the baculovirus, in the manner of that observed for the natural nucleotide sequences normally contained in these baculovirus and expressed in the infected host cells; hence the poor expression, or even total absence of expression of a native *P. falciparum* nucleotide sequence; hence also a possible explanation of the more effective expression observed by Longacre et al. (14) for the p19 of *P. vivax* in a baculovirus system and, as the inventors have also shown, of the *P. cynomolgi* sequence from corresponding native p19 nucleotide sequences, because of their relatively much higher amounts of G and C nucleotides than those of the native nucleotide sequences coding for the p19 of *P. falciparum*.

The invention thus more generally provides a recombinant baculovirus type modified vector containing, under the control of a promoter contained in said vector and able to be recognised by cells transfectable by said vector, a first nucleotide sequence coding for a signal peptide exploitable by a baculovirus system, characterized by a second nucleotide sequence downstream of the first, also under the control of the promoter and coding for the peptide sequence:

either of a 19 kilodalton (p19) C-terminal fragment of the surface protein 1 of the merozoite form (MSP-1 protein) of a *Plasmodium* type parasite other than *Plasmodium vivax* which is infectious for man, said C-terminal fragment remaining normally anchored to the parasite surface at the end of its penetration phase into human erythrocytes in the event of an infectious cycle;

or of a portion of that peptide fragment provided that the expression product from the second sequence in a baculovirus system is also capable of inducing an immune response which can inhibit in vivo parasitemia due to the corresponding parasite;

or of an immunologically equivalent peptide of said C-terminal peptide fragment (p19) or said peptide fragment portion by addition, deletion or substitution of amino acids not resulting in a large modification of the capacity of said immunologically equivalent peptide to induce a cellular and/or humoral type immunological response similar to that produced by said p19 peptide fragment or said portion of said fragment; and said nucleotide sequence having, if necessary, a G and C nucleotide content in the range 40% to 60%, preferably at least 50%, of the totality of the nucleotides from which it is constituted. This sequence can be obtained by constructing a synthetic gene in which the natural codons have been changed for codons which are rich in G/C without modifying their translation (maintaining the peptide sequence).

The nucleotide sequence, provided by a synthetic DNA, may have at least 10% of modified codons with respect to the natural gene sequence or cDNA while retaining the characteristics of the natural translated sequence, i.e., maintaining the amino acid sequence.

It is not excluded that this G and C nucleotide content could be further increased provided that the modifications resulting therefrom as to the amino acid sequence of the recombinant peptide—or immunologically equivalent peptide—produced do not result in a loss of immunological properties, or protective properties, of the recombinant proteins formed, in particular in the tests which will be described below.

These observations naturally apply to other *Plasmodium* which are infectious for man, in particular those where the native nucleotide sequences coding for corresponding p19s would have T and A nucleotide contents which are poorly compatible with effective expression in a baculovirus system.

The sequence coding for the signal used can be that normally associated with the native sequence of the *Plasmodium* concerned. But it can also originate from another *Plasmodium*, for example *P. vivax* or *P. cynomolgi* or another organism if it can be recognised as a signal in a baculovirus system.

The sequence coding for p19 or a fragment thereof in the vector under consideration is, in one case, deprived of the anchoring sequence of the native protein to the parasite from which it originates, in which case the expressed protein is generally excreted into the culture medium (soluble form). It is also remarkable in this respect that under the conditions of the invention, the soluble and anchored forms of the recombinant proteins produced, in particular when they are from *P. falciparum* or *P. cynomolgi* or *P. vivax*, tend to form oligomers, this property possibly being at the origin of the increased immunogenicity of the recombinant proteins formed.

The invention also concerns vectors in which the coding sequence contains the terminal 3'end sequence coding for the hydrophobic C'-terminal end sequence of the p19 which is normally implicated in the induction of anchoring the native protein to the cell membrane of the host in which it is expressed. This 3'-terminal end region can also be heterologous as regards the sequence coding for the soluble p19 portion, for example corresponding to the 3'-terminal sequence from *P. vivax* or from another organism when it codes for a sequence which anchors the whole of the recombinant protein produced to the cell membrane of the host of the baculovirus system used. An example of such anchoring sequences is the GPI of the CD59 antigen which can be expressed in the cells of *Spodoptera frugiperda* (32) type insects or the GPI of a CD14 human protein (33).

The invention also, naturally, concerns recombinant proteins, these proteins comprising conformational epitopes recognised by human serums formed against the corresponding *Plasmodium*.

In general, the invention also concerns any recombinant protein of the type indicated above, provided that it comprises conformational epitopes such as those produced in the baculovirus system, in particular those which are unstable in a reducing medium.

The invention also, naturally, concerns said recombinant proteins, whether they are in their soluble form or in the form provided with an anchoring region, in particular to cellular hosts used in the baculovirus system.

The invention also encompasses oligomers spontaneously produced in the baculovirus systems used or produced a posteriori, using conventional protein oligomerisation techniques. The most commonly used technique involves glutaraldehyde. However, any conventional system for bridging between the respective amine and carboxyl functions in proteins can be used. As an example, any of the techniques described in European patent application EP-A-0 602 079 can be used.

The term "oligomer" means a molecule containing 2 to 50 monomer units, each of the monomer units containing p19 or a fragment thereof, as defined above, capable of forming an aggregate. The invention also encompasses any conjugation product between a p19 or a p19 fragment as defined above, and a carrier molecule—for example a polylysine-alanine—for use in producing vaccines, via bonds which are covalent or otherwise. The vaccinating compositions using them also form part of the invention.

The invention still further concerns vaccine compositions using these oligomeric or conjugated recombinant proteins, including proteins from *Plasmodium vivax*, these observations also extending to oligomers of these recombinant proteins.

The invention also encompasses compositions in which the recombinant proteins defined above are associated with an adjuvant, for example an alum. Recombinant proteins containing the C-terminal end region allowing them to anchor to the membrane of the cells in which they are produced are advantageously used in combination with lipids which can form liposomes appropriate to the production of vaccines. Without being limiting, lipids described, for example, in the publication entitled "Les liposomes aspects technologique, biologique et pharmacologique" [Liposomes: technological, biological and pharmacological aspects] by J. Delattre et al., INSERM, 1993, can be used.

The presence of the anchoring region in the recombinant protein, whether it is a homologous or heterologous anchoring region as regards the vaccinating portion proper, encourages the production of cytophilic antibodies, in particular $IgG_{2a}$ and $IgG_{2b}$ type in the mouse which could have a particularly high protective activity, so that associating the active principles of the vaccines so constituted with adjuvants other than the lipids used to constitute the liposome forms could be dispensed with. This amounts to a major advantage, since liposomes can be lyophilised under conditions which enable them to be stored and transported, without the need for chains of cold storage means.

Other characteristics of the invention will become clear from the following description of examples of recombinant proteins of the invention and the conditions under which they can be produced. These examples are not intended to limit the scope of the invention.

Description of the Construction of $PfMSP1_{p19}S$
(Soluble) (Soluble p19 from *P. falciparum*)

The recombinant construction $PfMSP1_{p19}S$ contains the DNA corresponding to 8 base pairs of the leader sequence and the first 32 amino acids of the MSP-1 of *Plasmodium vivax* from $Met_1$ to $Asp_{32}$ (Belem isolate; Del Portillo et al., 1991, P. N. A. S., 88, 4030) followed by GluPhe due to the EcoR1 site connecting the two fragments. This is followed by the synthetic gene described in FIG. 1, coding the *Plasmodium falciparum* $MSP1_{p19}$ from $Asn_{1613}$ to $Ser_{1705}$ (Uganda-Palo Alto isolate; Chang et al., 1988, Exp. Parasitol., 67, 1). The construction is terminated by two TAA stop codons. This construction gave rise to a recombinant protein which was secreted in the culture supernatant from infected cells.

In the same manner and for comparison, a recombinant construction was produced under conditions which were similar to those used to produce the p19 above, but working with a coding sequence consisting of a direct copy of the corresponding DNA of the *P. falciparum* strain (FUP) described by Chang et al., Exp. Parasit. 67, 1; 1989. The natural gene copy (from asparagine 1613 to serine 1705) was formed from the native gene by PCR.

FIG. 1A shows the sequences of both the synthetic gene (Bac19) (SEQ ID NO:1) and the "native gene" (PF19) (SEQ ID NO:3).

It can be seen that 57 codons of the 93 codons of the native sequence coding for the p19 from *P. falciparum* were modified (the third nucleotide in 55 of them and the first and third nucleotides in the other 2 codons). New codons were added to the 5' end to introduce the peptide signal under the conditions indicated above and to introduce an EcoRI site for cloning, and similarly two stop codons were added which were not present in the *P. falciparum* p19 to obtain expression termination signals. The individual letters placed above successive codons correspond to the respective successive amino acids. Asterisks (*) show the stop codons. Vertical lines indicate the nucleotides which are the same in the two sequences Description of the PfMSP1$_{p19}$A Construction (Anchored GPI) (Anchored p19 of *P. falciparum*)

The PfMSP1p19A construction had the characteristics of that above except that the synthetic sequence (FIG. 1B) (SEQ ID NOS: 4 and 6) codes for the MSP1p19 of *Plasmodium falciparum* (Uganda-Palo Alto Isolate) from Asn1513 to Ile1726 followed by two TAA stop codons. This construction gave rise to a recombinant protein which was anchored in the plasma membrane of infected cells by a glycosyl phosphatidyl inositol (GPI) type structure.

FIG. 1C represents the PfMSP1p19S recombinant protein sequence before cutting out the signal sequence (SEQ ID NO:7).

FIG. 1D represents the PfMSP1$_{p19}$S recombinant protein sequence after cutting out the signal sequence.

The amino acids underlined in FIGS. 1C and 1D originate from the EcoR1 site used to join the nucleotide sequences derived from the N-terminal portion of the MSP-1 of *P. vivax* (with signal sequence) (SEQ ID NO:9) and the MSP-1p19 of *P. falciparum*.

Figure 2B:
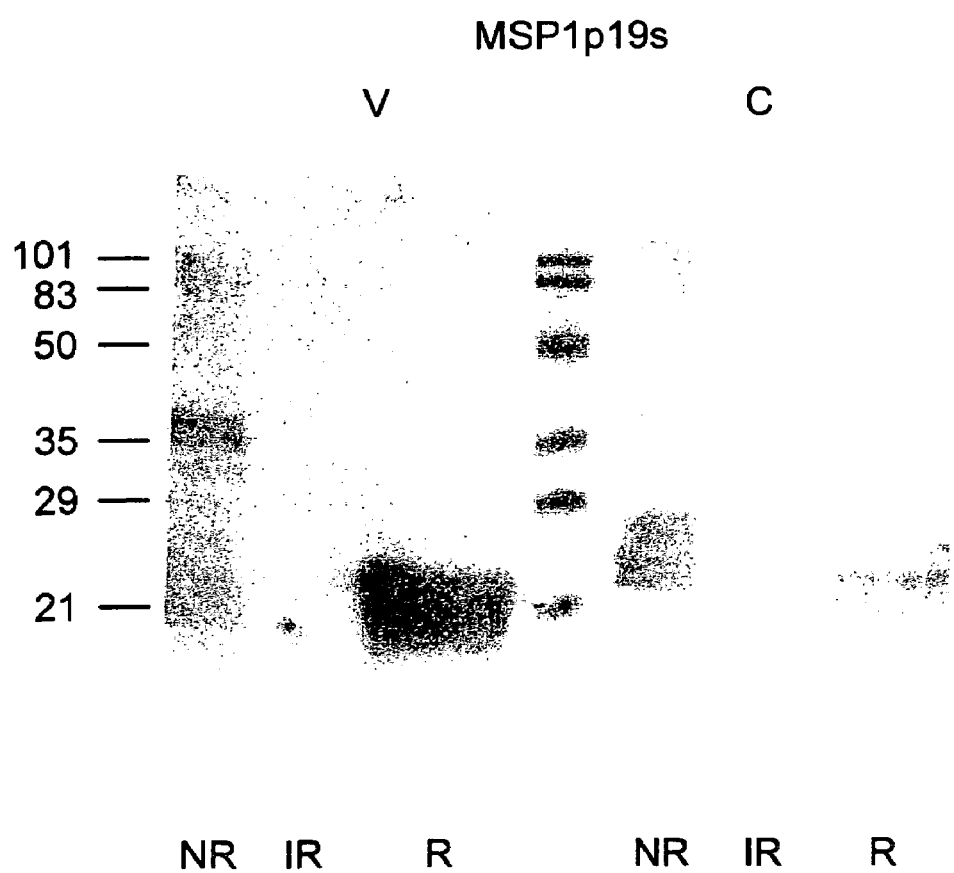
FIG. 2B is an immunoblot with human antiserum of recombinant purified MSP-1 P19 from *P. vivax* and *P. cynomolgi* under non-reduced (NR), reduced only in the charging medium (R) and irreversibly reduced (IR) conditions.

FIG. 2—The soluble recombinant PfMSP1$_{p19}$ antigen purified by immunoaffinity was analysed by immunoblot using SDS-PAGE in the presence (reduced) or absence (non reduced) of β-mercaptoethanol. Samples were charged onto gel after heating to 95° C. in the presence of 2% SDS. Under these conditions only covalent type bonds (disulphide bridges) can resist disaggregation. The left hand blot was revealed with a monoclonal antibody which reacted with a linear epitope of natural p19. The right hand blot was revealed with a mixture of 13 human antisera originating from subjects with acquired immunity to malaria due to *Plasmodium falciparum*. These results show that the recombinant baculovirus molecule can reproduce conformational epitopes in the form of a polymer the majority of which are recognised by human antiserum.

FIG. 2B

Immunoblot Analysis with Human Antiserum of Recombinant Purified MSP-1 p19 from *P. vivax* and *P. cynomolgi* Under Non Reduced (NR), Reduced Only in the Charging Medium (R) and Irreversibly Reduced (IR) Conditions This work was based on the idea that the baculovirus expression system correctly reproduced the conformational epitopes present in vivo on the C-terminal portion of MSP-1 in large amounts. The best means of measuring this property (which may be the only possible means in the absence of native purified proteins corresponding to p19) was to study the reactivity of the recombinant proteins with the antiserum of individuals exposed to malaria, this reflecting the native proteins as "seen" by the human immune system.

Thus soluble recombinant PvMSP-1 p19 and PcMSP-1 p19 antigens purified by immunoaffinity were analysed by immunoblot using SDS-PAGE (15%) in the presence (reduced) or absence (non reduced) of DTT. Samples were charged onto gel after heating to 95° C. in the presence of 2% SDS. The irreversible reduction was carried but as follows: the protein was resuspended in 0.2 M Tris-HCl, pH 8.4, 100 mM DTT, 1.0% SDS and heated for 30 minutes at 70° C. After diluting with water, acrylamide was added to a final concentration of 2 M and the mixture was incubated under nitrogen in the dark for 1 hour at 37° C. The immunoblot was revealed with a mixture of 25 human antisera originating from subjects with an acquired immunity to malaria due to *Plasmodium vivax*. V and C respectively designate proteins derived from the MSP-1 of *P. vivax* and *P. cynomolgi*. It should be noted that irreversibly reduced recombinant proteins exhibited no reactivity with human antiserum while non irreversibly reduced proteins or non reduced proteins exhibited good reactivity. (The non reduced Pv MSP-1 p19 was a little weak since in its glycosylated state it does not bind well to nitrocellulose paper). These results show that recognition of baculovirus MSP-1 p19 molecules by human antiserum is largely if not completely dependent on conformational epitopes sensitive to reduction which are reproduced in this system.

Figure 3A:
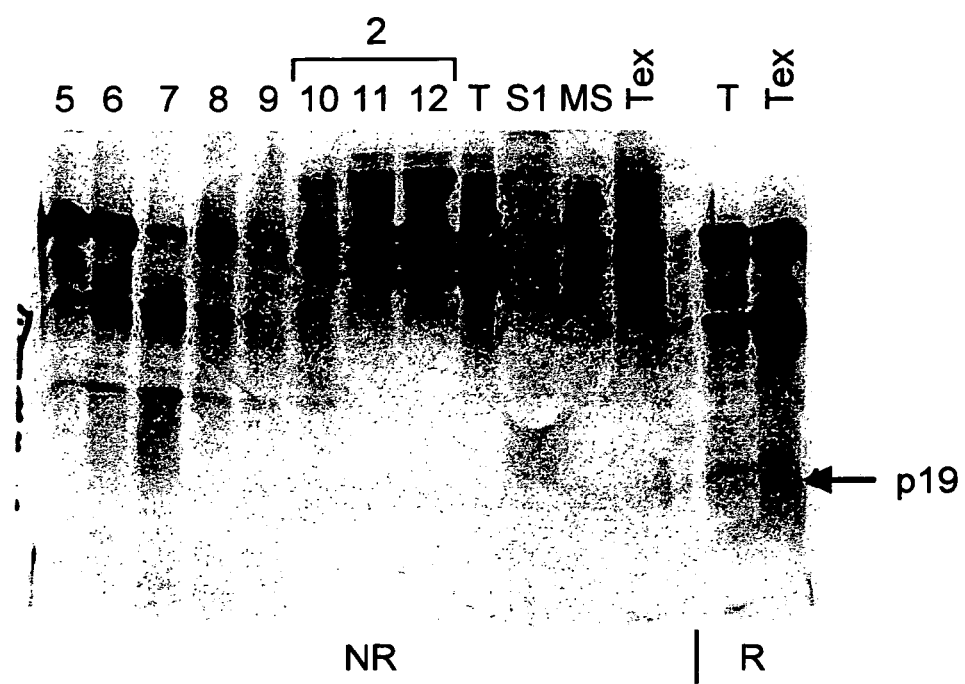
FIG. 3A is an immunoblot of the soluble PvMSP1$_{P42}$ recombinant antigen in the presence of protein fractions derived from merzoites of *P. falciparum* and separately isoelectric focusing in the presence (reduced) or absence (non-reduced) of -mercaptoethanol.
Figure 3B:
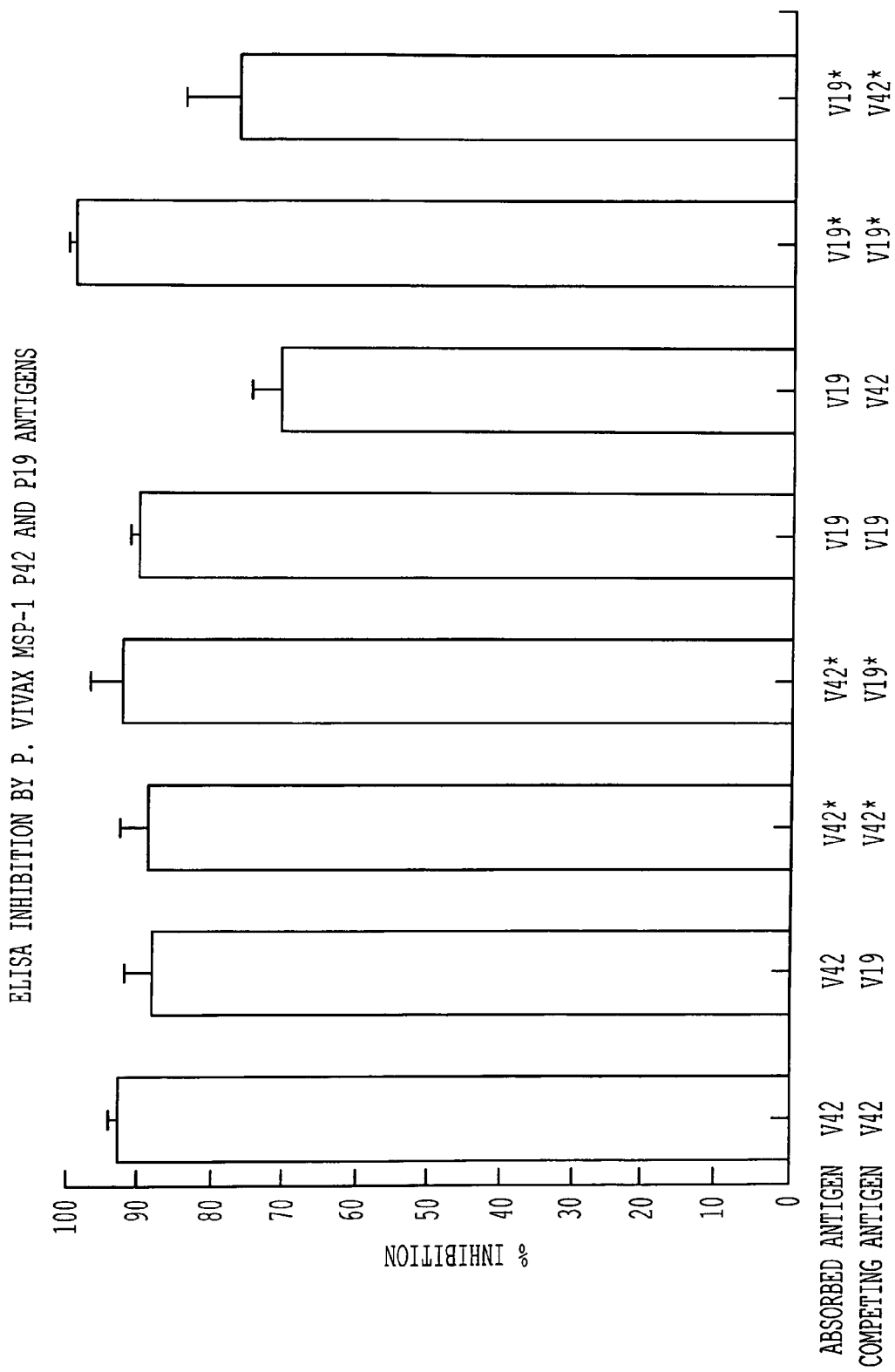
FIG. 3B is a graph illustrating the results of an ELISA inhibition technique of *P. vivax* MSP-1 P42 and P19 antigens by the antiserum of individuals with an acquired immunity to *P. vivax*.

FIG. 3—The soluble PvMSP1$_{P42}$ recombinant antigen (Longacre et al., 1994, op. Cit.) was incubated for 5 hours at 37° C. in the presence of protein fractions derived from merozoites of *P. falciparum* and separated by isolectrofocussing. The samples were then analysed by immunoblot in the presence (reduced) or absence (non reduced) of β-mercaptoethanol. Isolectrofocussing fractions 5 to 12, and two total merozoite extracts made in the presence (Tex) or absence (T) of detergent, were analysed. The immunoblot was revealed with monoclonal antibodies specific for MSP1$_{p42}$ and $_{p19}$ of *P. vivax*. The results suggest that there is a proteolytic activity in the *P. falciparum* merozoites which can be extracted with detergent. Digestion of p42 in certain fractions appear to cause polymerisation of the digestion products (p19); this polymerisation is probably linked to the formation of disulphide bridges since in the presence of β-mercaptoethanol, the high molecular weight forms disappear in favour of a molecule of about 19 kDa (Tex-R). The p19 polymerisation observed in these experiments could thus be an intrinsic property of this molecule in vivo.

FIG. 3B

The Differential Contribution of p42 and p19 Antigens to the P. vivax Anti-MSP-1 Human Response Recognition of P. vivax MSP-1 p42 and p19 antigens by the antiserum of individuals with an acquired immunity to P. vivax was compared using the ELISA inhibition technique as follows: a mixture of 25 human antisera originating from subjects with an acquired immunity to malaria due to P. vivax was diluted to 1:5000 and incubated for 4 hours at ambient temperature either alone, or in the presence of a 1 mM purified P. vivax recombinant p42 or p19. This mixture was transferred to a microliter well which had been coated for 18 hours at 4 [deg.] C. with 500 ng.ml <–1> of purified absorbed recombinant p42 or p19, and incubated for 30 minutes at ambient to temperature. After washing with PBS containing 0.1% of Tween 20, a goat anti-mouse IgG conjugated with peroxidase was added and the mixture was incubated for 1 hour at 37 [deg.] C. The enzymatic activity was revealed by reading the optical density at 492 nm. The percentage inhibition was calculated based on values of 100% of antiserum activity with the coated antiserum on the microtiter plate in the absence of a competing antigen. Statistical data were calculated using a Statview program. Each bar represents the average percentage inhibition of a pair of competing/absorbed antigens based on 4 to 12 determinations; the vertical lines correspond to a 95% confidence interval. Asterisks (*) designate the antigens produced in the presence of tunicamycin, thus with no N-glycosylation. The important parameters of these measurements were the dilution of the antiserum by 1:5000 which is in the region which is sensitive to ELISA curves and the competing antigen concentrations of 1 mM which includes competition by low affinity epitopes. Thus these data reflect the maximum resemblance between the two compared antigens. The results show that the majority, if not all of the p42 epitopes recognized by the human antiserum are present on the p19 since in the presence of the latter, the reactivity of the human antiserum against p42 is inhibited as much as by the p42 antigen itself. In contrast, however, about 20% of the p19 epitopes recognized by human antiserum were not or were not accessible on the p42, since the reactivity of the human antiserum against the p19 was much less inhibited by p42 than by p19 itself. Such specific epitopes of p19 could be constituted or revealed only after cleaving the p42 into p19 and p33. These results were not affected by glycosylation showing that the effect is really due to a difference between the peptide components of p19 and p42 and not to a difference in glycosylation. These results underline the fact that p19 has a distinct immunological identity compared to p42.

Description of the PcMSP1$_{p19}$S (Soluble) Construction (Soluble p19 of P. cynomolgi)

The DNA used for the above construction was obtained from a clone of the Plasmodium cynomolgi ceylonesis strain (22-23). This strain had been maintained by successive passages through its natural host (Macaca sinica) and cyclic transmissions via mosquitoes (27).

Blood parasites in the mature schizont stage were obtained from infected monkeys when the parasitemia had attained a level of 5%. They were then purified using the methods described in (25). The DNA was then extracted as described in (26).

Figure 4A.1:
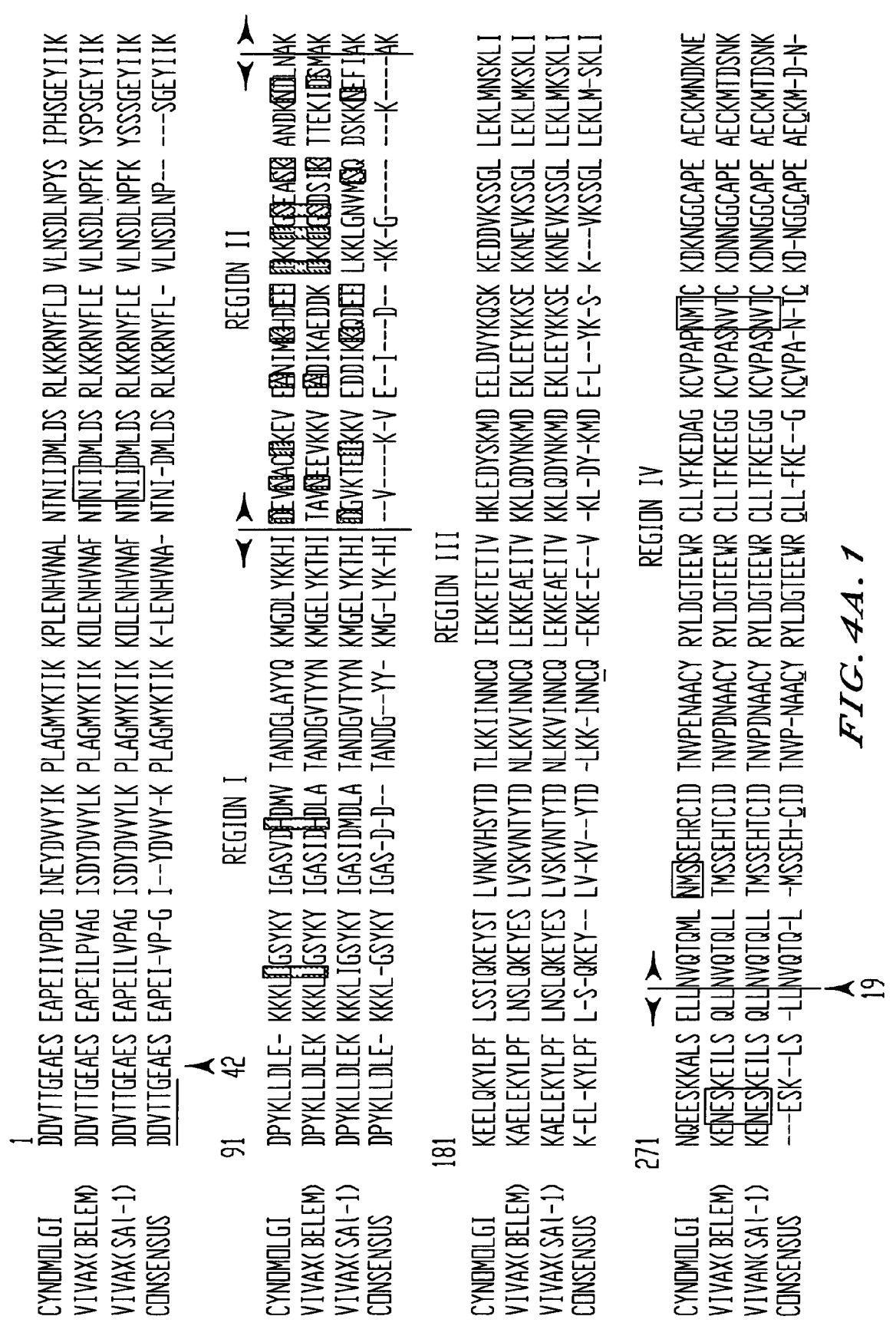
Figure 4B:
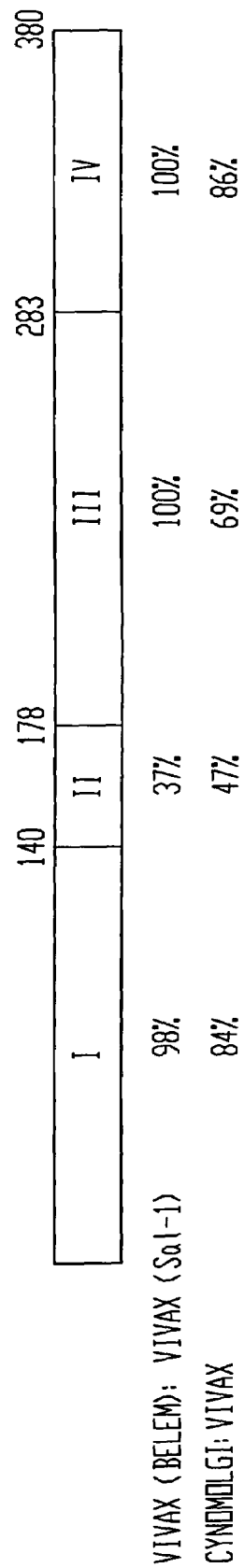
FIG. 4 are nucleotide sequences. The underlines oligonucleotides originate from *P. vivax* and are used as primers in a PCR reaction. The lower portion of FIG. 4 illustrates the percent identity between two isolates of *P. vivax* and *P. cynomolgi*.

A 1200 base pair fragment was produced using a PCR reaction using the oligonucleotides underlined in FIG. 4 originating from P. vivax. The 5' oligonucleotide comprised an EcoRI restriction site and the 3' oligonucleotide comprised two synthetic TAA stop codons followed by a BglII restriction site. This fragment was introduced by ligation and via these EcoRI and BglII sites into the pVLSV$_{200}$ plasmid already containing the signal sequence for the MSP-1 protein of P. vivax (19). The new plasmid (pVLSV$_{200}$C$_{42}$) was used to analyse the DNA sequences.

The P. cynomolgi and the corresponding P. vivax sequences were aligned. The black arrows designate the presumed primary and secondary cleavage sites. They were determined by analogy with known sites in P. falciparum (27, 28). The vertical lines and horizontal arrows localise the limits of the four regions which were studied. Region 4 corresponded to the sequence coding for the P. cynomolgi p19. Glycosylation sites are boxed and the preserved cysteines are underlined. The lower portion of FIG. 4 shows the percentage identity between the two isolates of P. vivax and P. cynomolgi.

The recombinant construction PcMSP1$_{p19}$S contains the DNA corresponding to 8 base pairs of the leader sequence and the first 32 amino acids of the MSP-1 of Plasmodium vivax from Met$_1$ to Asp$_{32}$ (Belem isolate; Del Portillo et al., 1991, P. N. A. S., 88, 4030) followed by GluPhe, due to the EcoR1 site, connecting the two fragments. This is followed by the sequence coding for the Plasmodium cynomolgi MSP1$_{p19}$ from Lys$_{276}$ to Ser$_{380}$ (Ceylon strain). The construction was terminated by two TAA stop codons. This construction gave rise to a recombinant protein which was secreted in the culture supernatant of infected cells.

Purification of Recombinant PfMSP1$_{p19}$ Protein by Immunoaffinity Chromatography with a Monoclonal Antibody Specifically Recognising the p19 of Plasmodium falciparum The chromatographic resin was prepared by binding 70 mg of a monoclonal antibody (obtained from a G17.12 hybridoma deposited at the CNCM [National Collection of Microorganism Cultures] (Paris, France) on the 14 Feb. 1997, registration number I-1846; this G17.12 hybridoma was constructed from X63 Ag8 653 myeloma producing IgG 2a/k recognising the P. falciparum p19) to 3 g of activated CNBr-Sepharose 4B (Pharmacia) using standard methods detailed in the procedure employed by Pharmacia. The culture supernatants containing the soluble PfMSP1p19 were batch incubated with the chromatographic resin for 16 hours at 4° C. The column was washed once with 20 volumes of 0.05% NP40, 0.5 M of NaCl, PBS; once with 5 volumes of PBS and once with 2 volumes of 10 mM of sodium phosphate, pH 6.8. Elution was carried out with 30 ml of 0.2 M glycine, pH 2.2. The eluate was neutralised with 1 M sodium phosphate, pH 7.7 then concentrated by ultrafiltration and dialysed against PBS. To purify the anchored PfMSP1p19, all of the washing and elution solutions contained a supplemental 0.1% of 3-(dimethyl-dodecylammonio)-propane sulphonate (Fluka).

Recombinant Plasmodium vivax (p42 and p19) MSP1 Vaccination Test in the Squirrel Monkey Saimiri sciureus This vaccination test was carried out on male non splenectomised 2 to 3 year old Saimiri sciureus boliviensis monkeys. Three monkeys were injected 3 times intramuscularly at 3 week intervals with a mixture of about 50 to 100 µg each of recombinant soluble PvMSP1$_{p42}$ and $_{p19}$ (19), purified by immunoaffinity. Complete and incomplete Freund adjuvant was used as follows: $1^{st}$ injection: 1:1 FCA/FIA; $2^{nd}$ injection: 1:4 FCA/FIA; $3^{rd}$ injection: FIA. These adjuvant compositions were then mixed 1:1 with the antigen in PBS. Five control monkeys received the glutathione-S-transferase (GST) antigen produced in *E. coli* using the same protocol. The challenge infection was carried out by injecting $2\times10^6$ red blood cells infected with an adapted *Plasmodium vivax* strain (Belem) 2.5 weeks after the final injection. The protection was evaluated by determining parasitemia daily in all animals by examining smears stained with Giemsa.

Figure 5:
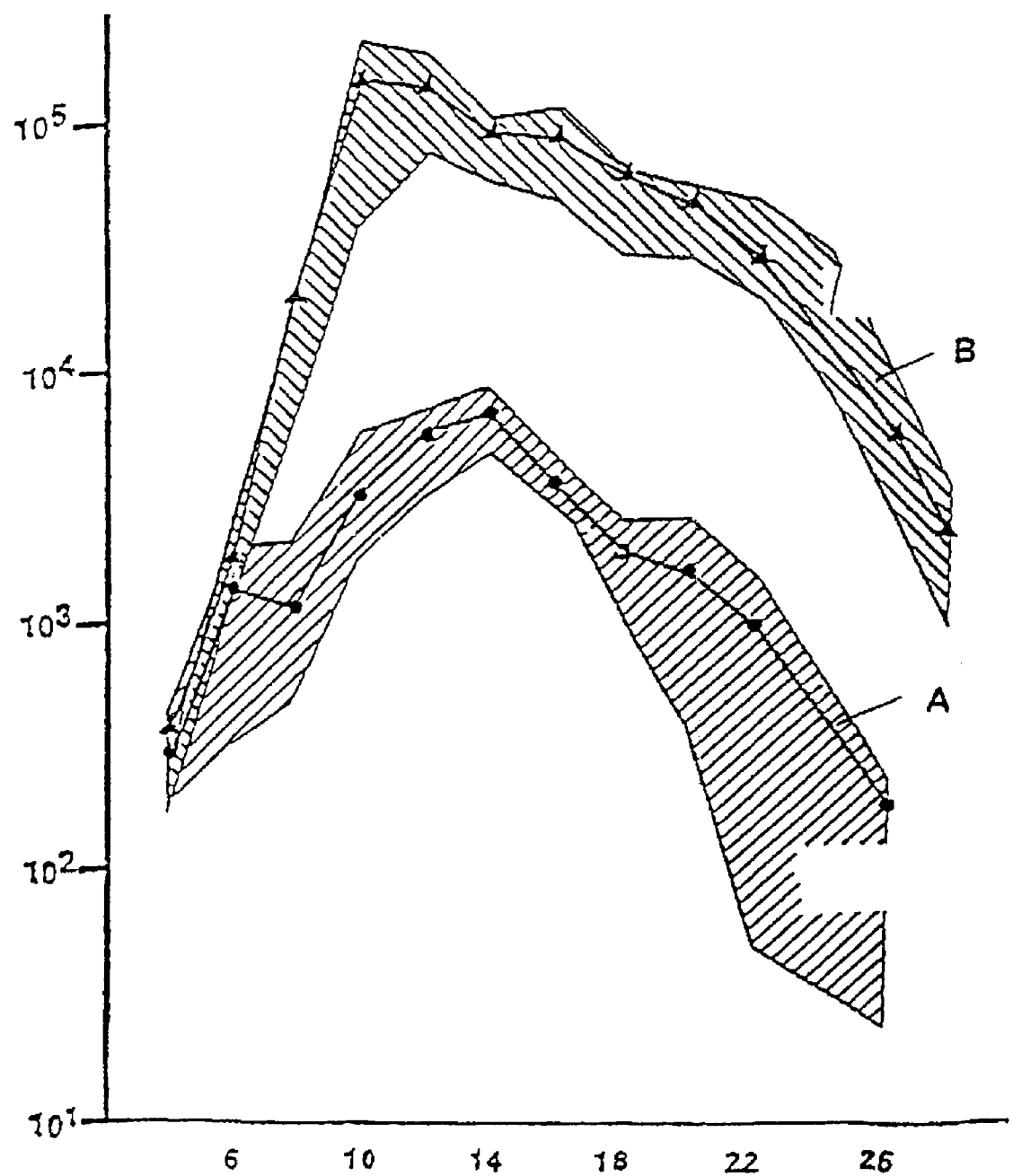
FIG. 5 are curves illustrating the variation in the measured parasitemia as the number of parasited red blood cells per microliter of blood as the function of time passed after infection. Curve A corresponds to the average values observed in three vaccinated monkeys and curve B corresponds to the average values in five controls.

The curves in FIG. 5 show the variation in the measured parasitemia as the number of parasited red blood cells per microlitre of blood (up the ordinate, logarithmic scale) as a function of the time passed after infection (in days). Curve A corresponds to the average values observed in the three vaccinated monkeys; curve B corresponds to the average values in the five control monkeys.

An examination of the Figure shows that the effect of the vaccination was to greatly reduce the parasitmisa.

Recombinant *Plasmodium cynomolgi* (p42 and p19) MSP1 Vaccination Test in the Toque Macaque *Macaca sinica*

Fifteen captured monkeys were used as follows: (1) 3 animals injected with 100 μg of soluble $PcMSP1_{p42}$; (2) 3 animals injected with 35 μg ($1^{st}$ injection) or 50 μg ($2^{nd}$ and $3^{rd}$ injections) of soluble $PcMSP1_{p42}$; (3) 3 animals injected with a mixture of $PcMSP1_{p42}$ and $_p19$; (4) 3 animals injected with adjuvant plus PBS; (5) 3 animals not injected. Complete and incomplete Freund adjuvant was used in the protocol described above. Injections were intramuscular at 4 week intervals. The challenge infection was made by injecting $2\times10^5$ red blood cells infected with *Plasmodium cynomolgi* 4 weeks after the last injection. Protection was evaluated by determining parasitemia daily in all animals by examining the parasitemia with Giemsa. Parasitemia were classified as negative only after counting 400 smear fields. The parasitemia were expressed as a percentage of parasitised red blood cells.

FIGS. 6A-6G show the results obtained. Each of them shows parasitemia (expressed as the percentage of parasitised red blood cells along the ordinate on a logarithmic scale) observed in the challenge animals as a function of the time after infection (in days along the abscissa).

Figure 6A:
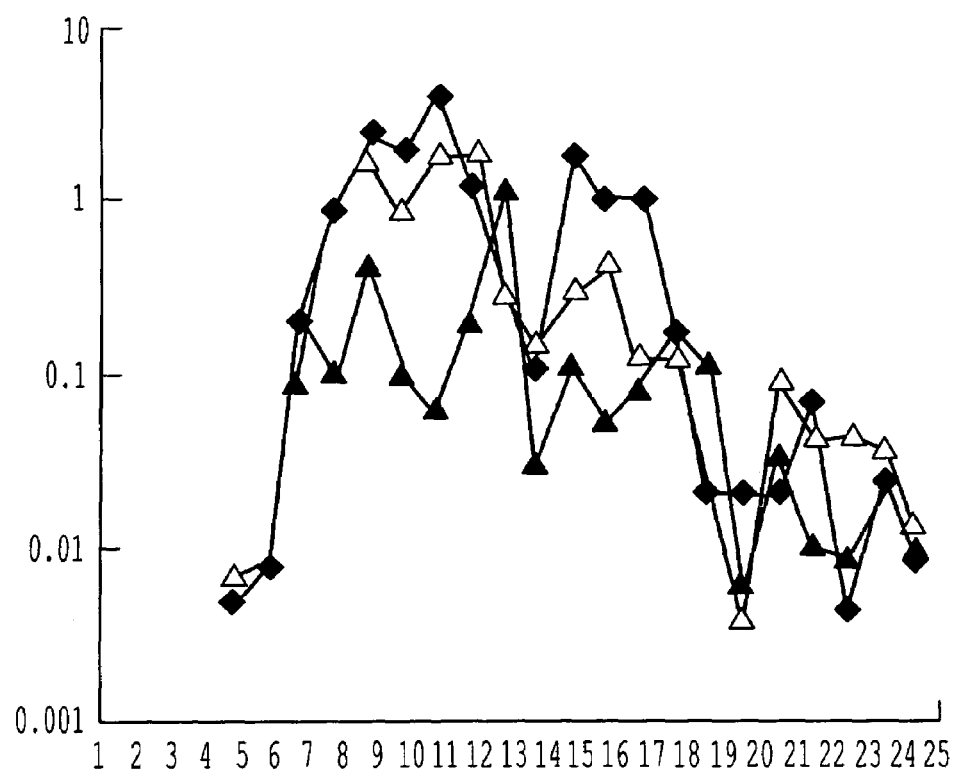
FIG. 6A is a graph illustrating the parasitemia observed in non-vaccinated control animals as a function of time after injection.
Figure 6B:
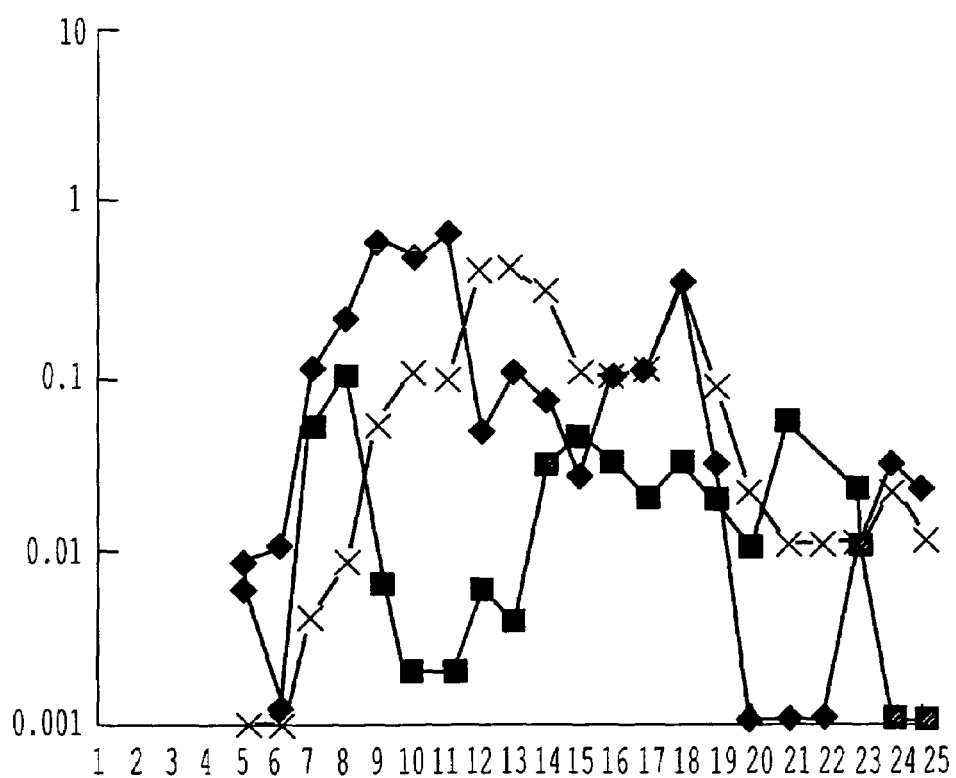
FIG. 6B is a graph illustrating the parasitemia observed in control animals which contained a saline solution also contain Freunds adjuvant as a function of time after injection.
Figure 6C:
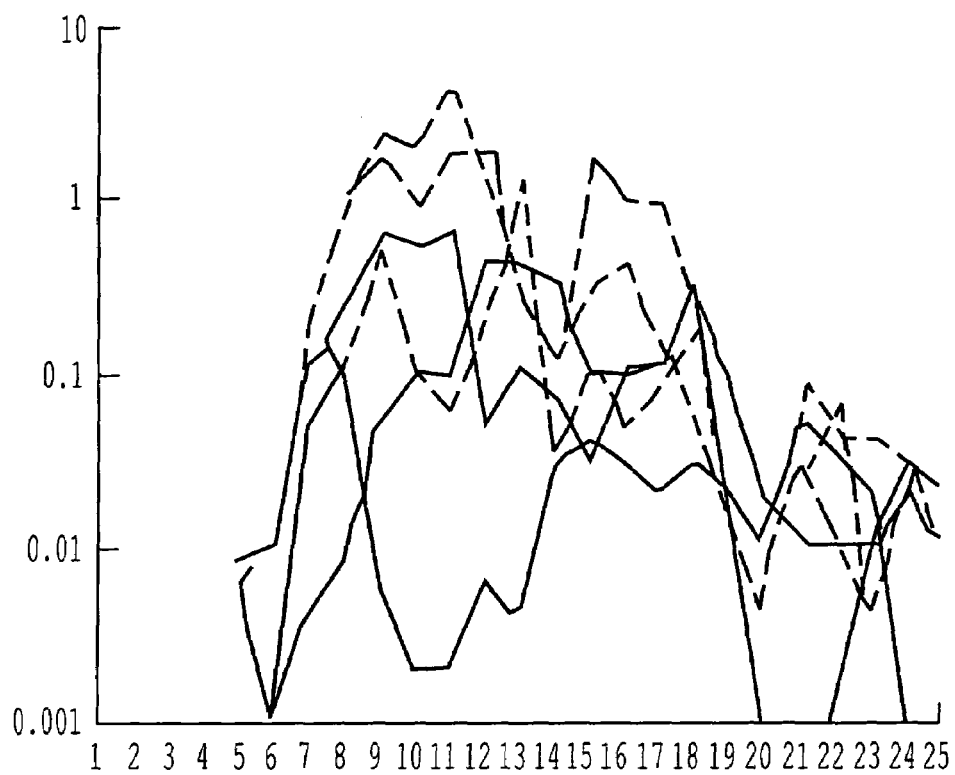
FIG. 6C is a superposition of FIGS. 6A and 6B.
Figure 6D:
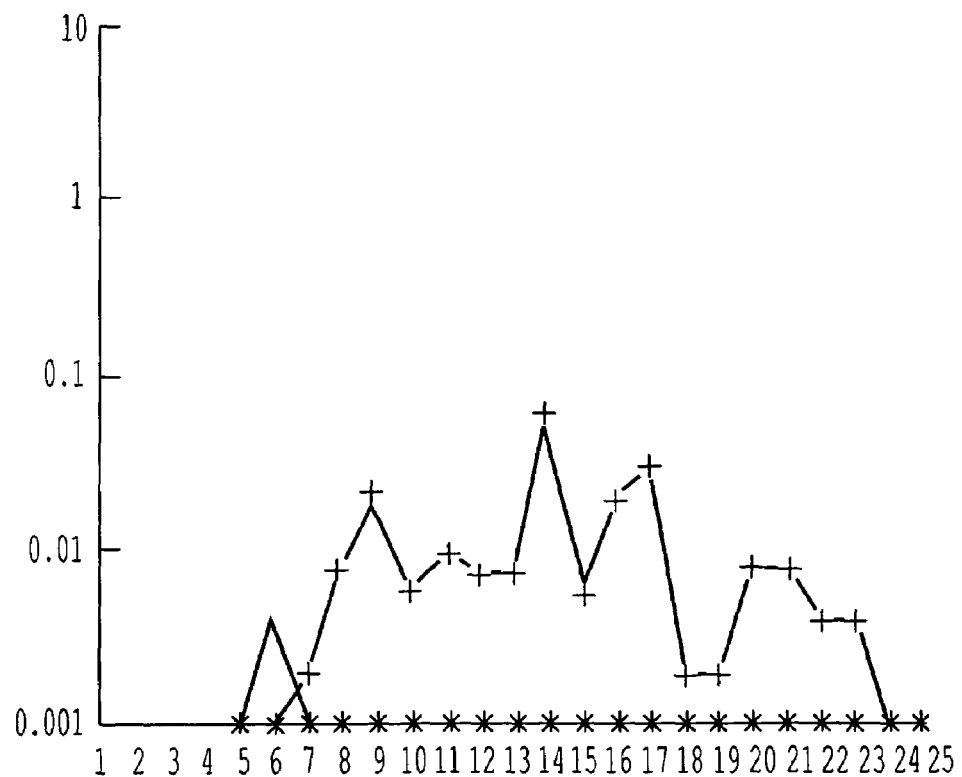
FIG. 6D is a graph illustrating parasitemia at the end of vaccination with p42 as a function of time.
Figure 6E:
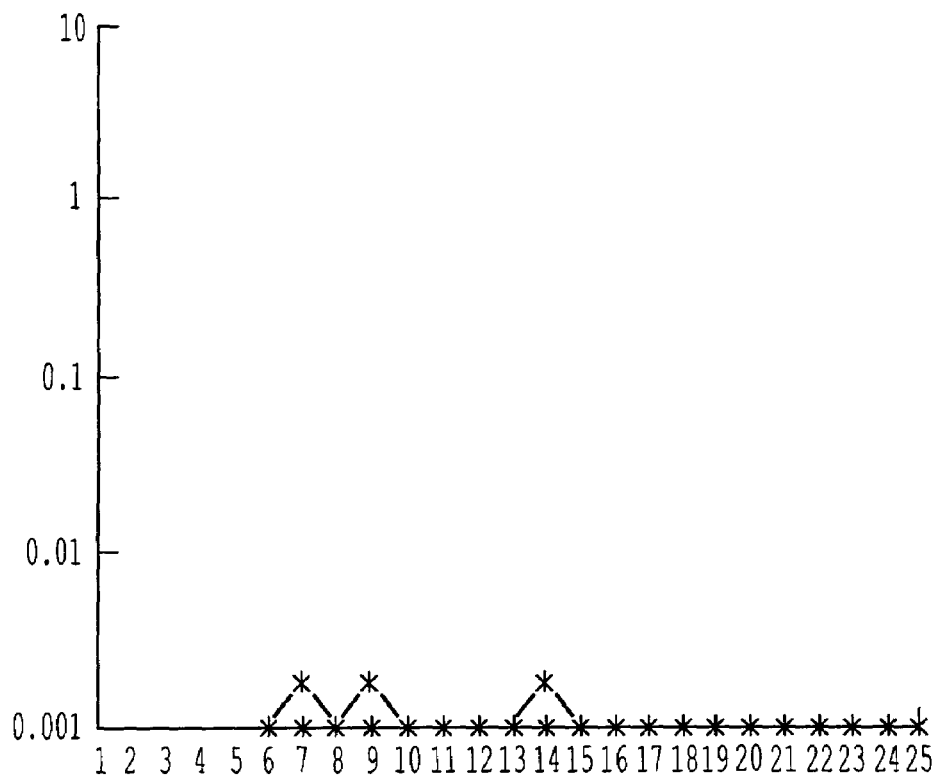
FIG. 6E is a graph illustrating parasitemia in animals vaccinated with p19 alone as a function of time.

The results relate to:
in FIG. 6A; non vaccinated control animals;
FIG. 6B relates to animals which received a saline solution also containing Freund adjuvant;
FIG. 6C is a superposition of FIGS. 6A and 6B, with the aim of highlighting the relative results resulting from administration of Freund adjuvant to the animals (the variations are clearly not significant);
FIG. 6D provides the results obtained at the end of vaccination with p42;
FIG. 6E concerns animals vaccinated with p19 alone;
finally, FIG. 6F concerns animals vaccinated with a mixture of p19 and p42.

Figure 6F:
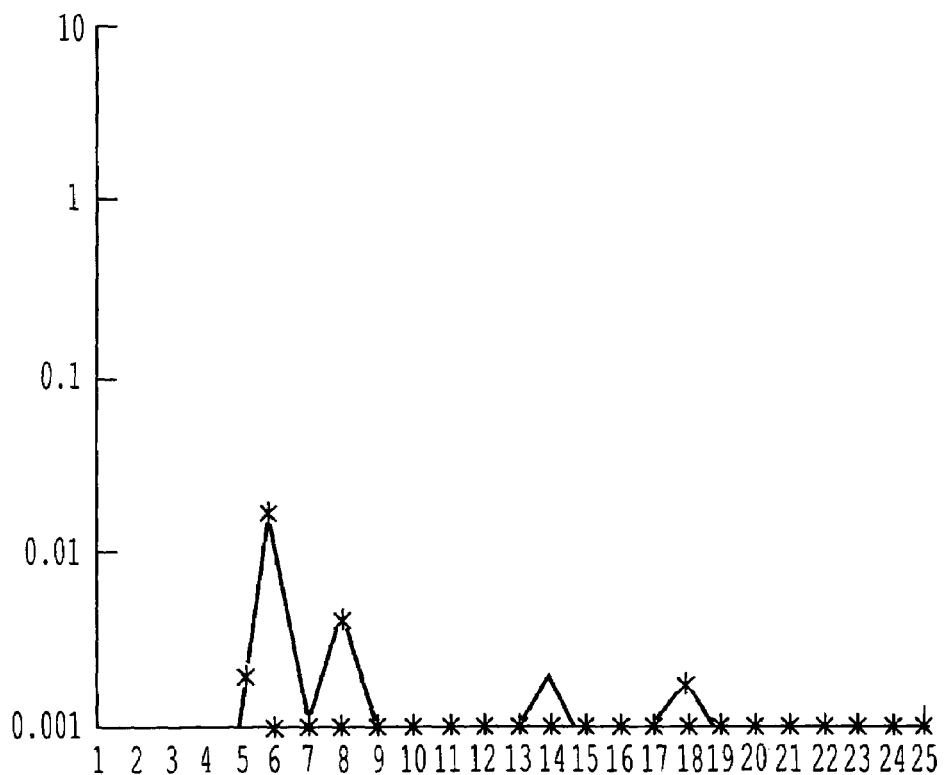
FIG. 6F is a graph illustrating parasitemia in animals with a mixture of P42 and P19 as a function of time.

The p42 certainly induced a certain level of protection. However, as shown in FIGS. 6E and 6F, the protection conferred by the recombinant p19 of the invention was considerably better.

The hypothesis can be formulated that the improved protection resulting from secondary cleavage of p42 which is accompanied by revealing free cysteine which, as a result, forms intermolecular bridges giving rise to p19 multimers which are highly characteristic of this form in recombinant proteins of the three species tested.

The numbers used to produce graphs (6A-6F) are given in FIG. 6G.

*P. cynomolgi* Toque Macaque Vaccination Test; Second Challenge Infection of Monkeys Vaccinated with p19 Alone and Controls (FIG. 8)

Figure 8A:
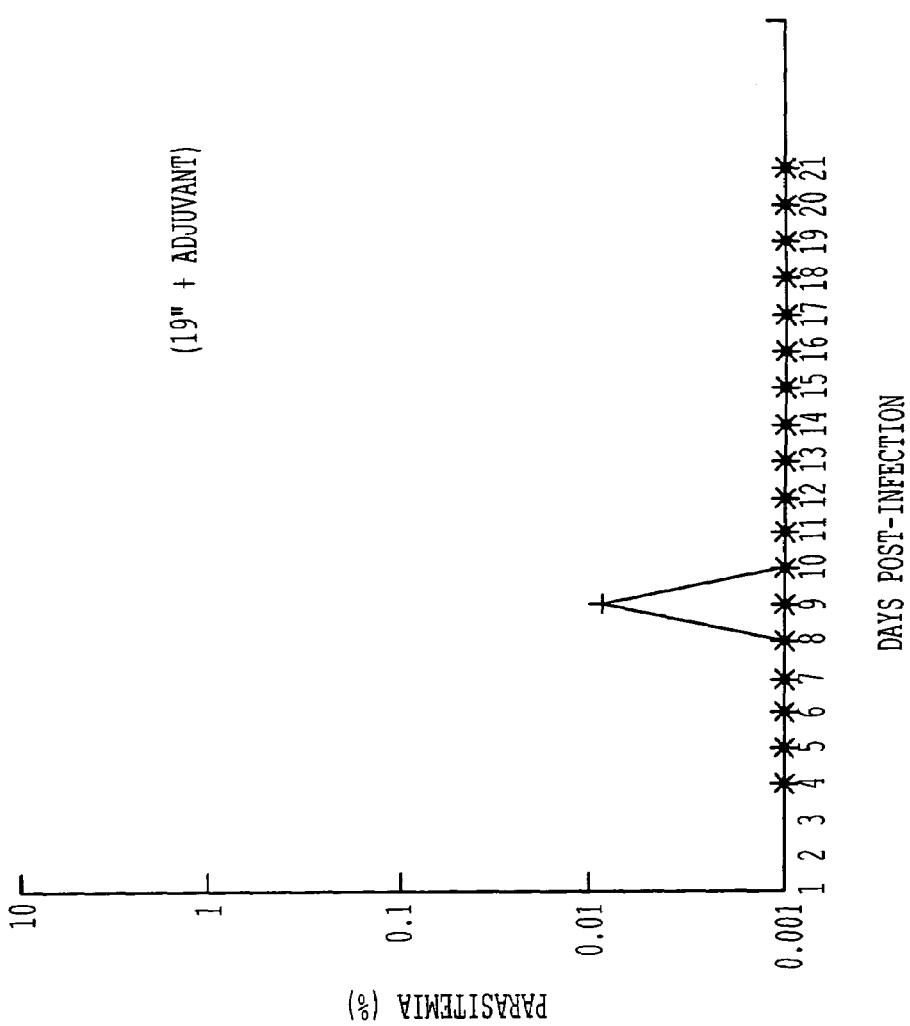
FIG. 8A is a graph illustrating the percent parasitemia versus days post infection of six monkeys which were immunized with recombinant MSP-1 (p19) six months earlier.
Figure 8B:
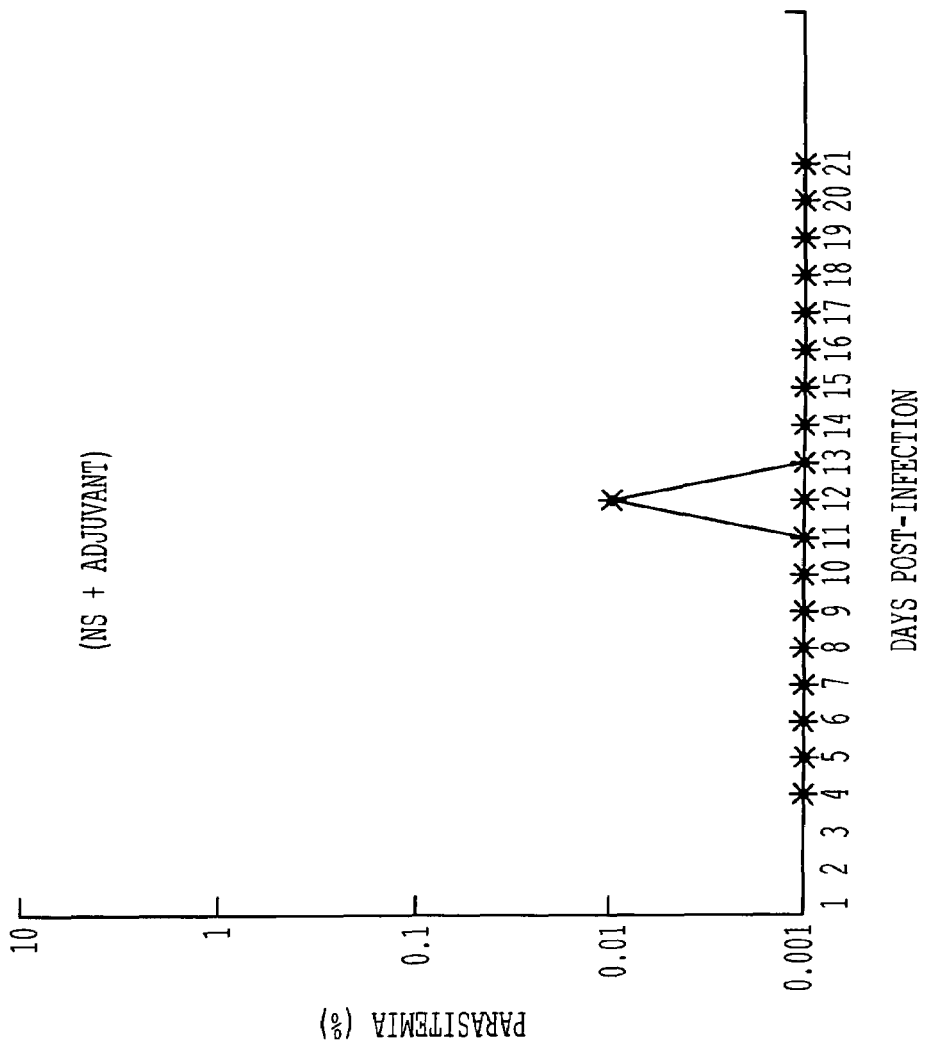
FIG. 8B is a graph illustrating the percent parasitemia versus days post infection of six monkeys that were immunized with normal saline and an adjuvant.
Figure 8C:
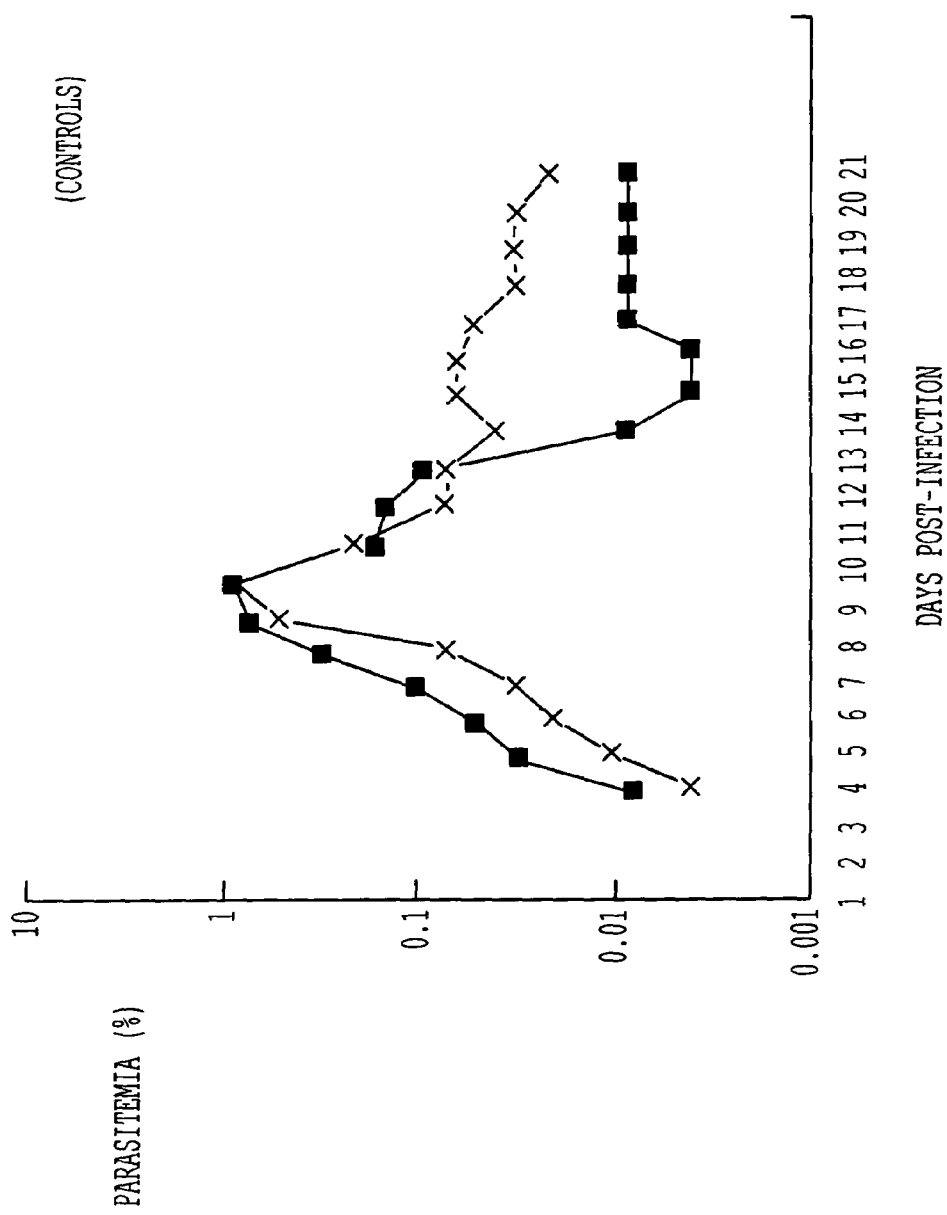
FIG. 8C is a graph illustrating the percent parasitemia versus days post infection of monkeys that were used as controls.

Six months later, with no other vaccination, the 3 macaques which received the p19 MSP-1 alone with FCA/FIA (FIG. 6E) and the 3 macaques which received a saline solution containing Freund adjuvant (FIG. 6B) and 2 new unaffected unvaccinated monkeys underwent a new challenge infection by injecting $1\times10^6$ red blood cells infected with *Plasmodium cynomolgi*. Protection was evaluated by determining parasitemia daily in all animals by examining Giemsa smears. The parasitemia were classified negative only after counting 400 smear fields. The parasitemia were expressed as the percentage of parasitised red blood cells (the figures used to produce graphs 8A-C are given in FIG. 8D). The six immunised animals which underwent challenge infection six months earlier had no detectable parasitemia except for 1 animal in each group which exhibited a parasitemia of 0.008% for 1 day (FIGS. 8A and 8B). The two unaffected controls exhibited a conventional parasitemia with a maximum of 0.8% and for 21 days (FIG. 8C). Thus the 3 animals vaccinated with the MSP-1 p19 were also protected six months later than the 3 controls which exhibited a complete conventional infection after the first challenge infection, despite the absence of or a very slight parasitemia after the first challenge infection. These results suggest that the protection period for p19 is at least six months.

Vaccination Test with p19 in Association with Alum in the *P. cynomolgi* Toque Macaque System (FIG. 9)

Figure 9A:
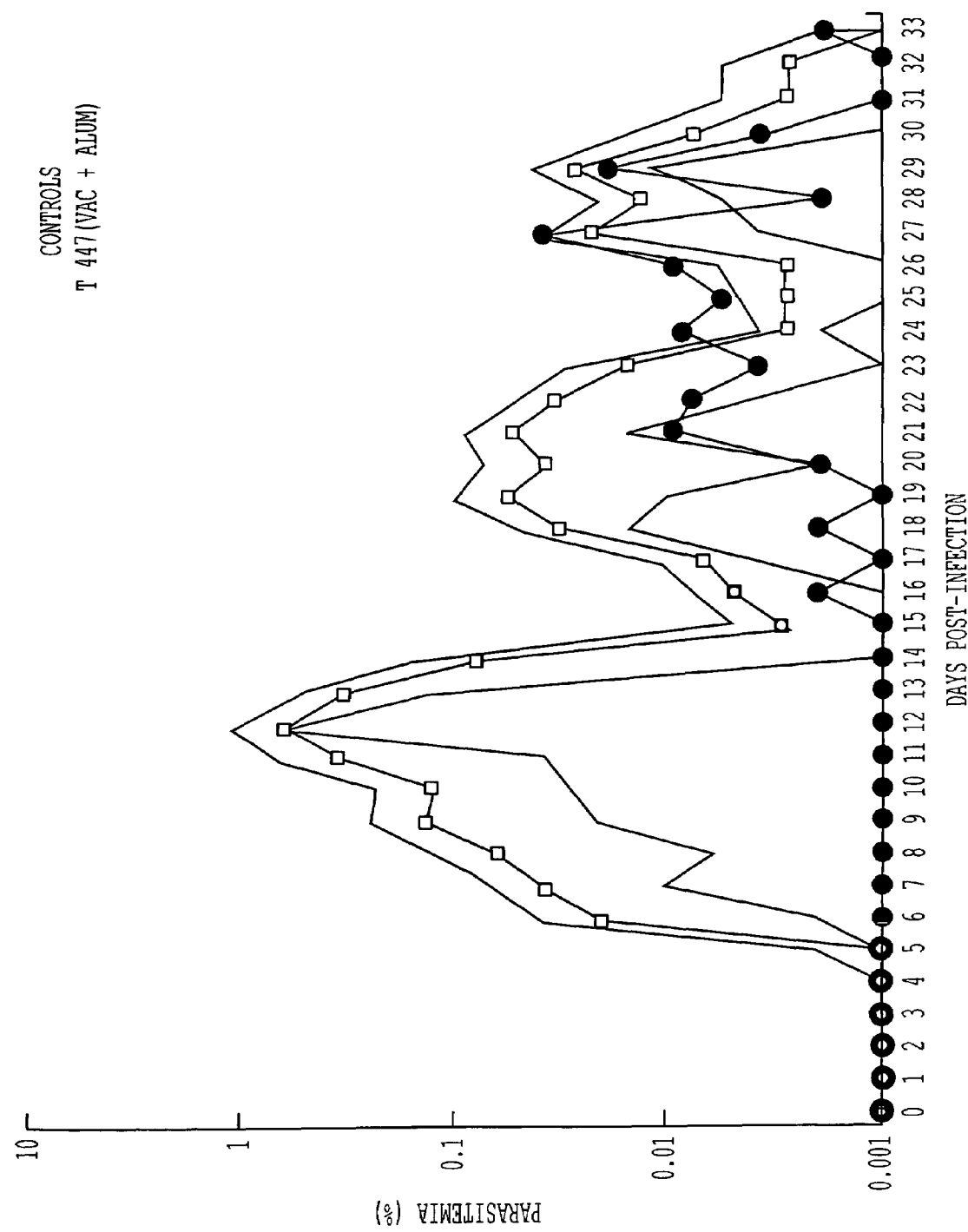
FIG. 9A is a graph illustrating the percent parasitemia versus days post infection of 2 macaques immunized with recombinant p19 and alum.
Figure 9C:
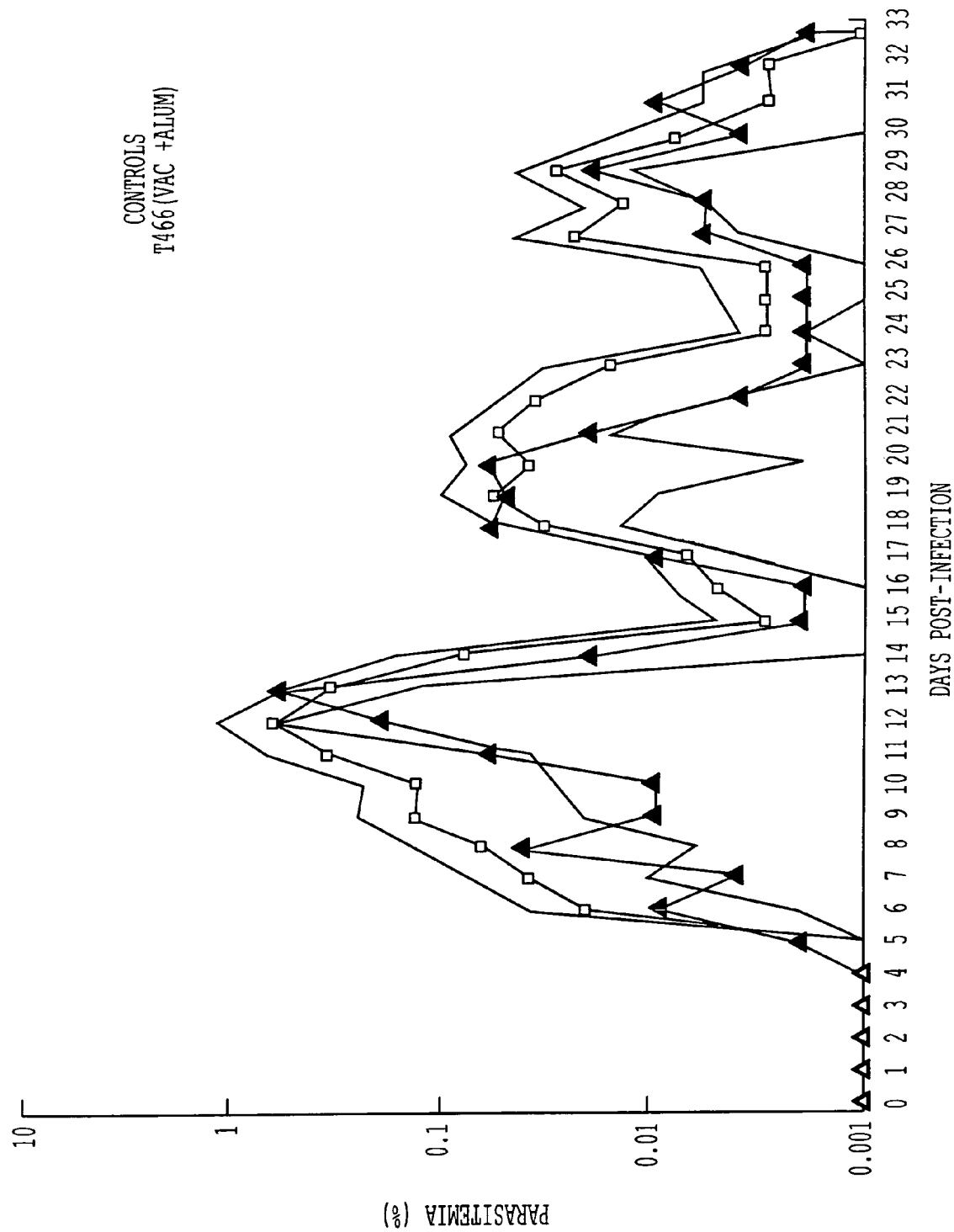
FIG. 9C is a graph illustrating the percent parasitemia versus days post infection of a macaque immunized with p19.
Figure 9D:
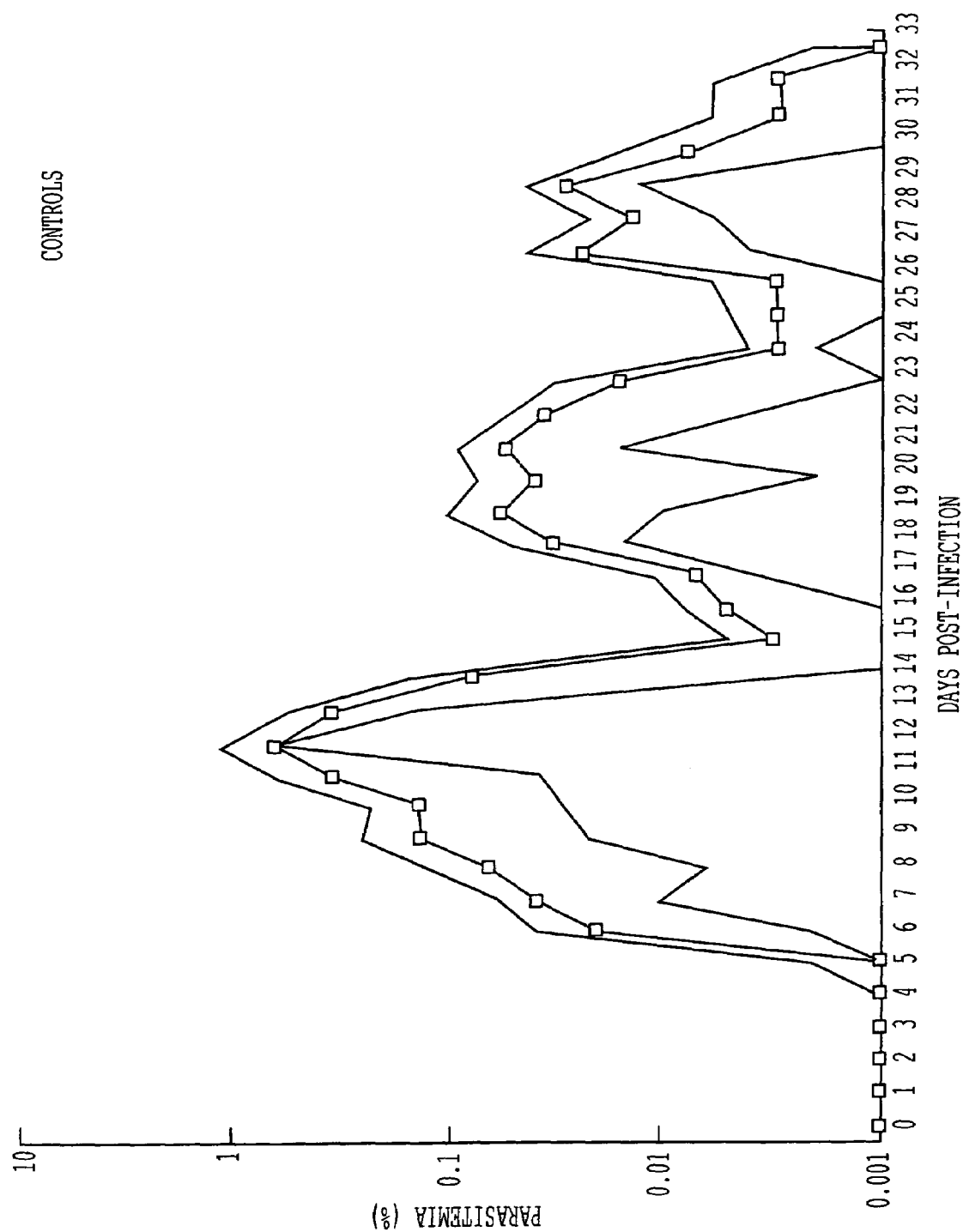
FIG. 9D is a graph illustrating the percent parasitemia versus days post infection of 3 control macaques immunized with physiological water and alum.
Figure 10A:
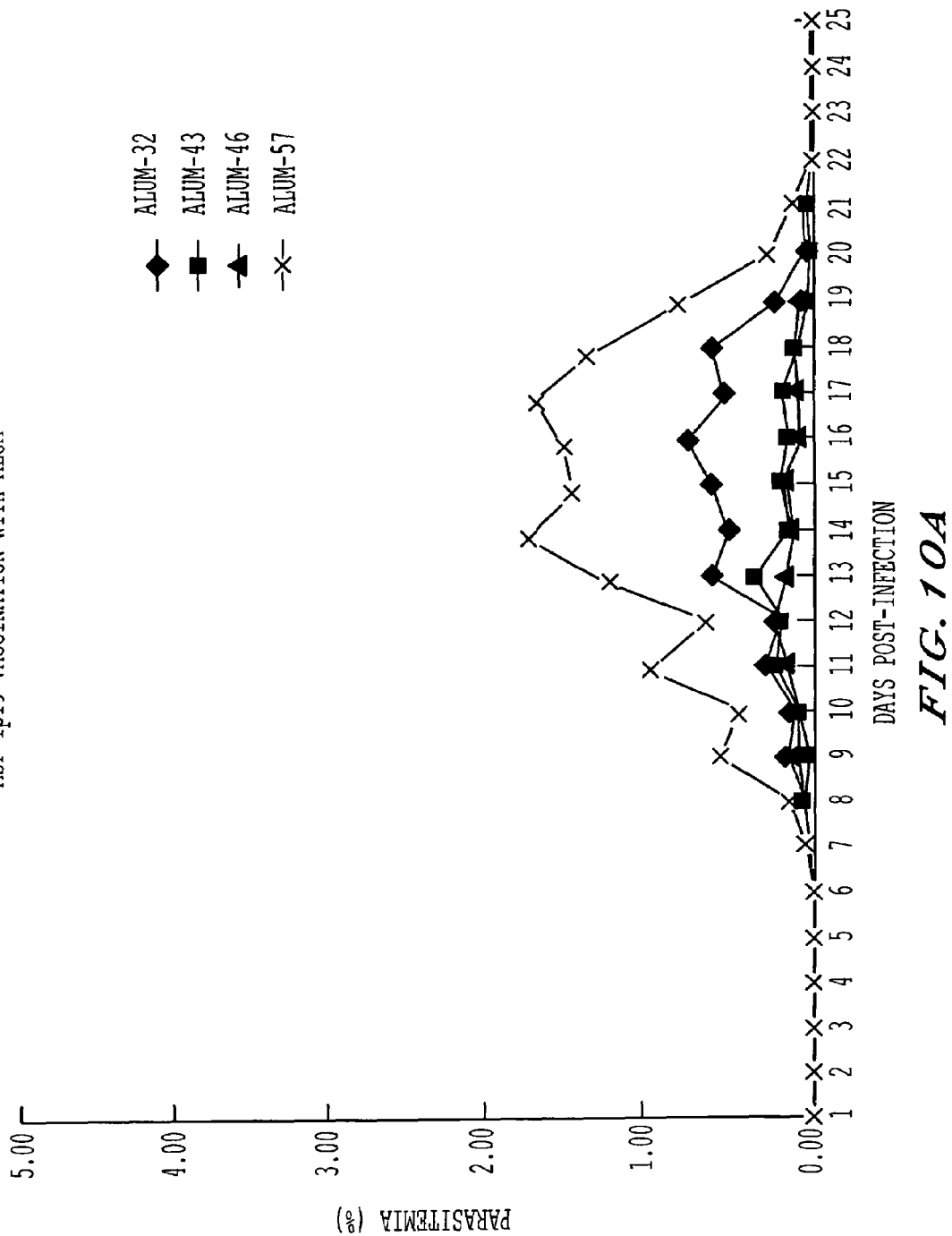
FIG. 10A is a graph illustrating the percent parasitemia versus days post infection in a squirrel monkey immunized with MSP-1 p19 and alum.
Figure 10C:
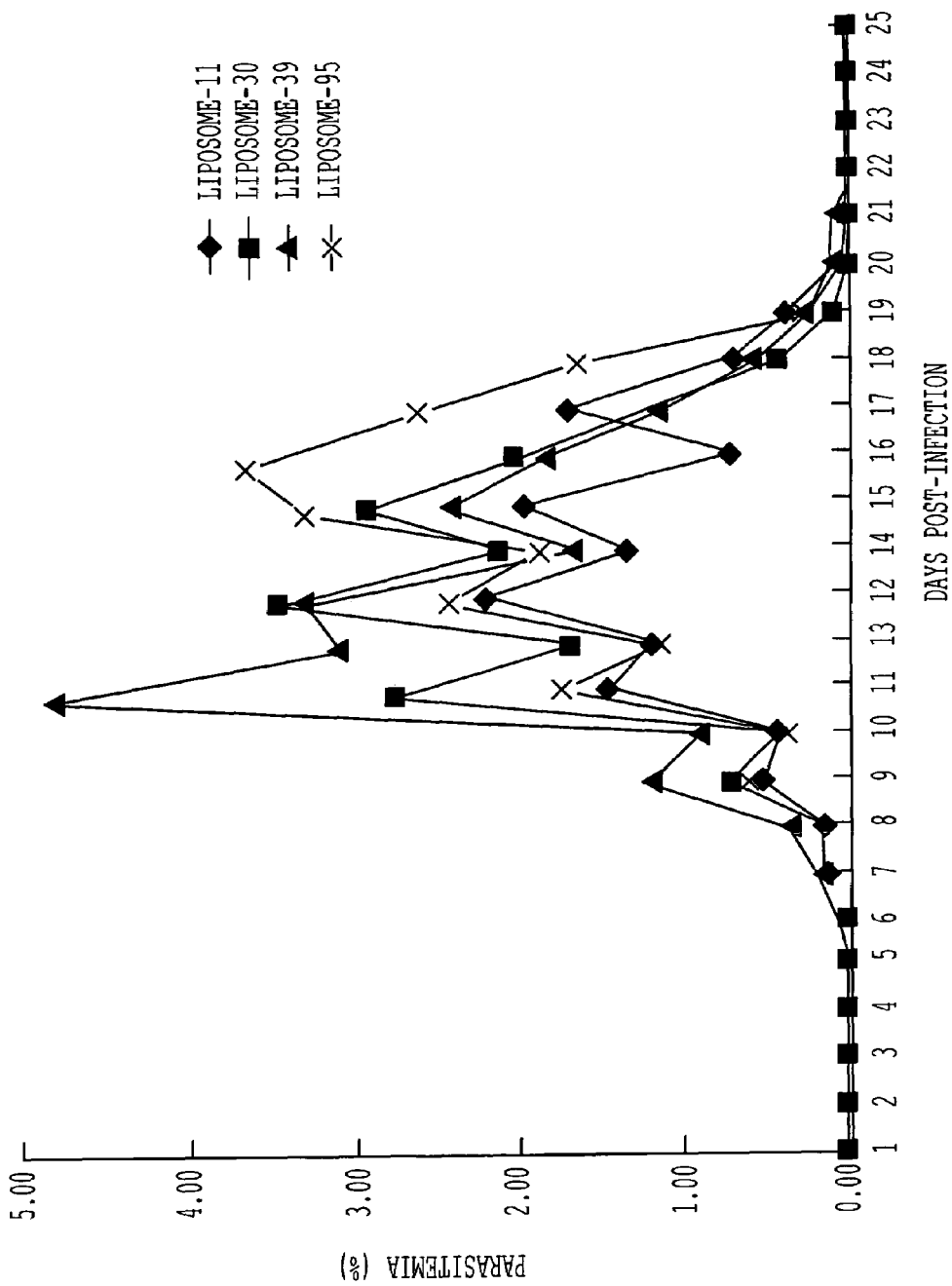
FIG. 10C is a graph illustrating the percent parasitemia versus days post infection in a squirrel monkey immunized with MSP-1 p19 with liposomes.
Figure 10D:
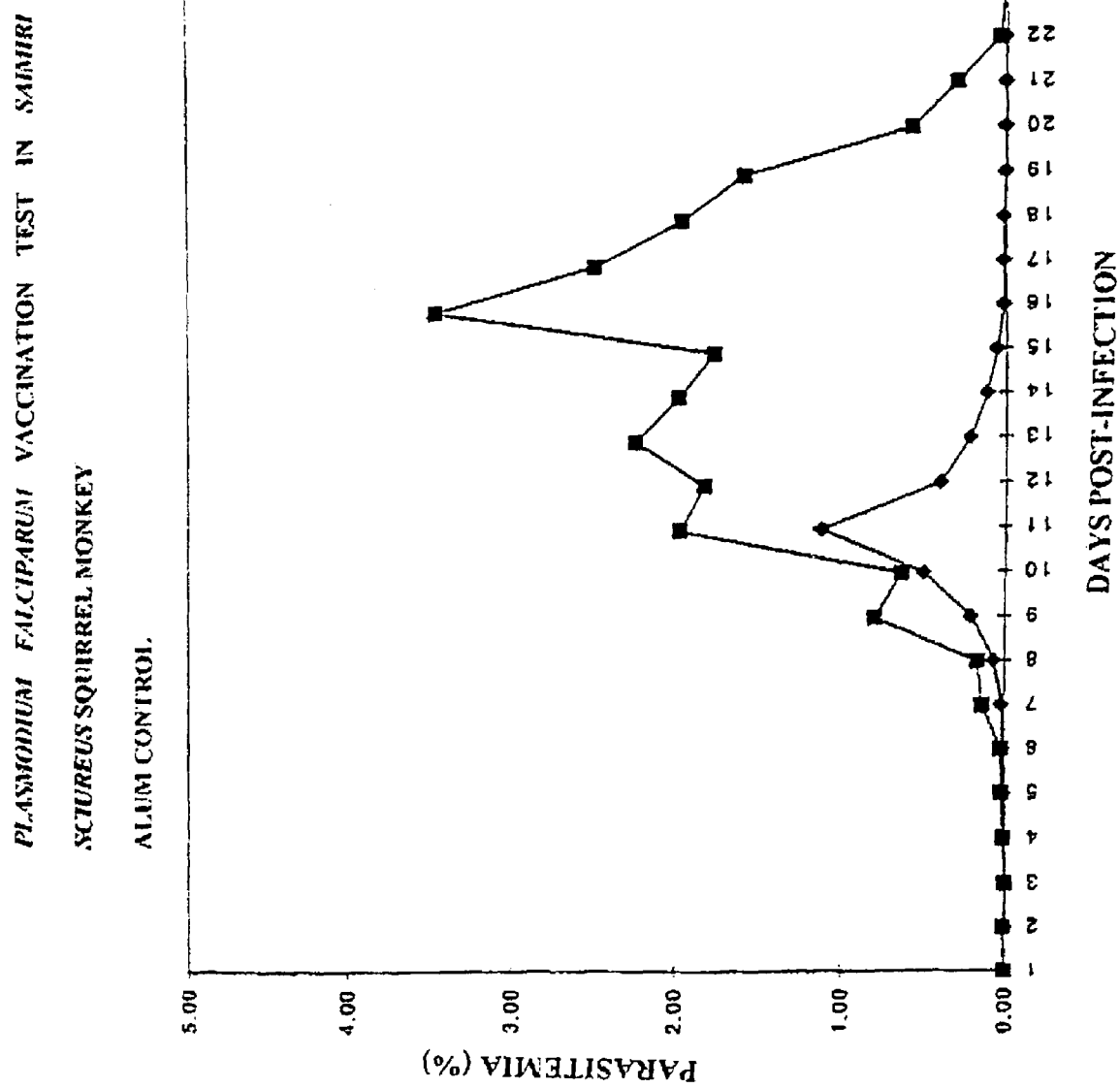
FIG. 10D is a graph illustrating the percent parasitemia versus days post infection in a squirrel monkey immunized with alum as the control.
Figure 10E:
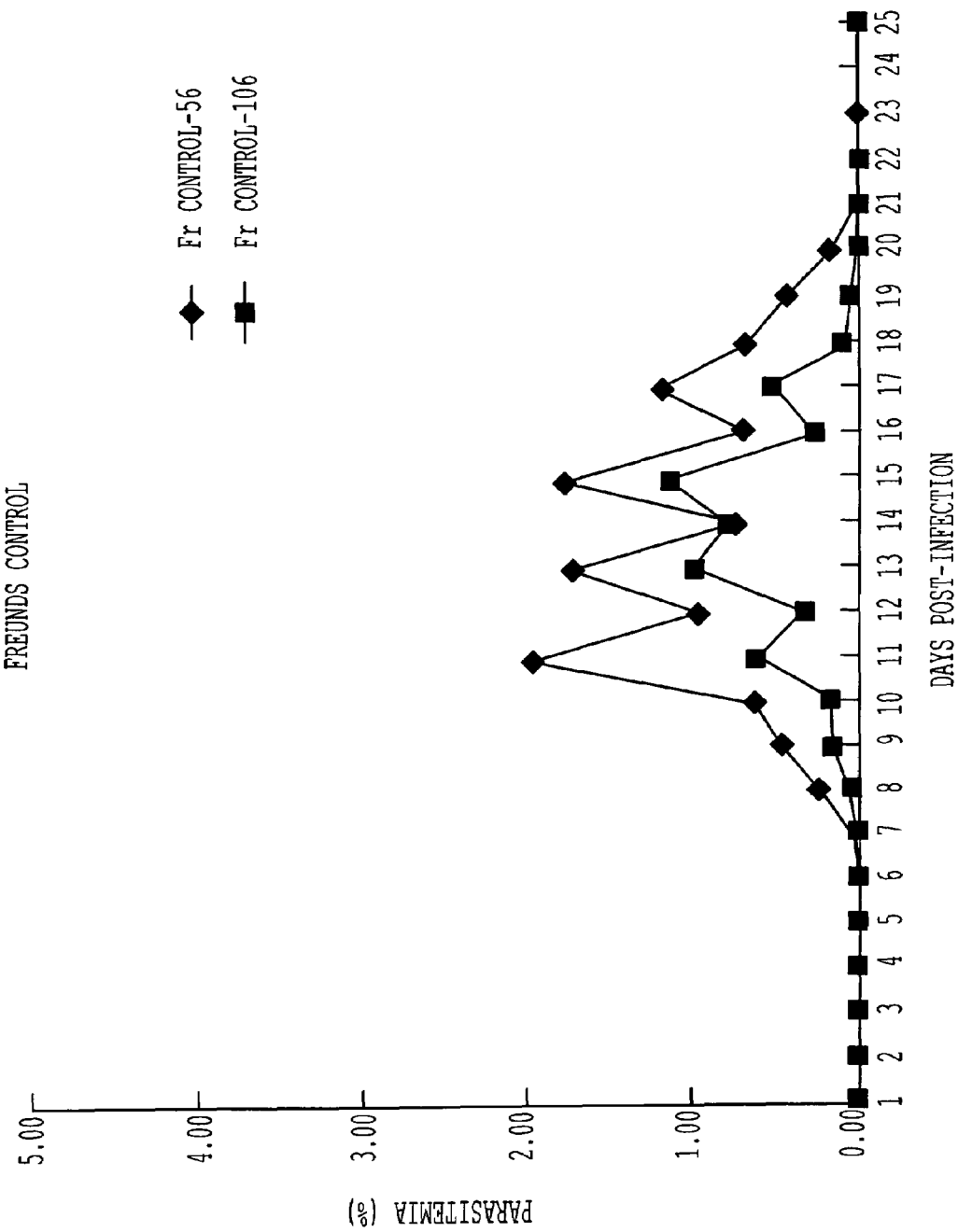
FIG. 10E is a graph illustrating the percent parasitemia versus days post infection in a squirrel monkey immunized with Freunds as the control.
Figure 10F:
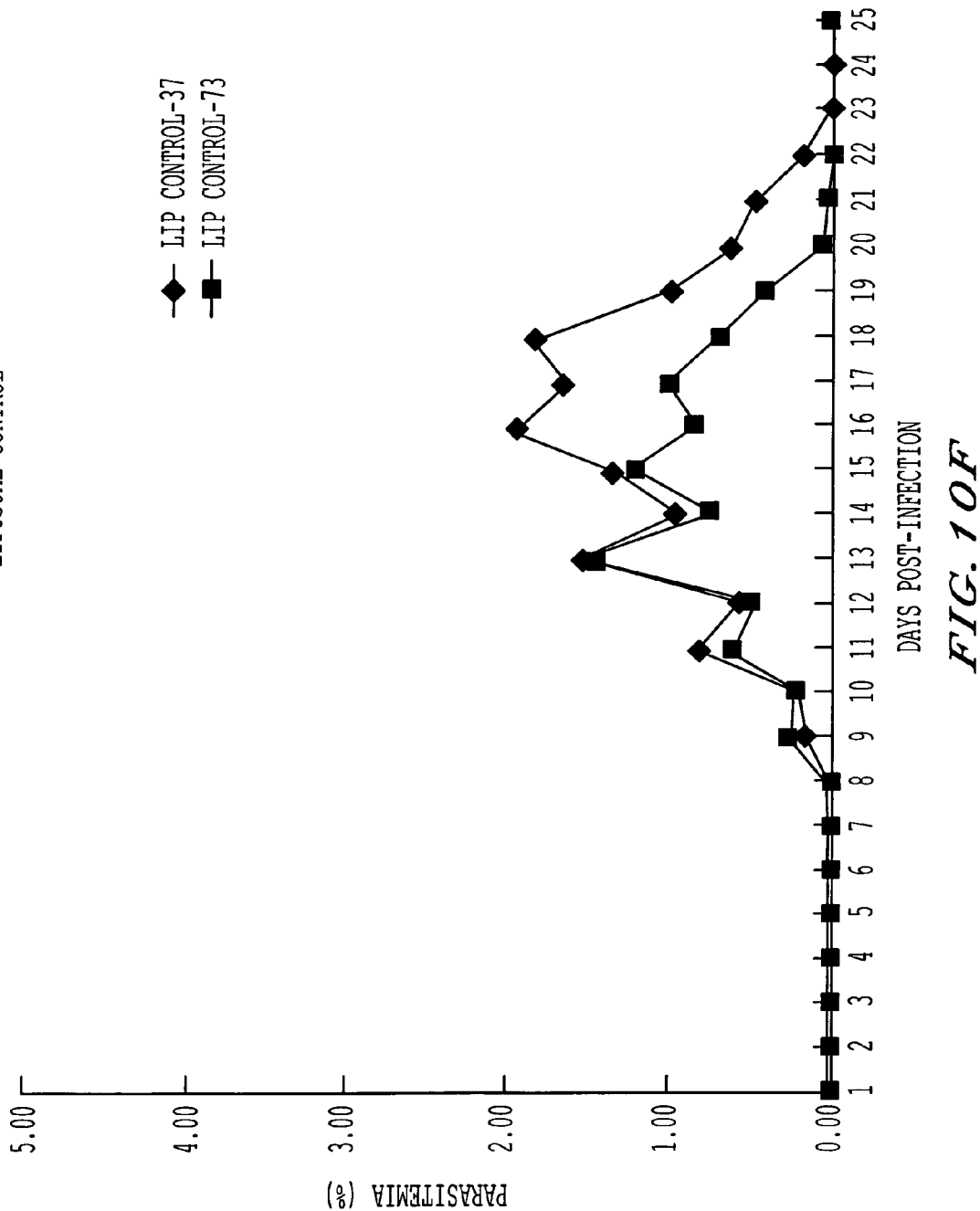
FIG. 10F is a graph illustrating the percent parasitemia versus days post infection in a squirrel monkey immunized with liposomes as the control.

The previous positive protection results were obtained using complete (FCA) or incomplete (FIA) Freund adjuvant. However, the only adjuvant which is currently allowed in man is alum. For this reason, we carried out a vaccination test with *P. cynomolgi* MSP-1 p19 in the toque macaque in the presence of alum as the adjuvant. Six captured macaques were used as follows: (1) 3 animals injected with 4 doses of 50 mg of recombinant *P. cynomolgi* MSP-1 p19 with 20 mg of alum; (2) 3 animals injected 4 times with physiological water and 10 mg of alum. The injections were intramuscular at 4 week intervals. The challenge infection was made by injecting $2\times10^5$ red blood cells infected with *P. cynomolgi* 4 weeks after the last injection. Protection was evaluated by daily determination of parasitemia in all animals by examining Giemsa smears. The parasitemia were classified negative only after counting 400 smear fields. Parasitemia were expressed as the percentage of parasitised red blood cells. The results of this experiment were as follows. 2 of the 3 macaques immunised with recombinant p19 with alum had about 30 times less total parasitemia during the infection period (FIGS. 9A and 9B) than the 3 control macaques immunised with physiological water and alum (FIG. 9D) after the challenge infection. The third macaque immunised with p19 (FIG. 9C) was not very different from the controls. For the vaccination test using *Plasmodium cynomolgi* p19 in the toque macaque, *macaca sinica*, described in FIG. 9, the data used to produce the graphs (9A-9D) are given in (FIG. 9E). While the results are a little less spectacular than the preceding results (FIGS. 6, 8), this is the first time that significant protection has been observed for recombinant MSP-1 with alum.

FIG. 10

Vaccination Test with a Recombinant *Plasmodium falciparum* p19 in the Squirrel Monkey Twenty *Saimiri sciureus guyanensis* (squirrel monkeys) of about 3 years old raised in captivity were used as follows: (1) 4 animals injected with 50 mg of soluble Pf MSP-1 p19 in the presence of Freund adjuvant as follows: $1^{st}$ injection: 1:1 FCA/FIA; $2^{nd}$ injection: 1:4 FCA/FIA; $3^{rd}$ injection: FIA. These adjuvant compositions were then mixed with 1:1 antigen in PBS; (2) 2 control animals received Freund adjuvant as described for (1) with only PBS; (3) 4 animals injected with 50 mg of soluble Pf MSP-1 p19 in the presence of 10 mg of alum (Alu-Gel-S, Serva); (4) 2 control animals received 10 mg of alum with only PBS; (5) 4 animals injected with about 50-100 mg of GPI anchored Pf MSP-1 p19 reconstituted into liposomes as follows: 300 mmoles of cholesterol and 300 mmoles of phosphatidyl choline were vacuum dried and resuspended in 330 mM of N-octylglucoside in PBS with 1.4 mg of Pf MSP-1 p19, GPI. This solution had been dialysed against PBS with adsorbent Bio-Beads SM-2 (Bio-Rad) and the liposomes formed were concentrated by centrifuging and resuspended in PBS The $1^{st}$ injection was made with fresh liposomes kept at 4° C. and the $2^{nd}$ and $3^{rd}$ injections were made with liposomes which had been frozen for preservation; (6) 2 animals injected with control liposomes made in the same way, in the absence of the p19, GPI antigen as described for (5); (7) 2 animals injected with physiological water. Three intramuscular injections were made at 4 week intervals. The challenge infection was made by injecting $1 \times 10^6$ red blood cells infected with *Plasmodium falciparum*. Protection was evaluated by determining parasitemia daily in all animals by examining the Giemsa smears. Parasitemia were expressed as the percentage of parasitised red blood cells. The results of this vaccination test are shown in FIG. 10, A-G.

The groups immunised with p19 in Freund adjuvant or liposome demonstrated similar parasitemia to the control groups after a challenge infection (one animal (number 29) vaccinated with p19 in Freund adjuvant died several days after challenge infection for reasons independent of vaccination (cardiac arrest". Irregularities in administration of the antigen in these 2 groups (poor Freund emulsion, congealed liposomes) did not allow the significance of these results to be completely evaluated. In the alum group, 2 animals showed total parasitemia for the duration of the infection about 4 times less than the controls, 1 animal about 3 times less and 1 animal was similar to the controls. This experiment was a little difficult to interpret due to the variability in the controls, probably due to the strain of parasite used for the challenge infection which would not have been quite adapted to the non splenectomised *Saimiri* model developed only recently in Cayenne. However, the real effect with alum, although imperfect, is encouraging in that our antigens seem to be the only recombinant *P. falciparum* MSP-1 versions which currently have shown a certain effectiveness in combination with alum.

Vaccination Test with a Recombinant *Plasmodium falciparum* p19 in the Squirrel Monkey (Same Test as for FIG. 10)

Monkeys bred in captivity were injected intramuscularly with 1 ml of inoculum twice at 4 week intervals as follows: (1) 4 animals injected with 50 μg of soluble PfMSP1p19 in the presence of Freund adjuvant as follows: $1^{st}$ injection: 1:1 FCA/FIA; $2^{nd}$ injection: 1:4 FCA/FIA; and mixed then 1:1 with the antigen in PBS; (2) 4 animals injected with 50 μg of soluble PfMSPp19 in the presence of 10 mg of alum; (3) 4 animals injected with about 50 μg of GPI anchored PfMSP1p19 reconstituted into liposomes composed of 1:1 molar cholesterol and phosphatidyl choline. The animals were bled 17 days after the second injection.

Red cells from a squirrel monkey with 30% parasitemia due to *P. falciparum* (with the mature forms in the majority) were washed with PBS and the residue was diluted 8 times in the presence of 2% SDS and 2% dithiothreitol and heated to 95° before being charged onto a polyacrylamide gel of 7.5% (separation gel) and 4% (stacking gel). After transfer to nitrocellulose, immunoblot analysis was carried out with antisera as follows: (1) pool of antisera of 4 monkeys vaccinated with soluble PfMSP1p19 in Freund adjuvant, twentieth dilution; (2) pool of antisera of 4 monkeys vaccinated with soluble PfMSP1p19 in alum adjuvant, twentieth dilution; (3) pool of antisera of 4 monkeys vaccinated with anchored PfMSP1p19 in liposomes, twentieth dilution; (4) monoclonal antibody, which reacts with a linear epitope of PfMSP1p19, 50 mg/ml; (5) SHI90 antisera pool originating from about twenty monkeys repeatedly infected with *P. falciparum* and which had become unaffectable by any subsequent infection with *P. falciparum*, five hundredth dilution; (6) antiserum pool of unaffected monkeys (never exposed to *P. falciparum*), twentieth dilution.

The results show that the 3 antiserum pools of monkeys vaccinated with PfMSP1p19 reacted strongly and specifically with very high molecular weight complexes (diffuse in the stacking gel) and present in parasite extracts containing more mature forms. These results support the hypothesis that a specific aggregate of PfMSP1p19 is present in vivo comprising epitopes which are reproduced in recombinant PfMSP1p19 molecules synthesised in the baculovirus system, in particular oligomeric forms thereof.

Figure 7A:
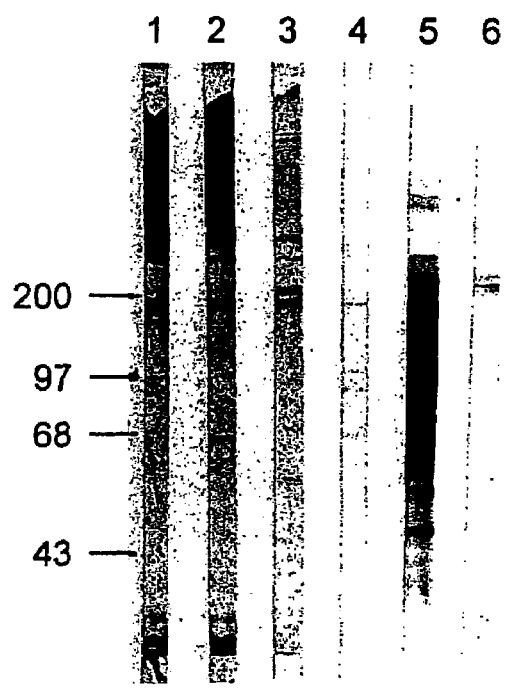
FIG. 7A is an immunoblot illustrating the in vivo response of monkeys to injections of p19 with Freunds adjuvant (1), with alum (2) and in the form of liposomes (3)

FIG. 7 also illustrated these results. It shows immunoblots produced on gel. The first three gel tracks illustrate the in vivo response of monkeys to injections of p19 [(1) with Freund adjuvant, (2) with alum, (3) in the form of a liposome] and in particular the existence of high molecular weight complexes supporting the hypothesis of in vivo aggregation of p19 in the form of an oligomer, specific to the maturation stage (when p42 is cut into p19 and p33).

This vaccination test also comprises a third injection identical to the previous injections. The injection with Freund adjuvant contained only FIA.

There were two animal controls for each group, namely: 2 control animals injected with PBS and Freund adjuvant; 2 control animals injected with PBS and alum; 2 control animals injected with liposomes without protein; and two control animals injected with PBS without adjuvant. Protection was evaluated as described above.

Figure 7B:
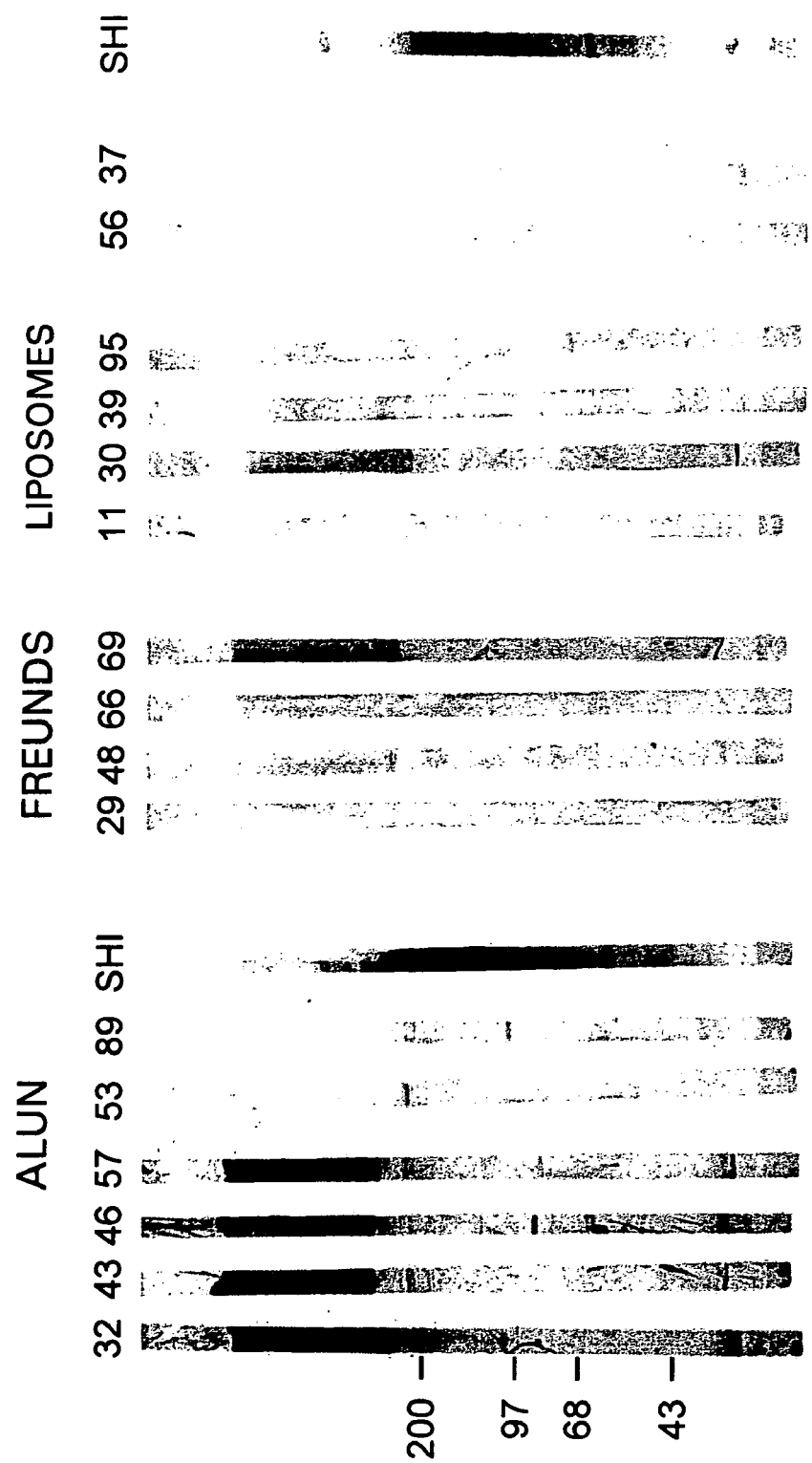
FIG. 7B is an immunoblot illustrating the in vivo responses of a squirrel monkey after three injections with p19 with Freunds adjuvant, with alum and in the form of liposomes.

FIG. 7B: The data for this Figure were derived from the squirrel monkey *P. falciparum* I vaccination test (FIG. 10 below). The numbers correspond to the individual monkeys noted in FIG. 10. The techniques and methods for this Figure were the same as for FIG. 7 except that the individual antiserum for each monkey was tested after three injections the day of the proof injection and the SHI antiserum was diluted by 1:250. The results show that the antiserum for 4 monkeys vaccinated with p19 and alum reacted strongly and specifically with very high molecular weight complexes while the monkeys of other groups vaccinated with p19 and Freund adjuvant or liposomes showed only a little reactivity with these complexes. Since the monkeys vaccinated with p19 and alum were also the best protected, this reactivity with the high molecular weight complexes appeared to indicate a protective effect, despite one monkey in the group not being protected with respect to the controls and that another was only partially protected.

The invention also, of course, concerns other applications, for example those described below with respect to certain of the examples, although these are not limiting in character.

Therapy

The recombinant molecule PfMSP1p19 can be used to produce specific antibodies which can possibly be used by passive transfer for therapeutics for severe malaria due to *P. falciparum* when there is a risk of death.

Diagnostics

The recombinant molecules PvMSP1p42, PvMSP1p19 and PfMSPp19 derived from baculovirus can and have been used to produce specific murine monoclonal antibodies. These antibodies, in combination with polyclonal anti-MSP1p19 antisera originating from another species such as the rabbit or goat can form the basis of a semi-quantitative diagnostic test for malaria which can distinguish between malaria due to *P. falciparum*, which can be fatal, and malaria due to *P. vivax*, which is generally not fatal. The principle of this test is to trap and quantify any MSP-1 molecule containing the p19 portion in the blood.

In this context, the advantages of the MSP1p19 molecule are as follows:

(i) it is both extremely well conserved in the same species and sufficiently divergent between different species to enable specific species reactants to be produced. No cross reaction has been observed between antibodies derived from PfMSP1p19 and PvMSP1p19;
(ii) the function of MSP1p19, while not known with precision, seems to be sufficiently important that this molecule does not vary significantly or is deleted without lethal effect for the parasite;
(iii) it is a major antigen found in all merozoites and thus it must in principle be detectable even at low parasitemia and proportionally to the parasitemia;
(iv) since the recombinant MSP1p19 molecules derived from baculovirus appear to reproduce more of the native structure of MSP1P19, the antibodies produced against these proteins will be well adapted to diagnostic use.

The microorganisms identified below have been deposited under Rule 6.1 of the Treaty of Budapest of 1 Feb. 1996, in the Collection Nationale de Cultures de Microorganisms (C.N.C.M.) of Institut Pasteur at 28, rv du Dr. Roux 75724, Paris Cedex 15 under the following registration numbers:

| Identification reference | Date of Deposit | Registration numbers |
| --- | --- | --- |
| PvMSP1p19A | Feb. 1, 1996 | I-1659 |
| PvMSP1p19S | Feb. 1, 1996 | I-1660 |
| PfMSP1p19A | Feb. 1, 1996 | I-1661 |
| PfMSP1p19S | Feb. 1, 1996 | I-1662 |
| PcMSP1p19S | Feb. 1, 1996 | I-1663 |
| G17-12 Hybridoma | Feb. 14, 1997 | I-1846 |

The invention also concerns the use of these antibodies, preferably fixed to a solid support (for example for affinity chromatography) for the purification of type p19 peptides initially contained in a mixture.

Purification means bringing this mixture into contact with an antibody, dissociating the antigen-antibody complex and recovering the purified p19 type peptide.

The invention also concerns vaccine compositions, also comprising mixtures of proteins or fragment, in particular mixtures of the type:

*P. falciparum* p19 and *P. vivax* p19;
*P. falciparum* p19 and *P. falciparum* p42, the latter if necessary being deprived of its most hypervariable regions;
*P. vivax* p19 and *P. vivax* p42, the latter if necessary being deprived of its most hypervariable regions;
*P. falciparum* p19 and *P. falciparum* p42, the latter if necessary being deprived of its most hypervariable regions, and *P. vivax* p19 and *P. vivax* p42, the latter if necessary being deprived of its most hypervariable regions.

In the present case, the most hypervariable regions are defined as regions I or region II and all or part of region III, the portion of region III which is preferably deleted being that which is juxtaposed to region II (the conserved portion being located to the side of the C-terminal of p33, close to the p19). Regions II and III are illustrated in FIG. 4.

The invention is not limited to the production of human vaccine. It is also applicable to the production of veterinary vaccine compositions using the corresponding proteins or antigens derived from parasites which are infectious for mammals and products under the same conditions. It is known that infections of the same type, babesiosis, also appear in cattle, dogs and horses. One of the antigens of the *Babesia* species has a high conformational homology (in particular in the two EFG-like and cysteine-rich domains) and functional homology with a protein portion of MSP-1 [(36), (37) and (38)].

Examples of veterinary vaccines using a soluble antigen against such parasites have been described (39).

It goes without saying that the p19s used in these mixtures can also be modified as described in the foregoing when considered in isolation.

REFERENCES (1) Holder, J. A. et al. (1982) "Biosynthesis and processing of a *Plasmodium falciparum* schizont antigen recognised by immune serum and a monoclonal antibody". J. Exp. Med. 156:1528-1538.
(2) Howard, R. et al. (1984) "Localisation of the major *Plasmodium falciparum* glycoprotein on the surface of mature intracellular trophozoites and schizonts". Mol. Biochem. Parasitol. 11: 349-362.
(3) Pirson, P. et al. (1985) "Characterization with monoclonal antibodies of a surface antigen of *Plasmodium falciparum* merozoites". J. Immunol. 134 1946-1951.
(4) Aley, S. B. et al. (1987) "*Plasmodium vivax*: Exoerythrocytic schizonts recognized by monoclonal antibodies against blood-stage schizonts". Exp. Parasitol. 64:188-194.
(5) Holder, A. A. (1988) "The precursor to major merozoite surface antigen: structure and role in immunity". Prog. Allergy 41: 72-97.
(6) Cooper, J. A. (1993) "Merozoite surface antigen-1 of *Plasmodium*". Parasitol. Today 9: 50-54.
(7) Holder, A. A., et al. (1987) "Processing of the precursor to the major merozoite antigens of *Plasmodium falciparum*" Parasitology 94:199-208.
(8) Lyon, J. A. et al. (1986) "Epitope map and processing scheme for the 195 000-dalton surface glycoprotein of *Plasmodium falciparum* merozoites deduced from cloned overlapping segments of the gene". Proc. Natl. Acad. Sci. USA 83: 2989-2993.
(9) Blackman, M. J. et al. (1992) "Secondary processing of the *Plasmodium falciparum* merozoite surface protein-1

(MSP1) by calcium-dependent membrane-bound serine protease: shedding of MSP1$_{33}$ as a noncovalently associated complex with other fragments of the MSOP1". Mol, Biochem. Parasitol. 50: 307-316.

(10) Haldar, K., et al. (1985) "Acylation of a *Plasmodium falciparum* merozoite surface antigen via sn-1,2-diacyl glycerol.". J. Biol. Chem. 260: 4969-4974.

(11) Braun Breton, C. et al. (1990) "Glycolipid anchorage of *Plasmodium falciparum* surface antigens". Res. Immunol. 141: 743-755.

(12) Kumar, S. et al. (1995) "Immunogenicity and in vivo Efficacy of Recombinant *Plasmodium falciparum* Merozoite surface protein-1 in *Aotus* Monkeys". Molecular Medicine, Vol. 1, 3: 325-332.

(13) Longacre, S. et al. (1994) "*Plasmodium vivax* merozoite surface protein 1 C-terminal recombinant proteins in baculovirus". Mol. Biochem. Parasitol. 64:191-205.

(15) McBride, J. S. et al. (1987) "Fragments of the polymorphic Mr 185 000 glycoprotein from the surface of isolated *Plasmodium falciparum* merozoites form an antigenic complex". Mol. Biochem. Parasitol. 23: 71-84.

(16) Blackman, M. J. et al. (1990) "A single fragment of a malaria merozoite surface protein remains on the parasite during red cell invasion and is the target of invasion-inhibiting antibodies". J. Exp. Med. 172: 379-382.

(17) Kaslow, D. C. et al. (1994) "Expression and antigenicity of *Plasmodium falciparum* major merozoite surface protein (MSP1$_{19}$) variants secreted from *Saccharomyces cerevisiae*". Mol. biochem. Parasitol. 63; 283-289.

(18) Chang, S. P., et al. (1992) "A carboxyl-terminal fragment of *Plasmodium falciparum* gp195 expressed by a recombinant baculovirus induces antibodies that completely inhibit parasite growth". J. Immunol. 149: 548-555

(19) Longacre, S. (1995) "The *Plasmodium cynomolgi* merozoite surface protein 1 C-terminal sequence and its homologies with other *Plasmodium* species". Mol. Biochem. Parasitol. 74:105-111.

(20) Del Portillo, H. A., et al. (1990) "Primary structure of the merozoite surface antigen 1 of *Plasmodium vivax* reveals sequences conserved between different *Plasmodium* species". Proc. Natl. Acad. Sci. USA 88: 4030-4034.

(21) Gibson, H. L., et al. (1992) "Structure and expression of the gene for Pv200, a major blood-stage surface antigen of *Plasmodium vivax*". Mol. biochem. Parasitol. 50: 325-334.

(22) Dissanaike, A. S. et al. (1965) "Two new malaria parasites, *Plasmodium cynomolgi ceylonensis* sub sp. nov. and *Plasmodium fragile* sp. nov. from monkeys in Ceylon". Ceylon Journal of Medical Science 14:1-9.

(23) Cochrane, A. H., et al. (1986) "Further studies on the antigenic diversity of the circumsporozoite proteins of the *Plasmodium cynomolgi* complex". Am. J. Trop. Med. Hyg. 35: 479-487.

(24) Naotunne, T. de S., et al. (1990) "*Plasmodium cynomolgi*: serum-mediated blocking and enhancement of infectivity to mosquitoes during infections in the natural host, *Macaca sinica*". Exp. Parasitol, 71, 305-313.

(25) Ihalamulla, R. L. et al. (1987) "*Plasmodium vivax*: isolation of mature asexual stages and gametocytes from infected human blood by colloidal silica (Percoll) gradient centrifugation". Trans. R. Soc. Trop. Med. Hyg. 81: 25-28.

(26) Kimura, E., et al. (1990) "Genetic diversity in the major merozoite surface antigen of *Plasmodium falciparum*: high prevalence of a third polymorphic form detected in strains derived in strains derived from malaria patients". Gene 91: 57-62.

(27) Heidrich, H.-G., et al. (1989) "The N-terminal amino acid sequences of the *Plasmodium falciparum* (FCBI) merozoite surface antigen of 42 and 36 kilodalton, both derived from the 185-195 kilodalton precursor". Mol. Biochem. Parasitol. 34:147-154.

(28) Blackman, M. J., et al. (1991) "Proteolytic processing of the *Plasmodium falciparum* merozoite surface protein-1 produces a membrane-bound fragment containing two epidermal growth factor-like domains". Mol. Biochem. Parasitol. 49: 29-34.

(29) Adams, J. M. et al. (1992) "A family of erythrocyte binding proteins of malaria parasites". Proc. Natl. Acad. Sci, 89:7085-7089.

(30) Sim B. K. L. (1995) "EBA-175: An erythrocyte-binding ligand of *Plasmodium falciparum*". Parasitology Today, vol. II, no 6:213-217.

(31) Sim B. K. L. (1994) "Receptor and ligand domains for invasion of erythrocytes by *Plasmodium falciparum*". Science, 264:1941-1944,

(32) Davies, A. et al. (1993), Biochem J. 295 (Pt3): 889-896. "Expression of the glycosylphosphatidylinositol-linked complement-inhibiting protein CD59 antigen in insect cells using a baculovirus vector".

(33) Haziot A. et al. (1994) J. Immunol. 152: 5868. "Recombinant soluble CD14 Inhibits LPS-Induced Tumor Necrosis Factor & Production by Cells in Whole Blood".

(34) Chang, S. P. et al., (1988) "*Plasmodium falciparum*: gene structure and hydropathy profile of the major merozoite surface antigen (gp195) of the Uganda-Palo Alto isolate. Exp. Parasitol. 67:1-11.

(35) Holder, A. S. et al. (1985) "Primary structure of the precursor to the three major surface antigens of *Plasmodium falciparum* merozoites", Nature 317: 270-273

(36) G. Bourdoiseau et al. (May 1995) "Les babésioses bovines", Le point vétérinaire, vol. 27, n-168.

(37) P. Bourdeau et al. (May 1995) "La babésiose canine à *Babesia canis*", Le point vétérinaire, vol. 27, n-168.

(38) C. Soule (May 1995) "Les babésioses équines", Le point vétérinaire, vol. 27 n-168.

(39) T. P. M. Schetters et al. (1995) "Vaccines against Babesiosis using Soluble Parasite Antigens", Parasitology Today, vol. 11, no 1 2.

(40) P. A. Burghaus et al. (1996) "Immunization of *Aotus nancymal* with Recombinant C Terminus of *Plasmodium falciparum* Merozoite *Surface Protein* 1 in Liposomes and Alum Adjuvant Does Not Induce Protection against a Challenge Infection", Infection and Immunity, 64:3614-3619.

(41) S. P. Chang, et ah. (1996) !A Recombinant Baculovirus 42-Kilodalton C-Terminal Fragment of *Plasmodium falciparum* Merozoite Surface Protein 1 Protects *Aotus* Monkeys against Malaria", Infection and Immunity, 64: 253-261.

(42) L. H. Miller et al. (1997) "The Need for Assays Predictive of Protection in Development of Malaria Bloodstage Vaccines", Parasitology Today, vol. 13, no 2:46-47

The invention also concerns hybridomas secreting specific antibodies selectively recognising the p19 of a MSP-1 protein in the merozoite form of a *Plasmodium* type parasite which is infectious for man other than *Plasmodium vivax* and which does not recognise *Plasmodium vivax*.

In particular, these hybridomas secrete monoclonal antibodies which do not recognise *Plasmodium vivax* and which specifically recognise *Plasmodium falciparum* p19.

The invention also concerns a hybridoma characterized in that it produces a specific antibody which specifically recognises the p19 of *P. vivax* and the p19 of *P. cynomolgi*. A F10-3 hybridoma has been constructed from the X63 Ag8 653 myeloma producing IgG 2b/k recognising the p42 glycoprotein of *Plasmodium vivax*.

The invention claimed is:

1. A baculovirus vector comprising:
   (a) a promoter;
   (b) a synthetic polynucleotide consisting of SEQ ID NO: 1 encoding a 19 kilodalton C-terminal fragment of a *Plasmodium falciparum* merozoite surface protein 1 (MSP-1) and having a GC content of 40% to 60%;
   (c) a polynucleotide sequence coding for at most 50 C-terminal amino acids of a 33 kilodalton N-terminal fragment of a *Plasmodium falciparum* merozoite surface protein 1 (MSP-1) positioned upstream of the synthetic polynucleotide; and
   (d) a polynucleotide encoding a signal sequence of a *Plasmodium* MSP-1 protein.

2. The baculovirus vector of claim 1, wherein the polynucleotide coding for said C-terminal amino acids has at most 35 amino acids.

3. The baculovirus vector of claim 1, wherein the polynucleotide coding for said C-terminal amino acids has at most 10 amino acids.

4. The baculovirus of claim 1, wherein the polynucleotide encoding the signal sequence is a polynucleotide encoding a *Plasmodium falciparum* MSP-1 protein.

5. A synthetic polynucleotide comprising
   (a) a synthetic sequence encoding a 19 kilodalton C-terminal fragment of a *Plasmodium falciparum* merozoite surface protein 1 (MSP-1) having a total GC content of 40% to 60%, wherein said synthetic sequence consists of SEQ ID NO: 1;
   (b) a polynucleotide sequence coding for at most 50 C-terminal amino acids of a 33 kilodalton N-terminal fragment of a *Plasmodium falciparum* merozoite surface protein 1 (MSP-1) positioned upstream of the synthetic sequence; and
   (c) a polynucleotide encoding a signal sequence of a *Plasmodium falciparum* MSP-1 protein.

6. The synthetic polynucleotide of claim 5, wherein said polynucleotide sequence coding for said C-terminal has at most 35 amino acids.

7. The synthetic polynucleotide of claim 5, wherein said polynucleotide sequence coding for said C-terminal has at most 10 amino acids.

8. A baculovirus vector for producing a recombinant protein comprising:
   (a) a promoter;
   (b) a synthetic polynucleotide consisting of SEQ ID NO: 1 encoding a 19 kilodalton C-terminal fragment of a *Plasmodium falciparum* merozoite surface protein 1 (MSP-1) and having a GC content of 40% to 60%;
   (c) a polynucleotide sequence coding for at most 50 C-terminal amino acids of a 33 kilodalton N-terminal fragment of a *Plasmodium falciparum* merozoite surface protein 1 (MSP-1) positioned upstream of the synthetic polynucleotide; and
   (d) a polynucleotide encoding a signal sequence of a *Plasmodium* MSP-1 protein, wherein said recombinant protein is produced as an oligomer.

\* \* \* \* \*

SEQUENCE LISTING

<160> NUMBER OF SEQ ID NOS: 15

<210> SEQ ID NO 1
<211> LENGTH: 291
<212> TYPE: DNA
<213> ORGANISM: Artificial Sequence
<220> FEATURE:
<223> OTHER INFORMATION: SYNTHETIC
<220> FEATURE:
<221> NAME/KEY: CDS
<222> LOCATION: (1)..(291)
<223> OTHER INFORMATION:

<400> SEQUENCE: 1

```
gaa ttc aac atc tcg cag cac caa tgc gtg aaa aaa caa tgt ccc gag       48
Glu Phe Asn Ile Ser Gln His Gln Cys Val Lys Lys Gln Cys Pro Glu
1               5                   10                  15 aac tct ggc tgt ttc aga cac ttg gac gag aga gag gag tgt aaa tgt       96
Asn Ser Gly Cys Phe Arg His Leu Asp Glu Arg Glu Glu Cys Lys Cys
            20                  25                  30 ctg ctg aac tac aaa cag gag ggc gac aag tgc gtg gag aac ccc aac      144
Leu Leu Asn Tyr Lys Gln Glu Gly Asp Lys Cys Val Glu Asn Pro Asn
        35                  40                  45 ccg acc tgt aac gag aac aac ggc ggt tgt gac gca gac gcc aaa tgc      192
Pro Thr Cys Asn Glu Asn Asn Gly Gly Cys Asp Ala Asp Ala Lys Cys
    50                  55                  60 acc gag gag gac tcg ggc agc aac ggc aag aaa atc acg tgt gag tgt      240
Thr Glu Glu Asp Ser Gly Ser Asn Gly Lys Lys Ile Thr Cys Glu Cys
65                  70                  75                  80 acc aaa ccc gac tcg tac ccg ctg ttc gac ggc atc ttc tgc agc taa      288
Thr Lys Pro Asp Ser Tyr Pro Leu Phe Asp Gly Ile Phe Cys Ser
                85                  90                  95 taa                                                                  291
```

<210> SEQ ID NO 2
<211> LENGTH: 95
<212> TYPE: PRT
<213> ORGANISM: Artificial Sequence
<220> FEATURE:
<223> OTHER INFORMATION: SYNTHETIC

<400> SEQUENCE: 2

```
Glu Phe Asn Ile Ser Gln His Gln Cys Val Lys Lys Gln Cys Pro Glu
1               5                   10                  15

Asn Ser Gly Cys Phe Arg His Leu Asp Glu Arg Glu Glu Cys Lys Cys
            20                  25                  30

Leu Leu Asn Tyr Lys Gln Glu Gly Asp Lys Cys Val Glu Asn Pro Asn
        35                  40                  45

Pro Thr Cys Asn Glu Asn Asn Gly Gly Cys Asp Ala Asp Ala Lys Cys
    50                  55                  60

Thr Glu Glu Asp Ser Gly Ser Asn Gly Lys Lys Ile Thr Cys Glu Cys
65                  70                  75                  80

Thr Lys Pro Asp Ser Tyr Pro Leu Phe Asp Gly Ile Phe Cys Ser
                85                  90                  95
```

<210> SEQ ID NO 3
<211> LENGTH: 279
<212> TYPE: DNA
<213> ORGANISM: Plasmodium falciparum

<400> SEQUENCE: 3

```
aacatttcac aacaccaatg cgtaaaaaaa caatgtccag aaaattctgg atgtttcaga    60
catttagatg aaagagaaga atgtaaatgt ttattaaatt acaaacaaga aggtgataaa   120
tgtgttgaaa atccaaatcc tacttgtaac gaaataatg gtggatgtga tgcagatgcc    180
aaatgtaccg aagaagattc aggtagcaac ggaaagaaaa tcacatgtga atgtactaaa   240
cctgattctt atccactttt cgatggtatt ttctgcagt                          279
```

```
<210> SEQ ID NO 4
<211> LENGTH: 354
<212> TYPE: DNA
<213> ORGANISM: Artificial Sequence
<220> FEATURE:
<223> OTHER INFORMATION: SYNTHETIC
<220> FEATURE:
<221> NAME/KEY: CDS
<222> LOCATION: (1)..(354)
<223> OTHER INFORMATION:

<400> SEQUENCE: 4
```

```
gaa ttc aac atc tcg cag cac caa tgc gtg aaa aaa caa tgt ccc gag     48
Glu Phe Asn Ile Ser Gln His Gln Cys Val Lys Lys Gln Cys Pro Glu
1               5                   10                  15 aac tct ggc tgt ttc aga cac ttg gac gag aga gag gag tgt aaa tgt     96
Asn Ser Gly Cys Phe Arg His Leu Asp Glu Arg Glu Glu Cys Lys Cys
            20                  25                  30 ctg ctg aac tac aaa cag gag ggc gac aag tgc gtg gag aac ccc aac    144
Leu Leu Asn Tyr Lys Gln Glu Gly Asp Lys Cys Val Glu Asn Pro Asn
        35                  40                  45 ccg acc tgt aac gag aac aac ggc ggc tgt gac gca gac gcc aaa tgc    192
Pro Thr Cys Asn Glu Asn Asn Gly Gly Cys Asp Ala Asp Ala Lys Cys
    50                  55                  60 acc gag gag gac tcg ggc agc aac ggc aag aaa atc acg tgt gag tgt    240
Thr Glu Glu Asp Ser Gly Ser Asn Gly Lys Lys Ile Thr Cys Glu Cys
65                  70                  75                  80 acc aaa ccc gac tcg tac ccg ctg ttc gac ggc atc ttc tgc agc tcc    288
Thr Lys Pro Asp Ser Tyr Pro Leu Phe Asp Gly Ile Phe Cys Ser Ser
                85                  90                  95 tct aac ttc ttg ggc atc tcg ttc ttg ttg atc ctc atg ttg atc ttg    336
Ser Asn Phe Leu Gly Ile Ser Phe Leu Leu Ile Leu Met Leu Ile Leu
            100                 105                 110 tac agc ttc att taa taa                                            354
Tyr Ser Phe Ile
        115
```

```
<210> SEQ ID NO 5
<211> LENGTH: 116
<212> TYPE: PRT
<213> ORGANISM: Artificial Sequence
<220> FEATURE:
<223> OTHER INFORMATION: SYNTHETIC

<400> SEQUENCE: 5
```

```
Glu Phe Asn Ile Ser Gln His Gln Cys Val Lys Lys Gln Cys Pro Glu
1               5                   10                  15

Asn Ser Gly Cys Phe Arg His Leu Asp Glu Arg Glu Glu Cys Lys Cys
            20                  25                  30

Leu Leu Asn Tyr Lys Gln Glu Gly Asp Lys Cys Val Glu Asn Pro Asn
        35                  40                  45

Pro Thr Cys Asn Glu Asn Asn Gly Gly Cys Asp Ala Asp Ala Lys Cys
    50                  55                  60
```

```
Thr Glu Glu Asp Ser Gly Ser Asn Gly Lys Lys Ile Thr Cys Glu Cys
 65                  70                  75                  80

Thr Lys Pro Asp Ser Tyr Pro Leu Phe Asp Gly Ile Phe Cys Ser Ser
                 85                  90                  95

Ser Asn Phe Leu Gly Ile Ser Phe Leu Leu Ile Leu Met Leu Ile Leu
            100                 105                 110

Tyr Ser Phe Ile
        115

<210> SEQ ID NO 6
<211> LENGTH: 342
<212> TYPE: DNA
<213> ORGANISM: Plasmodium falciparum

<400> SEQUENCE: 6
aacatttcac aacaccaatg cgtaaaaaaa caatgtccag aaaattctgg atgtttcaga    60
catttagatg aaagagaaga atgtaaatgt ttattaaatt acaaacaaga aggtgataaa   120
tgtgttgaaa atccaaatcc tacttgtaac gaaataatg gtggatgtga tgcagatgcc   180
aaatgtaccg aagaagattc aggtagcaac ggaaagaaaa tcacatgtga atgtactaaa   240
cctgattctt atccactttt cgatggtatt ttctgcagtt cctctaactt cttaggaata   300
tcattcttat taaatactcat gttaatatta tacagtttca tt                    342

<210> SEQ ID NO 7
<211> LENGTH: 387
<212> TYPE: DNA
<213> ORGANISM: Plasmodium falciparum
<220> FEATURE:
<221> NAME/KEY: CDS
<222> LOCATION: (1)..(387)
<223> OTHER INFORMATION:

<400> SEQUENCE: 7 atg aag gcg cta ctc ttt ttg ttc tct ttc att ttt ttc gtt acc aaa    48
Met Lys Ala Leu Leu Phe Leu Phe Ser Phe Ile Phe Phe Val Thr Lys
 1               5                  10                  15 gaa ttc aac atc tcg cag cac caa tgc gtg aaa aaa caa tgt ccc gag    96
Glu Phe Asn Ile Ser Gln His Gln Cys Val Lys Lys Gln Cys Pro Glu
             20                  25                  30 gaa ttc aac atc tcg cag cac caa tgc gtg aaa aaa caa tgt ccc gag   144
Glu Phe Asn Ile Ser Gln His Gln Cys Val Lys Lys Gln Cys Pro Glu
         35                  40                  45 aac tct ggc tgt ttc aga cac ttg gac gag aga gag gag tgt aaa tgt   192
Asn Ser Gly Cys Phe Arg His Leu Asp Glu Arg Glu Glu Cys Lys Cys
 50                  55                  60 ctg ctg aac tac aaa cag gag ggc gac aag tgc gtg gag aac ccc aac   240
Leu Leu Asn Tyr Lys Gln Glu Gly Asp Lys Cys Val Glu Asn Pro Asn
 65                  70                  75                  80 ccg acc tgt aac gag aac aac ggc ggc tgt gac gca gac gcc aaa tgc   288
Pro Thr Cys Asn Glu Asn Asn Gly Gly Cys Asp Ala Asp Ala Lys Cys
             85                  90                  95 acc gag gag gac tcg ggc agc aac ggc aag aaa atc acg tgt gag tgt   336
Thr Glu Glu Asp Ser Gly Ser Asn Gly Lys Lys Ile Thr Cys Glu Cys
            100                 105                 110 acc aaa ccc gac tcg tac ccg ctg ttc gac ggc atc ttc tgc agc taa   384
Thr Lys Pro Asp Ser Tyr Pro Leu Phe Asp Gly Ile Phe Cys Ser
        115                 120                 125 taa                                                                387
```

<210> SEQ ID NO 8
<211> LENGTH: 127
<212> TYPE: PRT
<213> ORGANISM: Plasmodium falciparum

<400> SEQUENCE: 8

```
Met Lys Ala Leu Leu Phe Leu Phe Ser Phe Ile Phe Phe Val Thr Lys
1               5                   10                  15

Glu Phe Asn Ile Ser Gln His Gln Cys Val Lys Lys Gln Cys Pro Glu
            20                  25                  30

Glu Phe Asn Ile Ser Gln His Gln Cys Val Lys Lys Gln Cys Pro Glu
        35                  40                  45

Asn Ser Gly Cys Phe Arg His Leu Asp Glu Arg Glu Cys Lys Cys
    50                  55                  60

Leu Leu Asn Tyr Lys Gln Glu Gly Asp Lys Cys Val Glu Asn Pro Asn
65                  70                  75                  80

Pro Thr Cys Asn Glu Asn Asn Gly Gly Cys Asp Ala Asp Ala Lys Cys
                85                  90                  95

Thr Glu Glu Asp Ser Gly Ser Asn Gly Lys Lys Ile Thr Cys Glu Cys
            100                 105                 110

Thr Lys Pro Asp Ser Tyr Pro Leu Phe Asp Gly Ile Phe Cys Ser
        115                 120                 125
```

<210> SEQ ID NO 9
<211> LENGTH: 330
<212> TYPE: DNA
<213> ORGANISM: Plasmodium falciparum
<220> FEATURE:
<221> NAME/KEY: CDS
<222> LOCATION: (1)..(330)
<223> OTHER INFORMATION:

<400> SEQUENCE: 9

```
gaa aca gaa agt tat aag cag ctt gta gcc aac gtg gac gaa ttc aac    48
Glu Thr Glu Ser Tyr Lys Gln Leu Val Ala Asn Val Asp Glu Phe Asn
1               5                   10                  15 atc tcg cag cac caa tgc gtg aaa aaa caa tgt ccc gag aac tct ggc    96
Ile Ser Gln His Gln Cys Val Lys Lys Gln Cys Pro Glu Asn Ser Gly
            20                  25                  30 tgt ttc aga cac ttg gac gag aga gag gag tgt aaa tgt ctg ctg aac    144
Cys Phe Arg His Leu Asp Glu Arg Glu Glu Cys Lys Cys Leu Leu Asn
        35                  40                  45 tac aaa cag gag ggc gac aag tgc gtg gag aac ccc aac ccg acc tgt    192
Tyr Lys Gln Glu Gly Asp Lys Cys Val Glu Asn Pro Asn Pro Thr Cys
    50                  55                  60 aac gag aac aac ggc ggc tgt gac gca gac gcc aaa tgc acc gag gag    240
Asn Glu Asn Asn Gly Gly Cys Asp Ala Asp Ala Lys Cys Thr Glu Glu
65                  70                  75                  80 gac tcg ggc agc aac ggc aag aaa atc acg tgt gag tgt acc aaa ccc    288
Asp Ser Gly Ser Asn Gly Lys Lys Ile Thr Cys Glu Cys Thr Lys Pro
                85                  90                  95 gac tcg tac ccg ctg ttc gac ggc atc ttc tgc agc taa taa            330
Asp Ser Tyr Pro Leu Phe Asp Gly Ile Phe Cys Ser
            100                 105
```

<210> SEQ ID NO 10
<211> LENGTH: 108
<212> TYPE: PRT
<213> ORGANISM: Plasmodium falciparum

<400> SEQUENCE: 10

```
Glu Thr Glu Ser Tyr Lys Gln Leu Val Ala Asn Val Asp Glu Phe Asn
1               5                   10                  15

Ile Ser Gln His Gln Cys Val Lys Lys Gln Cys Pro Glu Asn Ser Gly
                20                  25                  30

Cys Phe Arg His Leu Asp Glu Arg Glu Cys Lys Cys Leu Leu Asn
            35                  40                  45

Tyr Lys Gln Glu Gly Asp Lys Cys Val Glu Asn Pro Asn Pro Thr Cys
    50                  55                  60

Asn Glu Asn Asn Gly Gly Cys Asp Ala Asp Ala Lys Cys Thr Glu Glu
65                  70                  75                  80

Asp Ser Gly Ser Asn Gly Lys Lys Ile Thr Cys Glu Cys Thr Lys Pro
                85                  90                  95

Asp Ser Tyr Pro Leu Phe Asp Gly Ile Phe Cys Ser
            100                 105
```

<210> SEQ ID NO 11
<211> LENGTH: 379
<212> TYPE: PRT
<213> ORGANISM: Plasmodium cynomolgi

<400> SEQUENCE: 11

```
Asp Gln Val Thr Thr Gly Glu Ala Glu Ser Glu Ala Pro Glu Ile Ile
1               5                   10                  15

Val Pro Gln Gly Ile Asn Glu Tyr Asp Val Val Tyr Ile Lys Pro Leu
                20                  25                  30

Ala Gly Met Tyr Lys Thr Ile Lys Lys Pro Leu Glu Asn His Val Asn
            35                  40                  45

Ala Leu Asn Thr Asn Ile Ile Asp Met Leu Asp Ser Arg Leu Lys Lys
    50                  55                  60

Arg Asn Tyr Phe Leu Asp Val Leu Asn Ser Asp Leu Asn Pro Tyr Ser
65                  70                  75                  80

Ile Pro His Ser Gly Glu Tyr Ile Ile Lys Asp Pro Tyr Lys Leu Leu
                85                  90                  95

Asp Leu Glu Lys Lys Lys Leu Leu Gly Ser Tyr Lys Tyr Ile Gly Ala
            100                 105                 110

Ser Val Asp Lys Asp Met Val Thr Ala Asn Asp Gly Leu Ala Tyr Tyr
    115                 120                 125

Gln Lys Met Gly Asp Leu Tyr Lys Lys His Leu Asp Glu Val Asn Ala
130                 135                 140

Cys Ile Lys Glu Val Glu Ala Asn Ile Asn Lys His Asp Glu Glu Ile
145                 150                 155                 160

Lys Lys Ile Gly Ser Glu Ala Ser Lys Ala Asn Asp Lys Asn Gln Leu
                165                 170                 175

Asn Ala Lys Lys Glu Glu Leu Gln Lys Tyr Leu Pro Phe Leu Ser Ser
            180                 185                 190

Ile Gln Lys Glu Tyr Ser Thr Leu Val Asn Lys Val His Ser Tyr Thr
    195                 200                 205

Asp Thr Leu Lys Lys Ile Asn Asn Cys Gln Ile Glu Lys Lys Glu
210                 215                 220

Thr Glu Thr Ile Val Asn Lys Leu Glu Asp Tyr Ser Lys Met Asp Glu
225                 230                 235                 240

Glu Leu Asp Val Tyr Lys Gln Ser Lys Glu Asp Val Lys Ser
                245                 250                 255

Ser Gly Leu Leu Glu Lys Leu Met Asn Ser Lys Leu Ile Asn Gln Glu
            260                 265                 270
```

-continued

Glu Ser Lys Lys Ala Leu Ser Glu Leu Leu Asn Val Gln Thr Gln Met
            275                 280                 285

Leu Asn Met Ser Ser Glu His Arg Cys Ile Asp Thr Asn Val Pro Glu
            290                 295                 300

Asn Ala Ala Cys Tyr Arg Tyr Leu Asp Gly Thr Glu Glu Trp Arg Cys
305                 310                 315                 320

Leu Leu Tyr Phe Lys Glu Asp Ala Gly Lys Cys Val Pro Ala Pro Asn
            325                 330                 335

Met Thr Cys Lys Asp Lys Asn Gly Gly Cys Ala Pro Glu Ala Glu Cys
            340                 345                 350

Lys Met Asn Asp Lys Asn Glu Ile Val Cys Lys Cys Thr Lys Glu Gly
            355                 360                 365

Ser Glu Pro Leu Phe Glu Gly Val Phe Cys Ser
            370                 375

<210> SEQ ID NO 12
<211> LENGTH: 380
<212> TYPE: PRT
<213> ORGANISM: Plasmodium vivax-like sp.

<400> SEQUENCE: 12

Asp Gln Val Thr Thr Gly Glu Ala Glu Ser Glu Ala Pro Glu Ile Leu
1               5                   10                  15

Val Pro Ala Gly Ile Ser Asp Tyr Asp Val Val Tyr Leu Lys Pro Leu
            20                  25                  30

Ala Gly Met Tyr Lys Thr Ile Lys Lys Gln Leu Glu Asn His Val Asn
            35                  40                  45

Ala Phe Asn Thr Asn Ile Thr Asp Met Leu Asp Ser Arg Leu Lys Lys
        50                  55                  60

Arg Asn Tyr Phe Leu Glu Val Leu Asn Ser Asp Leu Asn Pro Phe Lys
65                  70                  75                  80

Tyr Ser Pro Ser Gly Glu Tyr Ile Ile Lys Asp Pro Tyr Lys Leu Leu
            85                  90                  95

Asp Leu Glu Lys Lys Lys Lys Leu Leu Gly Ser Tyr Lys Tyr Ile Gly
            100                 105                 110

Ala Ser Ile Asp Lys Asp Leu Ala Thr Ala Asn Asp Gly Val Thr Tyr
            115                 120                 125

Tyr Asn Lys Met Gly Glu Leu Tyr Lys Thr His Leu Thr Ala Val Asn
            130                 135                 140

Glu Glu Val Lys Lys Val Glu Ala Asp Ile Lys Ala Glu Asp Asp Lys
145                 150                 155                 160

Ile Lys Lys Ile Gly Ser Asp Ser Thr Lys Thr Thr Glu Lys Thr Gln
            165                 170                 175

Ser Met Ala Lys Lys Ala Glu Leu Glu Lys Tyr Leu Pro Phe Leu Asn
            180                 185                 190

Ser Leu Gln Lys Glu Tyr Glu Ser Leu Val Ser Lys Val Asn Thr Tyr
            195                 200                 205

Thr Asp Asn Leu Lys Lys Val Ile Asn Asn Cys Gln Leu Glu Lys Lys
            210                 215                 220

Glu Ala Glu Ile Thr Val Lys Lys Leu Gln Asp Tyr Asn Lys Met Asp
225                 230                 235                 240

Glu Lys Leu Glu Glu Tyr Lys Lys Ser Glu Lys Lys Asn Glu Val Lys
            245                 250                 255

Ser Ser Gly Leu Leu Glu Lys Leu Met Lys Ser Lys Leu Ile Lys Glu

```
                    260                 265                 270
Asn Glu Ser Lys Glu Ile Leu Ser Gln Leu Leu Asn Val Gln Thr Gln
                275                 280                 285

Leu Leu Thr Met Ser Ser Glu His Thr Cys Ile Asp Thr Asn Val Pro
            290                 295                 300

Asp Asn Ala Ala Cys Tyr Arg Tyr Leu Asp Gly Thr Glu Glu Trp Arg
305                 310                 315                 320

Cys Leu Leu Thr Phe Lys Glu Glu Gly Gly Lys Cys Val Pro Ala Ser
                325                 330                 335

Asn Val Thr Cys Lys Asp Asn Asn Gly Gly Cys Ala Pro Glu Ala Glu
            340                 345                 350

Cys Lys Met Thr Asp Ser Asn Lys Ile Val Cys Lys Cys Thr Lys Glu
                355                 360                 365

Gly Ser Glu Pro Leu Phe Glu Gly Val Phe Cys Ser
            370                 375                 380

<210> SEQ ID NO 13
<211> LENGTH: 380
<212> TYPE: PRT
<213> ORGANISM: Plasmodium vivax-like sp.

<400> SEQUENCE: 13

Asp Gln Val Thr Thr Gly Glu Ala Glu Ser Glu Ala Pro Glu Ile Leu
1               5                   10                  15

Val Pro Ala Gly Ile Ser Asp Tyr Asp Val Val Tyr Leu Lys Pro Leu
            20                  25                  30

Ala Gly Met Tyr Lys Thr Ile Lys Lys Gln Leu Glu Asn His Val Asn
        35                  40                  45

Ala Phe Asn Thr Asn Ile Thr Asp Met Leu Asp Ser Arg Leu Lys Lys
    50                  55                  60

Arg Asn Tyr Phe Leu Glu Val Leu Asn Ser Asp Leu Asn Pro Phe Lys
65                  70                  75                  80

Tyr Ser Ser Ser Gly Glu Tyr Ile Ile Lys Asp Pro Tyr Lys Leu Leu
                85                  90                  95

Asp Leu Glu Lys Lys Lys Leu Ile Gly Ser Tyr Lys Tyr Ile Gly
            100                 105                 110

Ala Ser Ile Asp Met Asp Leu Ala Thr Ala Asn Asp Gly Val Thr Tyr
        115                 120                 125

Tyr Asn Lys Met Gly Glu Leu Tyr Lys Thr His Leu Asp Gly Val Lys
    130                 135                 140

Thr Glu Ile Lys Lys Val Glu Asp Asp Ile Lys Lys Gln Asp Glu Glu
145                 150                 155                 160

Leu Lys Lys Leu Gly Asn Val Asn Ser Gln Asp Ser Lys Lys Asn Glu
                165                 170                 175

Phe Ile Ala Lys Lys Ala Glu Leu Glu Lys Tyr Leu Pro Phe Leu Asn
            180                 185                 190

Ser Leu Gln Lys Glu Tyr Glu Ser Leu Val Ser Lys Val Asn Thr Tyr
        195                 200                 205

Thr Asp Asn Leu Lys Lys Val Ile Asn Asn Cys Gln Leu Glu Lys Lys
    210                 215                 220

Glu Ala Glu Ile Thr Val Lys Lys Leu Gln Asp Tyr Asn Lys Met Asp
225                 230                 235                 240

Glu Lys Leu Glu Glu Tyr Lys Lys Ser Glu Lys Lys Asn Glu Val Lys
                245                 250                 255
```

```
Ser Ser Gly Leu Leu Glu Lys Leu Met Lys Ser Lys Leu Ile Lys Glu
            260                 265                 270

Asn Glu Ser Lys Glu Ile Leu Ser Gln Leu Leu Asn Val Gln Thr Gln
        275                 280                 285

Leu Leu Thr Met Ser Ser Glu His Thr Cys Ile Asp Thr Asn Val Pro
    290                 295                 300

Asp Asn Ala Ala Cys Tyr Arg Tyr Leu Asp Gly Thr Glu Glu Trp Arg
305                 310                 315                 320

Cys Leu Leu Thr Phe Lys Glu Gly Gly Lys Cys Val Pro Ala Ser
                325                 330                 335

Asn Val Thr Cys Lys Asp Asn Asn Gly Gly Cys Ala Pro Glu Ala Glu
                340                 345                 350

Cys Lys Met Thr Asp Ser Asn Lys Ile Val Cys Lys Cys Thr Lys Glu
            355                 360                 365

Gly Ser Glu Pro Leu Phe Glu Gly Val Phe Cys Ser
        370                 375                 380
```

<210> SEQ ID NO 14
<211> LENGTH: 281
<212> TYPE: PRT
<213> ORGANISM: Artificial Sequence
<220> FEATURE:
<223> OTHER INFORMATION: SYNTHETIC

<400> SEQUENCE: 14

```
Asp Gln Val Thr Thr Gly Glu Ala Glu Ser Glu Ala Pro Glu Ile Val
1               5                   10                  15

Pro Gly Ile Tyr Asp Val Val Tyr Lys Pro Leu Ala Gly Met Tyr Lys
            20                  25                  30

Thr Ile Lys Lys Leu Glu Asn His Val Asn Ala Asn Thr Asn Ile Asp
        35                  40                  45

Met Leu Asp Ser Ala Leu Lys Lys Ala Asn Tyr Phe Leu Val Leu Asn
    50                  55                  60

Ser Asp Leu Asn Pro Ser Gly Glu Tyr Ile Ile Lys Asp Pro Tyr Lys
65                  70                  75                  80

Leu Leu Asp Leu Glu Lys Lys Leu Gly Ser Tyr Lys Tyr Ile Gly
                85                  90                  95

Ala Ser Asp Asp Thr Ala Asn Asp Gly Tyr Tyr Lys Met Gly Leu Tyr
            100                 105                 110

Lys His Leu Val Lys Val Glu Ile Asp Lys Lys Gly Lys Ala Lys Lys
        115                 120                 125

Glu Leu Lys Tyr Leu Pro Phe Leu Ser Gln Lys Glu Tyr Leu Val Lys
    130                 135                 140

Val Tyr Thr Asp Leu Lys Lys Ile Asn Asn Cys Gln Glu Lys Lys Glu
145                 150                 155                 160

Glu Val Lys Leu Asp Tyr Lys Met Asp Glu Leu Tyr Lys Ser Lys Val
                165                 170                 175

Lys Ser Ser Gly Leu Leu Glu Lys Leu Met Ser Lys Leu Ile Glu Ser
            180                 185                 190

Lys Leu Ser Leu Leu Asn Val Gln Thr Gln Leu Met Ser Ser Glu His
        195                 200                 205

Cys Ile Asp Thr Asn Val Pro Asn Ala Ala Cys Tyr Arg Tyr Leu Asp
    210                 215                 220

Gly Thr Glu Glu Trp Arg Cys Leu Leu Phe Lys Glu Gly Lys Cys Val
225                 230                 235                 240
```

-continued

```
Pro Ala Asn Thr Cys Lys Asp Asn Gly Gly Cys Ala Pro Glu Ala Glu
            245                 250                 255

Cys Lys Met Asp Asn Ile Val Cys Lys Cys Thr Lys Glu Gly Ser Glu
            260                 265                 270

Pro Leu Phe Glu Gly Val Phe Cys Ser
        275                 280

<210> SEQ ID NO 15
<211> LENGTH: 6
<212> TYPE: PRT
<213> ORGANISM: ARTIFICIAL SEQUENCE
<220> FEATURE:
<223> OTHER INFORMATION: SYNTHETIC

<400> SEQUENCE: 15

Leu Asn Val Gln Thr Gln
1               5
```